US007138273B2

(12) United States Patent
Rommens et al.

(10) Patent No.: US 7,138,273 B2
(45) Date of Patent: Nov. 21, 2006

(54) METHOD OF IDENTIFYING NON-HOST PLANT DISEASE RESISTANCE GENES

(75) Inventors: Caius M. T. Rommens, Chesterfield, MO (US); Kathleen M M Swords, Chesterfield, MO (US); Hua Yan, Valley Park, MO (US); Bei Zhang, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 302 days.

(21) Appl. No.: 10/300,341

(22) Filed: Nov. 20, 2002

(65) Prior Publication Data

US 2003/0152975 A1     Aug. 14, 2003

Related U.S. Application Data

(62) Division of application No. 09/387,286, filed on Aug. 31, 1999, now Pat. No. 6,544,733.

(60) Provisional application No. 60/098,402, filed on Aug. 31, 1998.

(51) Int. Cl.
*C12Q 1/68*     (2006.01)
*C12N 1/00*     (2006.01)
*C12N 15/00*    (2006.01)
*C12N 15/63*    (2006.01)
*C12N 15/70*    (2006.01)

(52) U.S. Cl. .................. 435/320.1; 435/6; 435/410; 536/24.1

(58) Field of Classification Search .............. 435/6, 435/320.1, 410; 536/24.1
See application file for complete search history.

(56) References Cited

U.S. PATENT DOCUMENTS 5,312,912 A * 5/1994 Hadwiger et al. ......... 536/24.1

FOREIGN PATENT DOCUMENTS

WO    WO 96/30518    10/1996
WO    WO 98/02545    1/1998

OTHER PUBLICATIONS

Kamoun et al. A Gene Encoding a Protein Elicitor of Phytophthora infestans Is Down-REgulated During Infection of Plants Molecular Plant-Microbe Interactions Jan. 1997 vol. 10 No. 1.*
Cao et al., Generation of broad-spectrum disease resistance by overexpression of an essential regulatory gene in systemic acquired resistance, *Proc. Natl. Acad. Sci. USA* 95:6531-6536 (1998).
Daniels et al., Pea genes associated with non-host disease resistance to *Fusarium* are also active in race-specific disease resistance to *Pseudomonas*, *Plant Molecular Biology* 8:309-316 (1987).
Gowda et al., NRSA-1: a resistance gene homolog expressed in roots of non-host plants following parasitism by *Striga asiatica*, *The Plant Journal* 20(2):217-230 (1999).
Kamoun et al., A Gene Encoding a Protein Elicitor of *Phytophthora infestans* Is Down-Regulated During Infection of Potato, *MPMI* 10:13-20 (1997).
Kamoun et al., Resistance of *Nicotiana benthamiana* to *Phytophthora infestans* Is Medicated by the Recognition of the Elicitor Protein INF1, *The Plant Cell* 10:1413-1425 (1998).
Oldroyd et al., Genetically engineered broad-spectrum disease resistance in tomato, *Proc. Natl. Acad. Sci. USA* 95:10300-10305 (1998).
Rommens et al., Intergeneric Transfer and Functional Expression of the Tomato Disease Resistance Gene *Pto*, *The Plant Cell* 7:1537-1544 (1995).

* cited by examiner

*Primary Examiner*—James Ketter
*Assistant Examiner*—Konstantina Katcheves
(74) *Attorney, Agent, or Firm*—Timothy K. Ball

(57) ABSTRACT

The invention describes a new method to isolate disease resistance genes in plants. The method teaches to transiently express in susceptible plants large numbers of R-gene homologs or non-host inducible genes isolated from non-host resistant plants. These plants can be screened for either disease resistance or ability to respond with a hypersensitive response to pathogen-elicitor subjection. The invention also reports several R-genes and non-host inducible genes that have been successfully isolated using the described method. These R-genes trigger a hypersensitive response in tobacco that is dependent on the presence of the ubiquitous *P. infestans* elicitor INF1. The presented R-genes are predicted to be both the first R-genes isolated that confer resistance against *P. infestans* and the first R-genes involved in non-host resistance.

14 Claims, 9 Drawing Sheets

Figure 2  Plasmid map for pMON11770
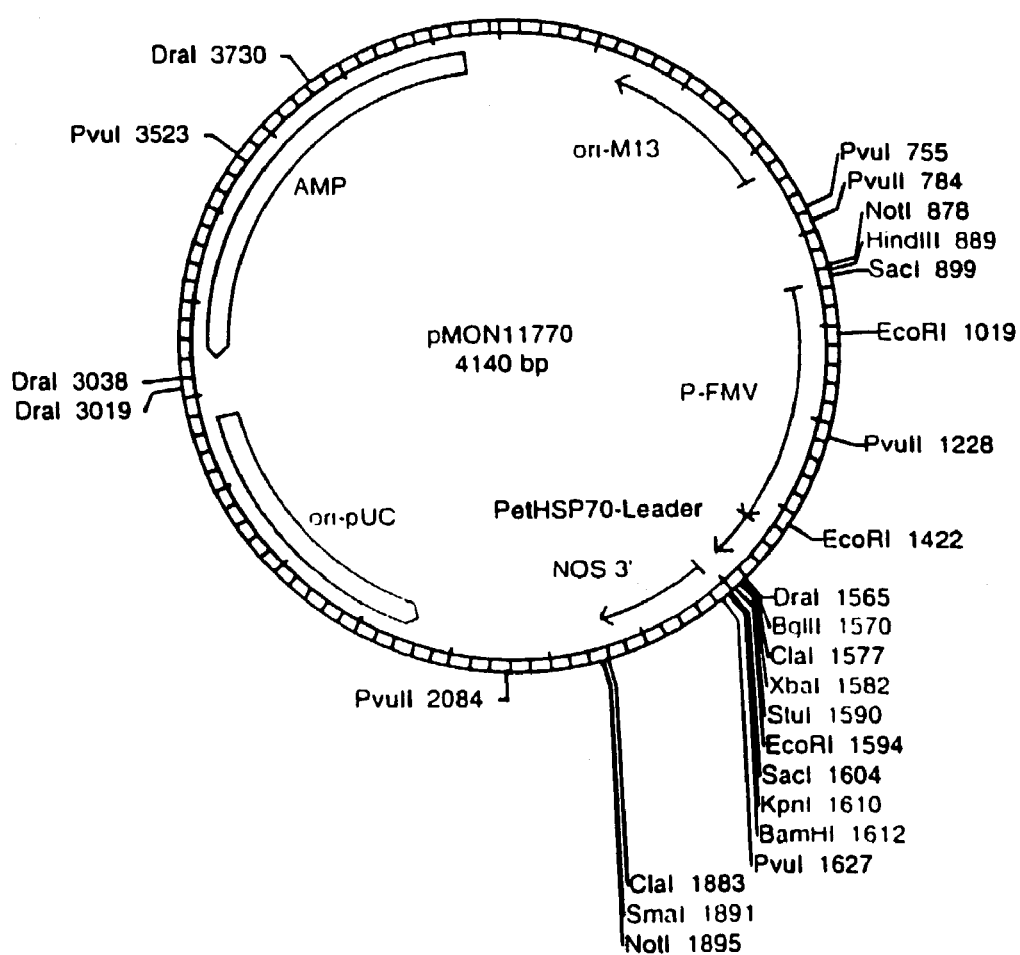

Figure 3A

```
            1                                                                    50
Enh4   ------TTIA  KKIYNDPTVT  SHFDAHAQCL  VTQIYSWREL  LLTILNDVLE
Enh8   -GGVGKTTIA  KKIYNDPTVT  SHFDAHAQCL  VTQIYSWREL  LLTILNDVLE
Enh2   MGGVGKTTLA  KKIYSDPIVT  SYFDVRAQCC  VTQVYSWREL  LLTILNDVLE
Enh9   ----------  ----------  ----------  ----------  ----------
Enh6   ----------  ----------  ----------  ----------  ----------
Enh5   ----------  ----------  ----------  ----------  ----------
Enh3   ----------  ----------  ----------  ----------  ----------
Enh1   ----------  ----------  ----------  ----------  ----------
Enh10  ----------  ----------  ----------  ----------  ----------
Enh7   ----------  ----------  ----------  ----------  ----------

51                                                                  100
Enh4   PADLNVKEDG  ELADELRRFL  LTKRFLILID  DVWDNKVWDN  LHLCFRDVRS
Enh8   PADLNVKEDG  ELADELRRFL  LTKRFLILID  DVWDNKVWDN  LHLCFRDVRS
Enh2   PTDRNLKEDG  ELADELRRFL  LTKRFLILVD  DVWDTKVWDY  LHMCCRGSRN
Enh9   ----------  ----------  ----------  ----------  ----------
Enh6   ----------  ----------  ----------  ----------  ----------
Enh5   ----------  ----------  ----------  ----------  ----------
Enh3   ----------  ----------  ----------  ----------  ----------
Enh1   ----------  ----------  ----------  ----------  ----------
Enh10  ----------  ----------  ----------  ----------  ----------
Enh7   ----------  ----------  ----------  ----------  ----------

101                                                                 150
Enh4   GSRIILTTRL  SDIANYVKCE  SDPHHLHLFR  DDESWTLLQK  EVFQGETCPP
Enh8   GSRIILTTRL  SDIANYVKCE  SDPHHLHLFR  DDESWTLLQK  EVFQGETCPP
Enh2   GSRIILTTRL  SDVASYAQCY  SKPHHLRLFR  DDESWTLLQK  EVFQGEICPP
Enh9   ----------  ----------  ----------  ----------  ----------
Enh6   ----------  ----------  ----------  ----------  ----------
Enh5   ----------  ----------  ----------  ----------  ----------
Enh3   ----------  ----------  ----------  ----------  ----------
Enh1   ----------  ----------  ----------  ----------  ----------
Enh10  ----------  ----------  ----------  ----------  ----------
```

Figure 3B

```
Enh7    --------- --------- --------- --------- --------I 151                                             200
Enh4    ELADVGSRIA RRC------ --------- --------- ----------
Enh8    ELADVGSRI- --------- --------- --------- ----------
Enh2    ELLDVGFEZQ KLV------ --------- --------- ----------
Enh9    ---------- -----DTLLG RRESSYQFDG ACFLKDIKDN KHGMHSLQNI
Enh6    GMGGVGKTTI ARAMFDTLLG RRESSYQFDG ACFLKDIKDN KHGMHSLQNI
Enh5    GMGGVGKTTI ARAMFDTLLG RRDSSYQFDG ACFLKDIKEN KRGMHSLQNT
Enh3    GMGGVGKTTI ARAIFDTL.. ....SYQFEV TCFLADVKEN KCGMHSLQNI
Enh1    GMGGVGKTTI ARAIFDTL.. ....SYQFEV TCFLADVKEN KCGMHSLQNI
Enh10   ------KTTI ARAIFDTL.. ....SYQFEG TCFLANVKEN KCGMHSLQNI
Enh7    QAWGEWAKRQ ZQESFLIL.. ....SYQFEV ACFLADVKEN KCGMHSLQNI 201                                             250
Enh4    ---------- ---------- ---------- ---------- ----------
Enh8    ---------- ---------- ---------- ---------- ----------
Enh2    ---------- ---------- ---------- ---------- ----------
Enh9    ILSNLLKEKA NY.NNEEDGK HQMASRLRSK KVLIVLDDID NKDHYLEYLA
Enh6    ILFNLLKEKA NY.NNEEDGK HQMASRLRSK KVLIVLDDID NKDHYLEYLA
Enh5    LLFELLRENA NY.NNEDDGK HQMASRLRSK KVLIVLDDID DKDHYLEYLA
Enh3    LLSELLRENA NYVNNKDDGK HLMACRLRSK KVLVVLDDID HZEH.LEYLA
Enh1    LLSELLRENA NYVNNKEDGK HLMARRLRSK KVLVVLDDID HRDH.LEYLA
Enh10   LLSELSRENA NYVNNKEDGK QLMARRLRSK KVLVVLDDID HRDH.LEYLA
Enh7    LLSELLRENA NCVNN.EDGK QLMARRLRFK KVLIVLDVID ...H.LDYLA 251                                             300
Enh4    ---------- ---------- ---------- ---------- ----------
Enh8    ---------- ---------- ---------- ---------- ----------
Enh2    ---------- ---------- ---------- ---------- ----------
Enh9    GDLDWFGNGS RIILTTRDKH LIEKNVVVYE VTALPDHESI QLFNQHAFRK
Enh6    GDLDWFGNGS RIILTTRDKH LIEKNVVVYE VTALPDHESI QLFNQHAFRK
Enh5    GDLDWFGNGS RIIVTTRDKH LIGKNDIIYE VTALPDHEAI QLFYQHAFKK
Enh3    GDLGWFGNGS RIIATTRDKH LIGKKDTLYE VTTLADHEAI RLFNRYTFKE
Enh1    GDLGWFGNGS RIIATTRDKH LIGKKDALYE VTTLADHEAI RLFNRYAFKE
Enh10   GDLGWFGNGS RIIATTRDKH LIGKKDALYE MTTLADHEAI QLFNRYAFKE
Enh7    GDPGWFGNGS RIIATIRDKH VTGKNDIVYE VTTLLEHDAI QLFNQYAFKE 301                   325
```

Figure 3C

```
Enh4   ----------    ----------    -----
Enh8   ----------    ----------    -----
Enh2   ----------    ----------    -----
Enh9   QDPDECFKEL    SLEVVNYA--    -----
Enh6   QDPDECFKEL    SLEVVNYA--    -----
Enh5   EVPDECFKEL    SLEVVNHA--    -----
Enh3   DVPDEFFEKL    TLEVVSH---    -----
Enh1   DVPDEVFEKL    TLEVVSHAK-    -----
Enh10  DVPDEFFEKL    TLEVVSHAK-    -----
Enh7   EVPDECFEKL    TLEVVSYANG    -----
```

Figure 4 Plasmid map for pMON17227
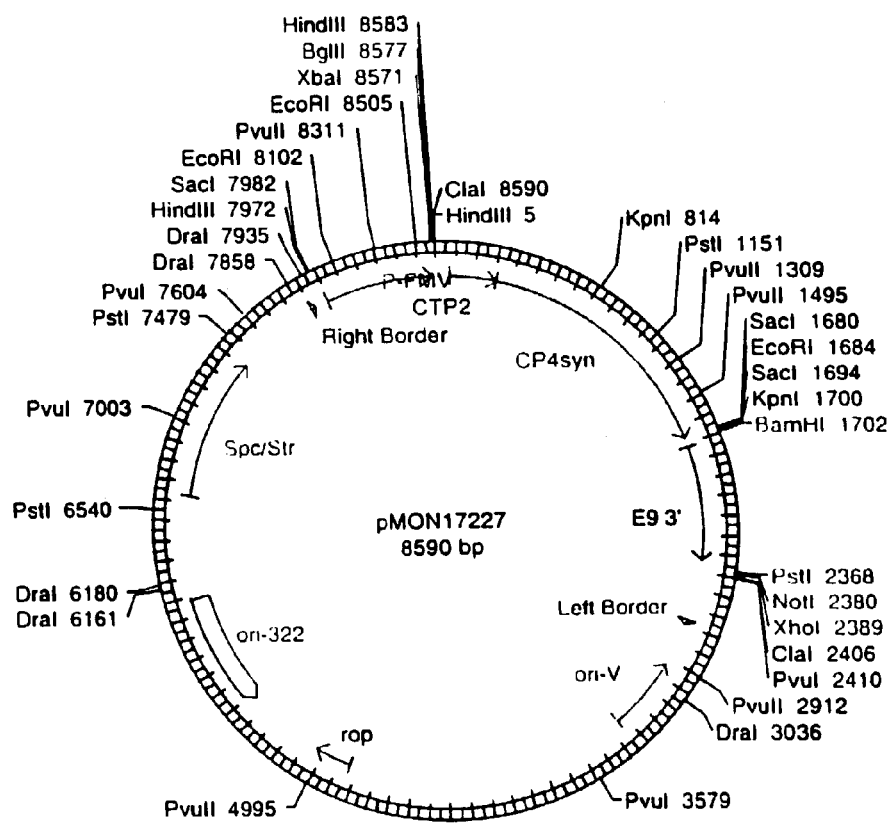

SEQUENCE LISTING

```
<160> NUMBER OF SEQ ID NOS: 66

<210> SEQ ID NO 1
<211> LENGTH: 489
<212> TYPE: DNA
<213> ORGANISM: Nicotiana tabacum

<400> SEQUENCE: 1
tcaggcatgg ggggagtggg caaaacgaca atagcaagag ccatttttga tacactctcg      60
tatcaatttg aagttacttg cttcctggcg gatgttaaag aaaacaaatg tggaatgcat     120
tctttgcaaa atatccttct ctcagaactg ttaagggaaa acgctaatta cgtgaataat     180
aaggaggacg gaaagcacct gatggctcgt agacttcgct ctaagaaggt tttagttgtg     240
cttgatgaca tagatcacag agaccatttg gagtacctag cagggatct tggttggttc      300 ggcaatggca gtagaattat tgcaacaaca agagacaagc atttgattgg gaagaaggat     360
gcattatatg aagtgactac actagctgac catgaagcta ttcgattgtt caatcgatac     420
```

```
gcttttaagg aagatgttcc agatgaggtt tttgagaagc taacgctgga ggtagtaagt    480
catgcgaaa                                                           489

<210> SEQ ID NO 2
<211> LENGTH: 489
<212> TYPE: DNA
<213> ORGANISM: Nicotiana tabacum

<400> SEQUENCE: 2
atggggggag tgggcaagac tacacttgca aagaagattt acagtgaccc aatagtcacc     60
tcttactttg atgtccgtgc tcagtgctgt gtgactcaag tatattcatg gcgagaattg    120
ttgcttacca ttttgaatga tgtgcttgag cctactgatc gcaatttaaa agaagatggc    180
gaattagctg atgagctgcg tcgattcttg ttgaccaaga gattcttaat tctcgttgat    240
gacgtgtggg acactaaagt gtgggactat ttacatatgt gctgtagagg ttctcgcaac    300
gggagtagaa ttattctaac gacacggctg agtgacgttg ccagttatgc tcaatgttat    360
agtaaacccc atcatcttcg tttattcaga gatgatgaga gttggacatt attacagaaa    420
gaggtgtttc aaggagagat ctgtccacct gaacttcttg atgtgggttt cgaatagcaa    480
aaacttgtg                                                           489

<210> SEQ ID NO 3
<211> LENGTH: 488
<212> TYPE: DNA
<213> ORGANISM: Nicotiana tabacum

<400> SEQUENCE: 3
gaattcaggc atgggggag tgggcaaaac gacaatagca agagccattt ttgatacact     60
ctcgtatcaa tttgaagtta cttgcttcct tgcggatgtt aaagaaaaca aatgtggaat    120
gcattctttg caaatatcc ttctctcaga actgttaagg aaaacgcta attacgtgaa     180 taataaggat gacggaaagc atctgatggc ttgtagactt cgttctaaga aggttttagt    240
tgtgcttgat gacatagatc actgagaaca tttggagtac ctagcagggg atcttggttg    300
gttcggcaat ggcagtagaa ttattgcaac aacaagagac aagcatttga ttgggaagaa    360
ggatacatta tatgaagtga ctacactagc tgaccatgaa gctattcgat tgttcaatcg    420
atacactttt aaggaagatg ttccagatga gttttttgag aagctaacgc tggaggtagt    480
aagtcatg                                                            488

<210> SEQ ID NO 4
<211> LENGTH: 472
<212> TYPE: DNA
<213> ORGANISM: Nicotiana tabacum

<400> SEQUENCE: 4
actacaattg caaagaagat ttacaatgat ccaacagtca cctctcactt tgatgcccat     60
gctcaatgtc ttgtgactca aatatattca tggagggagt tgttgctgac catcttgaat    120
gatgttcttg agcctgctga tctcaatgta aagaagatg gtgaattagc tgatgagcta    180
cgccgatttt tgttgactaa gagattcttg attctcattg atgatgtgtg ggacaacaaa    240
gtgtgggaca atttacatct gtgcttcaga gatgttcgga gtgggagtag aattattcta    300
acaacccggt tgagtgacat tgccaattat gttaaatgtg aaagtgatcc ccatcatctt    360
catttgttca gagatgatga gagttggaca ttgttacaga aagaggtatt tcaaggggag    420
```

```
acctgtccac cggaacttgc agatgtggga tctcggatag caaggcgttg ta            472
```

<210> SEQ ID NO 5
<211> LENGTH: 508
<212> TYPE: DNA
<213> ORGANISM: Nicotiana tabacum

<400> SEQUENCE: 5

```
aattcaggca tgggggagt gggcaaaacg acaatagcta gagctatgtt cgatactctt     60
ttaggaagaa gggatagttc ctatcaattt gatggtgctt gtttccttaa ggatattaaa   120
gaaacaaac gtggaatgca ttctcttcaa ataccCttc tctttgaact ttaagggaa      180
aatgctaatt acaataatga ggacgatgga agcaccaaa tggctagtag acttcgttct    240
aagaaggtcc taattgtgct tgatgacata atgataaag atcattattt ggagtattta    300
gcaggtgatc ttgattggtt tggtaatggc agtagaatta ttgtaacaac tagagacaag   360
catttgattg ggaagaatga tataatatat gaagtgactg cactacctga tcatgaagcc   420
attcaattgt tctatcaaca tgctttcaaa aagaggttc cagatgagtg ttttaaggag    480
ctttcattgg aggtagtaaa tcatgcta                                      508
```

<210> SEQ ID NO 6
<211> LENGTH: 509
<212> TYPE: DNA
<213> ORGANISM: Nicotiana tabacum

<400> SEQUENCE: 6

```
gaattcaggc atgggggag tgggcaaaac gacaatagca agagctatgt tgataccct     60
tttgggaaga agagaaagtt cctatcaatt tgatggtgct tgtttcctta aggatattaa   120
agataacaaa catggaatgc attctctgca aaatatcatt ctctttaatc ttttaaagga   180
aaaagccaat tacaataatg aggaggacgg aagcaccaa atggctagta gactgcgttc    240
taagaaggtc ctaattgtgc ttgatgacat agataataaa gatcattatt tggagtattt    300
agcaggtgat cttgattggt ttggtaatgg tagtagaatt atttaacaa ctagagacaa    360
gcatttaatt gagaagaatg ttgtagtata tgaagtgact gcactacctg atcatgaatc    420
cattcaattg ttcaatcagc atgctttcag aaaacaagat ccagatgagt gttttaagga    480
actctcattg gaggtagtaa attatgcta                                      509
```

<210> SEQ ID NO 7
<211> LENGTH: 477
<212> TYPE: DNA
<213> ORGANISM: Nicotiana tabacum

<400> SEQUENCE: 7

```
aggcatgggg ggagtgggca aaacgacaat agcaagagtc attttttgata ctctcatatc    60
aatttgaagt tgcttgtttc cttgcggatg tcaaagagaa caaatgtgga atgcactctt    120
tgcaaaatat ccttctctct gaactgttaa gagaaaacgc taattgcgtt aataatgagg    180
atggaaagca gttgatggct cgtagacttc gttttaaaaa ggtattaatt gtgcttgacg    240
tcatagatca tttggattac ctagctgggg atcctggttg gtttggcaat ggcagtagaa    300
ttattgcaac aattagagac aaacatgtga caggaagaa tgatatagta tatgaagtga    360
ctacactact tgaacatgat gctattcaat tgttcaatca atatgccttc aaagaagaag    420
ttccagatga gtgttttgag aagctaactt tggaggtagt aagttatgct aatggcc       477
```

<210> SEQ ID NO 8
<211> LENGTH: 477
<212> TYPE: DNA
<213> ORGANISM: Nicotiana tabacum

<400> SEQUENCE: 8

| | | | | | | |
|---|---|---|---|---|---|---|
| gctatccgag | atcccacatc | tgcaagttcc | ggtggacagg | tctccccttg | aaatacctct | 60 |
| ttctgtaaca | atgtccaact | ctcatcatct | ctgaacaaat | gaagatgatg | gggatcactt | 120 |
| tcacatttaa | cataattggc | aatgtcactc | aaccgggttg | ttagaataat | tctactccca | 180 |
| ctccgaacat | ctctgaagca | cagatgtaaa | ttgtcccaca | ctttgttgtc | ccacacatca | 240 |
| tcaatgagaa | tcaagaatct | cttagtcaac | aaaaatcggc | gtagctcatc | agctaattca | 300 |
| ccatcttctt | ttacattgag | atcagcaggc | tcaagaacat | cattcaagat | ggtcagcaac | 360 |
| aactccctcc | atgaatatat | ttgagtcaca | agacattgag | catgggcatc | aaagtgagag | 420 |
| gtgactgttg | gatcattgta | aatcttcttt | gcaattgtag | tcttgcccac | tccccc | 477 |

<210> SEQ ID NO 9
<211> LENGTH: 459
<212> TYPE: DNA
<213> ORGANISM: Nicotiana tabacum

<400> SEQUENCE: 9

| | | | | | | |
|---|---|---|---|---|---|---|
| ttagcataat | ttactacctc | caatgagagt | tccttaaaac | actcatctgg | atcttgtttt | 60 |
| ctgaaagcat | gctgattgaa | caattgaatg | gattcatgat | caggtagtgc | agtcacttca | 120 |
| tatactacaa | cattcttctc | aattaaatgc | ttgtctctag | ttgttaaaat | aattctacta | 180 |
| ccattaccaa | accaatcaag | atcacctgct | aaatactcca | ataatgatc | tttattatct | 240 |
| atgtcatcaa | gcacaattag | gaccttctta | gaacgcagtc | tactagccat | ttggtgcttt | 300 |
| ccgtcctcct | cattattgta | attggctttt | tcctttaaaa | gattagagag | aatgatattt | 360 |
| tgcagagaat | gcattccatg | tttgttatct | ttaatatcct | taaggaaaca | agcaccatca | 420 |
| aattgatagg | aactttccct | tcttcccaaa | aggtatca | | | 459 |

<210> SEQ ID NO 10
<211> LENGTH: 470
<212> TYPE: DNA
<213> ORGANISM: Nicotiana tabacum

<400> SEQUENCE: 10

| | | | | | | |
|---|---|---|---|---|---|---|
| aaaacgacaa | tagcaagggc | tattttgat | actctctcat | atcaatttga | aggtacttgt | 60 |
| ttccttgcga | atgttaaaga | aaacaaatgt | ggaatgcatt | ctttgcaaaa | tatccttctc | 120 |
| tcagaactgt | caagggaaaa | cgctaattac | gtgaataata | aggaggacgg | aaagcagctg | 180 |
| atggctcgta | gacttcgttc | taagaaggtt | ttagttgtgc | ttgatgacat | agatcacaga | 240 |
| gaccatttgg | agtacctagc | aggggatctt | ggttggttcg | gcaatggcag | tagaattatt | 300 |
| gcaacaacaa | gagacaagca | tttgattggg | aagaaggacg | cattatatga | aatgactaca | 360 |
| ctagctgacc | atgaagctat | tcaattgttc | aatcgatacg | cttttaagga | agatgttcca | 420 |
| gatgagttct | ttgagaagct | aacgctggag | gtagtaagtc | atgctaaagg | | 470 |

<210> SEQ ID NO 11
<211> LENGTH: 157
<212> TYPE: PRT
<213> ORGANISM: Nicotiana tabacum

<400> SEQUENCE: 11

```
Thr Thr Ile Ala Lys Lys Ile Tyr Asn Asp Pro Val Thr Ser His
 1               5                  10                  15

Phe Asp Ala His Ala Gln Cys Leu Val Thr Gln Ile Tyr Ser Trp Arg
                 20                  25                  30

Glu Leu Leu Leu Thr Ile Leu Asn Asp Val Leu Glu Pro Ala Asp Leu
             35                  40                  45

Asn Val Lys Glu Asp Gly Glu Leu Ala Asp Glu Leu Arg Arg Phe Leu
         50                  55                  60

Leu Thr Lys Arg Phe Leu Ile Leu Ile Asp Asp Val Trp Asp Asn Lys
 65                  70                  75                  80

Val Trp Asp Asn Leu His Leu Cys Phe Arg Asp Val Arg Ser Gly Ser
                 85                  90                  95

Arg Ile Ile Leu Thr Thr Arg Leu Ser Asp Ile Ala Asn Tyr Val Lys
                100                 105                 110

Cys Glu Ser Asp Pro His His Leu His Leu Phe Arg Asp Asp Glu Ser
                115                 120                 125

Trp Thr Leu Leu Gln Lys Glu Val Phe Gln Gly Glu Thr Cys Pro Pro
130                 135                 140

Glu Leu Ala Asp Val Gly Ser Arg Ile Ala Arg Arg Cys
145                 150                 155
```

```
<210> SEQ ID NO 12
<211> LENGTH: 158
<212> TYPE: PRT
<213> ORGANISM: Nicotiana tabacum

<400> SEQUENCE: 12

Gly Gly Val Gly Lys Thr Thr Ile Ala Lys Lys Ile Tyr Asn Asp Pro
 1               5                  10                  15

Thr Val Thr Ser His Phe Asp Ala His Ala Gln Cys Leu Val Thr Gln
                 20                  25                  30

Ile Tyr Ser Trp Arg Glu Leu Leu Leu Thr Ile Leu Asn Asp Val Leu
             35                  40                  45

Glu Pro Ala Asp Leu Asn Val Lys Glu Asp Gly Glu Leu Ala Asp Glu
         50                  55                  60

Leu Arg Arg Phe Leu Leu Thr Lys Arg Phe Leu Ile Leu Ile Asp Asp
 65                  70                  75                  80

Val Trp Asp Asn Lys Val Trp Asp Asn Leu His Leu Cys Phe Arg Asp
                 85                  90                  95

Val Arg Ser Gly Ser Arg Ile Ile Leu Thr Thr Arg Leu Ser Asp Ile
                100                 105                 110

Ala Asn Tyr Val Lys Cys Glu Ser Asp Pro His His Leu His Leu Phe
                115                 120                 125

Arg Asp Asp Glu Ser Trp Thr Leu Leu Gln Lys Glu Val Phe Gln Gly
130                 135                 140

Glu Thr Cys Pro Pro Glu Leu Ala Asp Val Gly Ser Arg Ile
145                 150                 155
```

```
<210> SEQ ID NO 13
<211> LENGTH: 163
<212> TYPE: PRT
<213> ORGANISM: Nicotiana tabacum

<400> SEQUENCE: 13

Met Gly Gly Val Gly Lys Thr Thr Leu Ala Lys Lys Ile Tyr Ser Asp
 1               5                  10                  15
```

```
Pro Ile Val Thr Ser Tyr Phe Asp Val Arg Ala Gln Cys Cys Val Thr
                    20                  25                  30

Gln Val Tyr Ser Trp Arg Glu Leu Leu Thr Ile Leu Asn Asp Val
            35                  40                  45

Leu Glu Pro Thr Asp Arg Asn Leu Lys Glu Asp Gly Glu Leu Ala Asp
     50                  55                  60

Glu Leu Arg Arg Phe Leu Leu Thr Lys Arg Phe Leu Ile Leu Val Asp
 65                  70                  75                  80

Asp Val Trp Asp Thr Lys Val Trp Asp Tyr Leu His Met Cys Cys Arg
                 85                  90                  95

Gly Ser Arg Asn Gly Ser Arg Ile Ile Leu Thr Thr Arg Leu Ser Asp
                100                 105                 110

Val Ala Ser Tyr Ala Gln Cys Tyr Ser Lys Pro His His Leu Arg Leu
            115                 120                 125

Phe Arg Asp Asp Glu Ser Trp Thr Leu Leu Gln Lys Glu Val Phe Gln
130                 135                 140

Gly Glu Ile Cys Pro Pro Glu Leu Leu Asp Val Gly Phe Glu Glx Gln
145                 150                 155                 160

Lys Leu Val

<210> SEQ ID NO 14
<211> LENGTH: 152
<212> TYPE: PRT
<213> ORGANISM: Nicotiana tabacum

<400> SEQUENCE: 14

Asp Thr Leu Leu Gly Arg Arg Glu Ser Ser Tyr Gln Phe Asp Gly Ala
  1               5                  10                  15

Cys Phe Leu Lys Asp Ile Lys Asp Asn Lys His Gly Met His Ser Leu
                 20                  25                  30

Gln Asn Ile Ile Leu Ser Asn Leu Leu Lys Glu Lys Ala Asn Tyr Asn
             35                  40                  45

Asn Glu Glu Asp Gly Lys His Gln Met Ala Ser Arg Leu Arg Ser Lys
     50                  55                  60

Lys Val Leu Ile Val Leu Asp Asp Ile Asp Asn Lys Asp His Tyr Leu
 65                  70                  75                  80

Glu Tyr Leu Ala Gly Asp Leu Asp Trp Phe Gly Asn Gly Ser Arg Ile
                 85                  90                  95

Ile Leu Thr Thr Arg Asp Lys His Leu Ile Glu Lys Asn Val Val Val
                100                 105                 110

Tyr Glu Val Thr Ala Leu Pro Asp His Glu Ser Ile Gln Leu Phe Asn
            115                 120                 125

Gln His Ala Phe Arg Lys Gln Asp Pro Asp Glu Cys Phe Lys Glu Leu
130                 135                 140

Ser Leu Glu Val Val Asn Tyr Ala
145                 150

<210> SEQ ID NO 15
<211> LENGTH: 167
<212> TYPE: PRT
<213> ORGANISM: Nicotiana tabacum

<400> SEQUENCE: 15

Gly Met Gly Gly Val Gly Lys Thr Thr Ile Ala Arg Ala Met Phe Asp
  1               5                  10                  15

Thr Leu Leu Gly Arg Arg Glu Ser Ser Tyr Gln Phe Asp Gly Ala Cys
```

```
                    20                  25                  30
Phe Leu Lys Asp Ile Lys Asp Asn Lys His Gly Met His Ser Leu Gln
             35                  40                  45

Asn Ile Ile Leu Phe Asn Leu Leu Lys Glu Lys Ala Asn Tyr Asn Asn
 50                  55                  60

Glu Glu Asp Gly Lys His Gln Met Ala Ser Arg Leu Arg Ser Lys Lys
 65                  70                  75                  80

Val Leu Ile Val Leu Asp Asp Ile Asp Asn Lys Asp His Tyr Leu Glu
                 85                  90                  95

Tyr Leu Ala Gly Asp Leu Asp Trp Phe Gly Asn Gly Ser Arg Ile Ile
            100                 105                 110

Leu Thr Thr Arg Asp Lys His Leu Ile Glu Lys Asn Val Val Val Tyr
            115                 120                 125

Glu Val Thr Ala Leu Pro Asp His Glu Ser Ile Gln Leu Phe Asn Gln
            130                 135                 140

His Ala Phe Arg Lys Gln Asp Pro Asp Glu Cys Phe Lys Glu Leu Ser
145                 150                 155                 160

Leu Glu Val Val Asn Tyr Ala
                165

<210> SEQ ID NO 16
<211> LENGTH: 167
<212> TYPE: PRT
<213> ORGANISM: Nicotiana tabacum

<400> SEQUENCE: 16

Gly Met Gly Gly Val Gly Lys Thr Thr Ile Ala Arg Ala Met Phe Asp
 1               5                  10                  15

Thr Leu Leu Gly Arg Arg Asp Ser Ser Tyr Gln Phe Asp Gly Ala Cys
             20                  25                  30

Phe Leu Lys Asp Ile Lys Glu Asn Lys Arg Gly Met His Ser Leu Gln
             35                  40                  45

Asn Thr Leu Leu Phe Glu Leu Leu Arg Glu Asn Ala Asn Tyr Asn Asn
 50                  55                  60

Glu Asp Asp Gly Lys His Gln Met Ala Ser Arg Leu Arg Ser Lys Lys
 65                  70                  75                  80

Val Leu Ile Val Leu Asp Asp Ile Asp Asp Lys Asp His Tyr Leu Glu
                 85                  90                  95

Tyr Leu Ala Gly Asp Leu Asp Trp Phe Gly Asn Gly Ser Arg Ile Ile
            100                 105                 110

Val Thr Thr Arg Asp Lys His Leu Ile Gly Lys Asn Asp Ile Ile Tyr
            115                 120                 125

Glu Val Thr Ala Leu Pro Asp His Glu Ala Ile Gln Leu Phe Tyr Gln
            130                 135                 140

His Ala Phe Lys Lys Glu Val Pro Asp Glu Cys Phe Lys Glu Leu Ser
145                 150                 155                 160

Leu Glu Val Val Asn His Ala
                165

<210> SEQ ID NO 17
<211> LENGTH: 160
<212> TYPE: PRT
<213> ORGANISM: Nicotiana tabacum

<400> SEQUENCE: 17

Gly Met Gly Gly Val Gly Lys Thr Thr Ile Ala Arg Ala Ile Phe Asp
```

```
                   1               5                  10                 15
Thr Leu Ser Tyr Gln Phe Glu Val Thr Cys Phe Leu Ala Asp Val Lys
                 20                  25                 30

Glu Asn Lys Cys Gly Met His Ser Leu Gln Asn Ile Leu Leu Ser Glu
                 35                  40                 45

Leu Leu Arg Glu Asn Ala Asn Tyr Val Asn Asn Lys Asp Asp Gly Lys
             50                  55                  60

His Leu Met Ala Cys Arg Leu Arg Ser Lys Lys Val Leu Val Val Leu
 65                  70                  75                  80

Asp Asp Ile Asp His Glx Glu His Leu Glu Tyr Leu Ala Gly Asp Leu
                 85                  90                  95

Gly Trp Phe Gly Asn Gly Ser Arg Ile Ile Ala Thr Thr Arg Asp Lys
                100                 105                 110

His Leu Ile Gly Lys Lys Asp Thr Leu Tyr Glu Val Thr Thr Leu Ala
                115                 120                 125

Asp His Glu Ala Ile Arg Leu Phe Asn Arg Tyr Thr Phe Lys Glu Asp
             130                 135                 140

Val Pro Asp Glu Phe Phe Glu Lys Leu Thr Leu Glu Val Val Ser His
145                 150                 155                 160

<210> SEQ ID NO 18
<211> LENGTH: 162
<212> TYPE: PRT
<213> ORGANISM: Nicotiana tabacum

<400> SEQUENCE: 18

Gly Met Gly Gly Val Gly Lys Thr Thr Ile Ala Arg Ala Ile Phe Asp
 1               5                  10                  15

Thr Leu Ser Tyr Gln Phe Glu Val Thr Cys Phe Leu Ala Asp Val Lys
                 20                  25                  30

Glu Asn Lys Cys Gly Met His Ser Leu Gln Asn Ile Leu Leu Ser Glu
                 35                  40                  45

Leu Leu Arg Glu Asn Ala Asn Tyr Val Asn Asn Lys Glu Asp Gly Lys
             50                  55                  60

His Leu Met Ala Arg Arg Leu Arg Ser Lys Lys Val Leu Val Val Leu
 65                  70                  75                  80

Asp Asp Ile Asp His Arg Asp His Leu Glu Tyr Leu Ala Gly Asp Leu
                 85                  90                  95

Gly Trp Phe Gly Asn Gly Ser Arg Ile Ile Ala Thr Thr Arg Asp Lys
                100                 105                 110

His Leu Ile Gly Lys Lys Asp Ala Leu Tyr Glu Val Thr Thr Leu Ala
                115                 120                 125

Asp His Glu Ala Ile Arg Leu Phe Asn Arg Tyr Ala Phe Lys Glu Asp
             130                 135                 140

Val Pro Asp Glu Val Phe Glu Lys Leu Thr Leu Glu Val Val Ser His
145                 150                 155                 160

Ala Lys

<210> SEQ ID NO 19
<211> LENGTH: 156
<212> TYPE: PRT
<213> ORGANISM: Nicotiana tabacum

<400> SEQUENCE: 19

Lys Thr Thr Ile Ala Arg Ala Ile Phe Asp Thr Leu Ser Tyr Gln Phe
 1               5                  10                  15
```

```
Glu Gly Thr Cys Phe Leu Ala Asn Val Lys Glu Asn Lys Cys Gly Met
            20                  25                  30
His Ser Leu Gln Asn Ile Leu Leu Ser Glu Leu Ser Arg Glu Asn Ala
        35                  40                  45
Asn Tyr Val Asn Asn Lys Glu Asp Gly Lys Gln Leu Met Ala Arg Arg
    50                  55                  60
Leu Arg Ser Lys Lys Val Leu Val Leu Asp Asp Ile Asp His Arg
 65                  70                  75                  80
Asp His Leu Glu Tyr Leu Ala Gly Asp Leu Gly Trp Phe Gly Asn Gly
                85                  90                  95
Ser Arg Ile Ile Ala Thr Thr Arg Asp Lys His Leu Ile Gly Lys Lys
            100                 105                 110
Asp Ala Leu Tyr Glu Met Thr Thr Leu Ala Asp His Glu Ala Ile Gln
        115                 120                 125
Leu Phe Asn Arg Tyr Ala Phe Lys Glu Asp Val Pro Asp Glu Phe Phe
    130                 135                 140
Glu Lys Leu Thr Leu Glu Val Val Ser His Ala Lys
145                 150                 155

<210> SEQ ID NO 20
<211> LENGTH: 159
<212> TYPE: PRT
<213> ORGANISM: Nicotiana tabacum

<400> SEQUENCE: 20

Gln Ala Trp Gly Glu Trp Ala Lys Arg Gln Glx Gln Glu Ser Phe Leu
  1               5                  10                  15
Ile Leu Ser Tyr Gln Phe Glu Val Ala Cys Phe Leu Ala Asp Val Lys
            20                  25                  30
Glu Asn Lys Cys Gly Met His Ser Leu Gln Asn Ile Leu Leu Ser Glu
        35                  40                  45
Leu Leu Arg Glu Asn Ala Asn Cys Val Asn Asn Glu Asp Gly Lys Gln
    50                  55                  60
Leu Met Ala Arg Arg Leu Arg Phe Lys Lys Val Leu Ile Val Leu Asp
 65                  70                  75                  80
Val Ile Asp His Leu Asp Tyr Leu Ala Gly Asp Pro Gly Trp Phe Gly
                85                  90                  95
Asn Gly Ser Arg Ile Ile Ala Thr Ile Arg Asp Lys His Val Thr Gly
            100                 105                 110
Lys Asn Asp Ile Val Tyr Glu Val Thr Thr Leu Leu Glu His Asp Ala
        115                 120                 125
Ile Gln Leu Phe Asn Gln Tyr Ala Phe Lys Glu Val Pro Asp Glu
    130                 135                 140
Cys Phe Glu Lys Leu Thr Leu Glu Val Val Ser Tyr Ala Asn Gly
145                 150                 155

<210> SEQ ID NO 21
<211> LENGTH: 504
<212> TYPE: DNA
<213> ORGANISM: Nicotiana tabacum

<400> SEQUENCE: 21
gggggagtgg gtaaaacgac aatagcaaaa gccattttg atacactctc gtatcagttt      60
gaagctgctt gtttccttgc ggatgttaaa gaaaatgaaa aagatatca actgcattct    120 ttacaaaaca ctcttctctc taaattgtta agaagcaaag atgattgtgt caataataag    180
```

-continued

```
cttgaaggga agcagatgat tccggacaga ctttgttcta agaaggtcct aattgtgctt      240
gatgacatag atgatggaga acaattggag tatttagcag gtgatcttag ttggtttggt      300
aagggcacta gagttatcgt aacaactaga gacaagcatt tgatagggaa gaatgatgta      360
atatatgaag tgactacact acctgatcat gaagctacgc agttgttcaa gcaatatgct      420
tttaaagaag aagatccaga tgtgtgtttt gagaagctaa tattggacgt agtaagtcat      480
gctaaaggcc tgcctctagc actt                                              504
```

<210> SEQ ID NO 22
<211> LENGTH: 517
<212> TYPE: DNA
<213> ORGANISM: Nicotiana tabacum

<400> SEQUENCE: 22

```
gggggattgg gtaagactac actagcgaag aagatttaca atgatccaac agtcacctct      60
cactttgatg tccatgctca atgtcttgtg actcaaatat attcatggag ggagttgttg      120
ctgaccatct tgaatgatgt tcttgagcct gctgaccgca atgaaaaaga agacggtgaa      180
ttagctgatg agctacgccg attttttgttg actaagagat tcttgattct cattgatgat      240
gtgtgggaca acaaagtgtg ggacaattta catatgtgct tcagagatgt tcggaatggg      300
agtagaatta ttctaacaac ccggctgagt gacattgcca attatgttaa atgtgaaagt      360
gatccccatc atcttcgttt gttcagagat gatgagagtt ggacattgtt acagaaagag      420
gtatttcaag gggagacctg tccacctgaa cttgcagatg tgggatctcg gatagcaagg      480
cgttgtagag gccttccttt ctccctcgac tcgagaa                                517
```

<210> SEQ ID NO 23
<211> LENGTH: 513
<212> TYPE: DNA
<213> ORGANISM: Nicotiana tabacum

<400> SEQUENCE: 23

```
tggcgggatt gggtaagacg acattggctg agaaaataag agcaagggcg aaaaagaaa       60 ggttctttga tgaggttgtc atggtaactg tcagtcaaca accagacttg aaaacaattc      120
aagctgagat agctggagga atcggtctaa cattacaagg cgacaatttt tggaatcgtg      180
gagatcagtt gcgttcaagg ttaatgggtc aggacagcat ccttgtaatc ttggatgatg      240
tctgggaggc tcttgatctg aacaagcttg gaattcctag tggtagcaat cacaaccatc      300
ggtgcaaagt aacattgaca acgcgactcc gagatgtttg tgaaacaatg gaggctcgaa      360
agatcataga agttggaatc ttacctgaaa aggaagcatg gtccttttc agacagaaag       420 ccggtaattc ggtagctgat ctttctcttc atcacacagc aaaagatgtt gtgaaagaat      480
gcaaggggct tcctttcgcc gttgactcga gaa                                    513
```

<210> SEQ ID NO 24
<211> LENGTH: 644
<212> TYPE: DNA
<213> ORGANISM: Nicotiana tabacum

<400> SEQUENCE: 24

```
cgggcccccc tcgaggtcga cggtatcgat aagcttgata tcgaattcct gcagcccggg      60
ggatccgccc attcaggcat gggggagtg ggcaagacaa cacttgctaa agccgtttac      120
aatgatgaga gggtgaagaa acatttttggt ttgaaagctt ggttttgtgt ttctgaggca     180
```

```
tatgatgctt tcagaataac aaaagggata cttcaagaaa ttggaaaatt tgactcaaag      240
gatgtccaca acaatcttaa tcagcttcaa gtcaaattga aggaaagctt gaagggaaag      300
aagttcctta ttgttttgga tgatgtgtgg aatgacaact acaatgagtg ggatgacttg      360
agaaatgctt ttgtacaagg agatatagga agtaagatca ttatgacgac acgtaaagat      420
agtgttgcct tgatgatggg ttgtggggca atctacgtgg gaattctgtc tagtgaagac      480
tcttgggctt tattcaaacg acattcacta gaaaataggg atcctgagga acatccagaa      540
tttgaagagg ttggaaaaca aattgcagac aagtgcaaag gtctgccttt ctccctcgac      600
tcgagaaggg ctagagcgcc gccacccgcg gtggagctcc actt                      644

<210> SEQ ID NO 25
<211> LENGTH: 637
<212> TYPE: DNA
<213> ORGANISM: Nicotiana tabacum

<400> SEQUENCE: 25
gggtacgggc cccctcgag gtcgacggta tcgataagct tgatatcgaa ttcctgcagc       60 ccggggatc cgcccttgaa ttcaggcatg gggggagtgg gcaaaacgac tatagcaaaa      120 gctgttttg atacactctc acctcaattt caaggtgcaa gtttccttgc ggatgtcaaa      180
gaaactaaca caaatgaaat gcattctctg caaaatatcc ttctctctga attgttaagg      240
gaagataaaa gatatgtgaa taataaggag aagggaagc gtctgatggc tcatagactt      300
cgttttatga aggttttagt tgtccttgat gacatcaatc atcatgatca tttggagtat      360
ttagcagggg atcttcgttg gtttggcagt ggaagtagaa ttatcgcaac aactagaaac      420
aagcaaatta tagggaagaa taatgtagta tatgaagtga ctacactgcc cgaacatgat      480
gctattcagt tgttcaatca ttatgctttt aaggacgaag ctcctgatga gcatattaag      540
aagttggctc tagaggtagt aagtcatgct aaaggcctgc tctcgcact cgactcgaga      600 agggctagag cggccgccac ccgcgtggag ctccagt                              637

<210> SEQ ID NO 26
<211> LENGTH: 534
<212> TYPE: DNA
<213> ORGANISM: Nicotiana tabacum

<400> SEQUENCE: 26
ttgaattcag gaatgggagg agtgggtaag acaactctag ctaacaaact atttcttgat       60
ctgttagttg tttctcattt tgatgtccgt gcacaatgtt gtgtatctca agcatataca      120
cgtaaagact tgttactaac cattcttcgg ggtgtgaaga aggatacagt tatcagtgat      180
aaactaccag agaatgaatt ggcagataag ttgcgtaaac ttctatttgg tcagaggtat      240
cttatcctta ttgatgatgt ctgggaaact actgcatgtg atgatctaat gccttgcttc      300
tatgaagcca ataatggaag tagacttatc ctgacaactc gccatgatca tgttgcctac      360
catgctaaac tcgttagtga tcctcatttt cttcgaaagt ttactcttga gaaagttgg      420 atgctattga cgaataaggt gttcaacaaa aaagttgcc ctgttgtctt agaagatgtt      480
ggccaaaaga tagcacaaaa gtgtggaggt ctgcctctct ccctcgactc gaga           534

<210> SEQ ID NO 27
<211> LENGTH: 532
<212> TYPE: DNA
<213> ORGANISM: Nicotiana tabacum

<400> SEQUENCE: 27
```

```
ttgaattcag gcatgccggg agtgggtaag actacactag caaagaagat ttacaatgat    60
ccagaagtca actctcgctt cgatgtccat gctcaatgtg ttgtgactca attatattca   120
tggagagagt tgttgctcac cattttgaat gacgtgcttg agccttctga tcgcaatgaa   180
aaagaagatg gtgaaatagc tgatgagcta cgccgatttt tgttgaccaa gagattcttg   240
attttcattg atgatgtgtg ggactataaa gtgtgggaca atctacgtat gtgcttcagt   300
gatgtttcaa aaggagtag aattattcta acaacccgct tgaatgatgt tgccgaatat    360
gtcaaatgtg aaagtgatcc ccatcatctt cgtttattca gagatgatga gagttggaca   420
ttattacaga gagaagtctt tcaaggagag agctgtccac ctaaacttaa agatgtggga   480
tttgaaatat caaaaagttg tagaggcctg cctctcgccc tcgactcgag aa           532
```

```
<210> SEQ ID NO 28
<211> LENGTH: 519
<212> TYPE: DNA
<213> ORGANISM: Nicotiana tabacum

<400> SEQUENCE: 28
```

```
ntgaattcag gcatgccggg agtgggcaaa acgacaatag taagagcaat ttttgatatg    60
ctctcacctc aatttgatgg tgcttgtttc tttgcggata tcaaagaaac taaagaaatg   120
cactctctgc aaaatatcct tctctctgaa ctgctaagga aaaagaaga atacgtgaat    180
aataaggtgg atgggaagca cttgatggct cgtagacttc gttttaagaa ggtcttagtt   240
gtgcttgatg acataaaatca cggagaccat ttggataacc tagcagggga ccttgattgg   300
tttggcaagg gcagtaggat tattgcaact acaagaggca acatttgat agggaagaat    360
gatgtagtat atgaagtgac cacactagtt gatcatcaag ctatccaatt gttcaatcaa   420
cttgctttca aggacgaagt tccagataag tcatttgaga agctaacgtt ggaggtggta   480
ggtcatgcga atggcctgcc tttctcactc gactcgaga                          519
```

```
<210> SEQ ID NO 29
<211> LENGTH: 540
<212> TYPE: DNA
<213> ORGANISM: Nicotiana tabacum

<400> SEQUENCE: 29
```

```
ttgaattcag gcatgggggg attgggtaaa ctactttggc ttacagagtg tataatgata    60
agtccattgt tgatcatttc gatgtttgtg cttggtgcac agtcgaccag gaaagtaatg   120
agaaaaagtt gttgcagaaa atttttcaatc aagttatagg tttgaaagaa cgattcaatg   180
aggatcatga catagatgat gatgttgctg ataagctgcg gagacaacta tttggaaaac   240
ggtaccttat tgtcttggat gacatgtggg atactgcaac atttgatgag ctaacaagac   300
cttttcctga attacagaaa ggaagcgag tgattttaac aagtcggaaa aaggaagttg    360
cttttgcatgg aaaatgccac agtgatcctc tttatcttcg attgctaaga tcagaagaaa   420
gttgggagtt attagagaaa agggtattcg gagaagaacg ttgccctgat gaactaaagg   480
atgtcggaaa aaagatatct cgaaagtgtg atggccttcc tctagccctt gactcgagaa   540
```

```
<210> SEQ ID NO 30
<211> LENGTH: 499
<212> TYPE: DNA
<213> ORGANISM: Nicotiana tabacum

<400> SEQUENCE: 30
```

```
gggggagtgg gcaagacgac aatagcaaga gctattttg atatacactc atctaaattt      60
gatggtgctt gtttccttcc ggtcagtaaa gaaaacaagc atgaaataca ttctcttcaa    120
agtattcttc tctctaaact ggtaggggaa aagaaaatt gtgtgcttga taaggaggac    180
gggaggtacc tgatggctcg tagacttcgt ttcaagaagg ttctagttgt gctagataac    240
atagatcatg tagaccaatt ggattaccta gcagggatc ttagttggtt tggcaatggc    300
agcagaataa ttgcaacaac taggaacagg catttcaaaa ggaaaaatga tgccatatat    360
cctgtgacca cactacttga acatgatgct gttcagttgt tcaaccaata cgccttcaaa    420
gatgaagttc cagataagtg tttcgaggag atgacgttgg aggtagtacg tcatgctcaa    480
ggccttcctc tcgccctcg                                                  499

<210> SEQ ID NO 31
<211> LENGTH: 455
<212> TYPE: DNA
<213> ORGANISM: Nicotiana tabacum

<400> SEQUENCE: 31
tcaaataaat tgcatggacc cattagagct tcaaggaata aaaacttctt tgcaaaactt     60
caaattatgg atctttcatc caatgcattt agtgggaatt taccagcagg ccttttgag    120 aaattccaat cgatgaaact aattgataag agcatgagta cactttggta ttggagtgca    180
aatgtacaaa ttgcatctaa tttgatattt acaacaaagg gattgacact tgaatttcct    240
cgagttttga atactagtaa catggttatc gatctctcaa ggaatagatt tgaaggttgt    300
attccaagta ctattggagg tctcattgga cttcgtacgc tgaacttatc tcacaatggc    360
ttggagtgtc acataccacc atcactgcaa catctatctg ttcttgaatc attggatctc    420
tcatttaaca aaattggtgg agaaatacca caaca                               455

<210> SEQ ID NO 32
<211> LENGTH: 401
<212> TYPE: DNA
<213> ORGANISM: Nicotiana tabacum

<400> SEQUENCE: 32
tcaaataaat tgcatggacc tattccaaag tcactcctaa accagcataa tctattagca     60
cttctccttt ctcaaaataa tctcagtgga cagattgctt caaccatctg caatcttaaa    120
acagtgcagt tgctaggtct gggaagtaat aatttacagg gaacaatccc agaatgtttg    180
ggtgagatgg atagaactta tgttttggat ttaagcaata ataattttag tgggacaatt    240
caagcaaatt ttagtattgg aaaccgattc agagtcatta aattgcatgg gaataagtta    300
gagggaaaag tcccaagatc tttgatcaat tgcaagtatt tggaactact tgatttaggt    360
aacaatgagt tggacgacac ttttccaaaa tggttgggaa t                        401

<210> SEQ ID NO 33
<211> LENGTH: 320
<212> TYPE: DNA
<213> ORGANISM: Nicotiana tabacum

<400> SEQUENCE: 33
tcaaataagt tgcatggtcc cattccagtg tcaataggaa acatgacgtc tcttattgat     60
cttgaattaa gcggaaatcg cctagttggt aagataccaa gagagttggg acagctaaag    120
aatttgaaac tccttgaact ttattacaac caactcgaag gtcaaatccc cgaggagctt    180
ggaaatttaa ctgaacttat agacttggat atgtctgtta acaatttaac aggcaaagtt    240
```

```
ccggagtcta taagccgcct tcctaagcta gaagttttgc agctttacca taattctctt    300
tcaggagaga taccacaaca                                                320

<210> SEQ ID NO 34
<211> LENGTH: 556
<212> TYPE: DNA
<213> ORGANISM: Nicotiana tabacum

<400> SEQUENCE: 34
tcctattaaa acttcaagga ctggaaactt gtttgcacag ctttaagtta tggatctatc     60
atccaatgga tttagtggca atttacctgt aagtctttt gtgaatttgc aagccatgaa    120
gaaaattgat gagaacatga tagggaaaga gattttagat tatgatgatt ctttgacaat    180
tacaacaaag ggattggatc ttacttttgc tagagttttg tggagaaata acatagttat    240
agatctctca agaaatagat ttgaaggtcc tattcctaac attataggac atctcattgg    300
acttcgtgtg ttaaagttat ctcataatgt cttggatggt catataccag catcattgca    360
aaatctattt gtactcgaat cattggatct ctcatctaac aaaatcaacg agaaatttc     420 cgcggcaact tccatccctc acatttcttg aagtcttaaa tctctctcac aatcatcttg    480
ttggatgcat tcccaaagga aaacaatttg atacatttga aacagttca taccaaggga    540 atgatggatt acgcgg                                                    556

<210> SEQ ID NO 35
<211> LENGTH: 458
<212> TYPE: DNA
<213> ORGANISM: Nicotiana tabacum

<400> SEQUENCE: 35
tcgaataagt tgcatggtcc tataaatgat tcaaggactg agaacttgtt tgctaaaatt     60
ctagtaatag atctctcatc caatggattc agtggagatt tacctgtgag ccttttttgag   120 aattttcaag ccatgaaaat gattggtgag aatagtggaa ccccagagta tgtagcagaa    180
acatattcta ctttatacac aaaattcttg atagtgacaa caagggggtt ggatcttgaa    240
cttcctcaag ttttgactac aaacataatt atcgatctct caatgaatag atttgaaagt    300
tctatcccaa gtattattgg agatctaatt ggacttcgta tgttgaactt gtctcataat    360
aacttgaaag gtcatatacc agcatcaatg caacatttat ctgtacttga atcattggat    420
ctctcatcca acaaaatcgg cggagaaaat tccacagca                           458

<210> SEQ ID NO 36
<211> LENGTH: 449
<212> TYPE: DNA
<213> ORGANISM: Nicotiana tabacum

<400> SEQUENCE: 36
tcgaataagt tgcatggacc tatcagaaca tcaaggattg agaacatgtt tccagagctt     60
cgaatcatag atctctcctc caatggcttc tcgggaaact acccacgaa tttgtttcta    120 catctgaaag ccatgaggac aattgatcca tcaatggaag caccaagtta taaacgagat    180
agatattacc aagattctat tacagttgca actaagggat gtgatcgtga aattgtgaga    240
atcttgtatt tgtacaccgt tatcgatcct tcaagtaata aatttagagg gaaaattcca    300
agtatcgtgg gggatctcat tgcagttcgc atcttgaatt tatctcataa tggattgcaa    360
ggtcatatac cgcaatcatt cggagattta tcttcagttg aatcattgga cctatcagga    420
```
aaccaacttt cgggagagat accacagca                           449

<210> SEQ ID NO 37
<211> LENGTH: 15
<212> TYPE: DNA
<213> ORGANISM: Artificial Sequence
<220> FEATURE:
<223> OTHER INFORMATION: Description of Artificial Sequence:synthetic
      primer

<400> SEQUENCE: 37
aarytntgyg ararr                                          15

<210> SEQ ID NO 38
<211> LENGTH: 15
<212> TYPE: DNA
<213> ORGANISM: Artificial Sequence
<220> FEATURE:
<223> OTHER INFORMATION: Description of Artificial Sequence:synthetic
      primer

<400> SEQUENCE: 38
rcanggraar tarca                                          15

<210> SEQ ID NO 39
<211> LENGTH: 15
<212> TYPE: DNA
<213> ORGANISM: Artificial Sequence
<220> FEATURE:
<223> OTHER INFORMATION: Description of Artificial Sequence:synthetic
      primer

<400> SEQUENCE: 39
rcarttraar tarca                                          15

<210> SEQ ID NO 40
<211> LENGTH: 29
<212> TYPE: DNA
<213> ORGANISM: Artificial Sequence
<220> FEATURE:
<223> OTHER INFORMATION: Description of Artificial Sequence:synthetic
      primer

<400> SEQUENCE: 40
ttgaattcag gmatgssrgg aktsggyaa                           29

<210> SEQ ID NO 41
<211> LENGTH: 28
<212> TYPE: DNA
<213> ORGANISM: Artificial Sequence
<220> FEATURE:
<223> OTHER INFORMATION: Description of Artificial Sequence:synthetic
      primer

<400> SEQUENCE: 41
ttctcgagtc raskgmkara ggmarncc                            28

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence:synthetic
      primer

<400> SEQUENCE: 42
ggrggaktsg gyaarackac w                                   21

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence:synthetic primer

<400> SEQUENCE: 43
raskgmkara ggmarncc                                         18

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence:synthetic primer

<400> SEQUENCE: 44
carrgcyaad ggaagtcc                                         18

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence:synthetic primer

<400> SEQUENCE: 45
gatagctaat ggcacacc                                         18

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence:synthetic primer

<400> SEQUENCE: 46
tcraataart tgcatggwcc yat                                   23

<210> SEQ ID NO 47
<211> LENGTH: 17
<212> TYPE: DNA
<213> ORGANISM: Artificial Sequence
<220> FEATURE:
<223> OTHER INFORMATION: Description of Artificial Sequence:synthetic primer

<400> SEQUENCE: 47
tgytgyggwa tytctcc                                          17

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence:synthetic primer

<400> SEQUENCE: 48
ccrcgtaayc catcattmcc                                       20

```
<210> SEQ ID NO 49
<211> LENGTH: 26
<212> TYPE: DNA
<213> ORGANISM: Artificial Sequence
<220> FEATURE:
<223> OTHER INFORMATION: Description of Artificial Sequence:synthetic
      primer

<400> SEQUENCE: 49
tctagaatgg gatttgttct cttttc                                       26

<210> SEQ ID NO 50
<211> LENGTH: 26
<212> TYPE: DNA
<213> ORGANISM: Artificial Sequence
<220> FEATURE:
<223> OTHER INFORMATION: Description of Artificial Sequence:synthetic
      primer

<400> SEQUENCE: 50
ggtaccggca cggcaagagt gggata                                       26

<210> SEQ ID NO 51
<211> LENGTH: 27
<212> TYPE: DNA
<213> ORGANISM: Artificial Sequence
<220> FEATURE:
<223> OTHER INFORMATION: Description of Artificial Sequence:synthetic
      primer

<400> SEQUENCE: 51
ggtaccacgt gcaccacctc gcagcag                                      27

<210> SEQ ID NO 52
<211> LENGTH: 26
<212> TYPE: DNA
<213> ORGANISM: Artificial Sequence
<220> FEATURE:
<223> OTHER INFORMATION: Description of Artificial Sequence:synthetic
      primer

<400> SEQUENCE: 52
agatcttcat agcgacgcac acgtag                                       26

<210> SEQ ID NO 53
<211> LENGTH: 33
<212> TYPE: DNA
<213> ORGANISM: Artificial Sequence
<220> FEATURE:
<223> OTHER INFORMATION: Description of Artificial Sequence:synthetic
      primer

<400> SEQUENCE: 53
ggatccccat gaactttcgt gctctgttcg ctg                               33

<210> SEQ ID NO 54
<211> LENGTH: 26
<212> TYPE: DNA
<213> ORGANISM: Artificial Sequence
<220> FEATURE:
<223> OTHER INFORMATION: Description of Artificial Sequence:synthetic
      primer

<400> SEQUENCE: 54
tagcgacgca cacgtagacg agaacc                                       26
```

<210> SEQ ID NO 55
<211> LENGTH: 27
<212> TYPE: DNA
<213> ORGANISM: Artificial Sequence
<220> FEATURE:
<223> OTHER INFORMATION: Description of Artificial Sequence:synthetic primer

<400> SEQUENCE: 55
ggtaccacca cgtgcacctc gtcgcag                                27

<210> SEQ ID NO 56
<211> LENGTH: 25
<212> TYPE: DNA
<213> ORGANISM: Artificial Sequence
<220> FEATURE:
<223> OTHER INFORMATION: Description of Artificial Sequence:synthetic primer

<400> SEQUENCE: 56
agatctcagc gacgcgcacg tggac                                  25

<210> SEQ ID NO 57
<211> LENGTH: 11789
<212> TYPE: DNA
<213> ORGANISM: Nicotiana tabacum

<400> SEQUENCE: 57
gaattctaat gaaagtaagt tggaagtttg gaagtgttgg gtttttaagc attaataagc      60
ttaaaacagg gtgaatgaga aattgaggga aaaattaggt tccctcttga ttgtcccata     120
tgggaagagg aaaacgtttt tgatgggtat ataagcaatt gctcttcttt tagctcttaa     180
agagttgaga agaaggcaag tctcgcgctg tcgtcgtcgt tgctcgctcg acttcggctt     240
cggatttgat caaatttatt tgttaatatt aaatattaac agaaatgtta ttaaatattt     300
tgttattaat gttattaaat atttgtttaa taacaaaata ttaatattaa atccattcaa     360
ttttcagttt tctgttgttg taatagaaaa ttaactactc ttcaattttc cctctttatt     420
gttgagtaaa tagccaatta tgtcatggca tttattctat aggcgttttg aaaaaacagc     480
ctcttcaaat ttcaactcaa acatgcatgt ttcctaggga agctctccaa aacttcaaaa     540
accttgcaac aaagaactat atgctttctt tacttgcatt tatgctattc ttttctgact     600
aaatcgatgt atatgaaggt gttgagatac gttggagtca tggatggtgt caatggaaaa     660
gcggctgtcg agctgcaaag atacaataat gaacgtccat ttgcacaatt ctcaggatcg     720
gataacataa ttgcattcac aactgaaaga catgcgaaga atctctcgta gtgtgtggtc     780
cgattgctgg agctgaattg tcttcttgtg gagtatatat taactgcatt tcagaccttt     840
gttacagtca acagtcaaca gcctgcctct actgatactg tagtctcata tgctttacat     900
ggtgttgcat ggctcactct gtggcttgtc tcttctcttc ttctgtagga cttttttgta     960
gcctgcttat ttgttaaatt gcaactctga tattgattaa gttgtatttt ggttgaaatc    1020
agttagtgaa gcaagattgg tgatgtatgt tgatgcatca tcaacgactc tatagtgttc    1080
atatggtcga cttcaagtct gtaactctct tgagattgag gcataatgtt gttatttta     1140
cgtaaaaata aggtgtacat ttggttcttt ttatttagtt gtttgatttt taattttgaa    1200
agaaaataaa tccatttcga agtaaaatag atttggtttg attcaatttt ctttttttaa    1260
ttttcttcga attgattttt tgggttttcc attatcaagc aaatgatgta gctggtaagg    1320
ctgagtacaa tataccgggc tgcctttttt ttatatgaag gtgttgagat acgtcggagt    1380

-continued

```
cgtggatgtt gtcaatggaa aagcgactgt ccagctgcaa agagacaata acgaacgccc    1440
atttgcacaa ctgtcaggat cggataacat aattgcattc ataactgaaa gacatgtgaa    1500
gaacctctag tagtgtgtgg tctggttgct agggcttaag taatagcttg tggagtattt    1560
tgtgacatct tgcgacttgc atcatatatt ggtgctccat cttaatattc atttagtgca    1620
aggcagtccg atgcactaag ctccagctat gtgctgggtc cgaagaacgg tcgaaccaca    1680
aggatctata atactcagtc ttaccctgca tttctgcaat ttgtttccac tgctcgaact    1740
cgtgacctct tggtcacatg gcatcaactt taccggtcac gccaaggctc cccttcaatt    1800
actgcaagcc agtattttgc ttcttttttt ttagtaccaa gttctaaact ttgttgtatg    1860
attttcatgt ggaaagatgt atttggtgtt aaggttgtaa ttcaattatt aacttcattt    1920
ttcattacca agtttcagac ctttgatatg ccacactgta gtctctatgc tttacatggt    1980
gttgccgttt aagcaacaac atgcatgctc actctgtggc ttgtctcttc tcttcttcta    2040 taatttttt tttttttgt tagctttctt atttaatttg taaattgcaa ctctgatatt    2100
gattcaagcc tgctcccagg gtcagcagcg aggtaagctc catctccttt ttcctttgtc    2160
tttttctact gttcatcctt gaccttcttt ctgaactcgt taacaccgga acacccgcca    2220
tgaaggttac tcaaagtaac ctactcgagc ttcgcccttt gtatataagt tgtattttgg    2280
ttgaaatcag ttagtagagc agattagtga tgtatgttga tgcagcatcc aatggactgt    2340
atagtgttcc tataaccgac tgtaagtctg taagactgta actctcttga gattgaggcg    2400
taattattgt tatttgtaac taaaaataag gtgtacattt ggttctttat gattttaatt    2460
ttgaaagaaa ataaatccaa cctgaagtaa aatagatttg gtttggttca attttctttt    2520
ttgatttttt tcgaattgat ttattgggtt tttcattatc aagcaaaata atatctatag    2580
caaaaccata aaaagagttc ataaaaaaaa acacacacat gggagaaaaa actgttcaaa    2640
atccgtaaaa tattccagta taatatattg gtccaacata atatgctgga agttcaagtg    2700
atccaatctc tagtatacta tgctggaact ttccgtgttg aagcaaaata gtagtctttt    2760
ttcaatatac tagaactttc cgtgttgcag caaaatagta gtaattattt ttcaatgact    2820
ttgcaaacgc ttcatatttt tcaattacca gtcttaaaac tagtaattac aaggtaatat    2880
acttaattag ttgattcttc tattgccatt ttgcatagaa ttaagtagac atagtatttg    2940
gactttggag caataattct attcaacttg gcattttatt ttctttattt attcatcagc    3000
ttgtactttt agctgcccat tgtgtacatc ttacagtgga cctttggtgc aggggaattt    3060 gtgggggtg gggtggggg gtgggagga atttcctaat acattctatt aaatacagtt    3120
caaagaaaac ccacaataaa caatagttct aatcaacggg agtagagatt aagaatcttc    3180
acagaaattt catactactt ctattaataa tttcaaaaat aatgtaccac atataatgct    3240
atataaatat atttcagttg actagatcca atagcaataa ttttattcaa ctggagtaga    3300
gcccatcgcc ttagaagctt tcatatttga agtgtatttg cttattcttc tgaagtacag    3360
acactctata atagtatccc tatataacac cacttcacta taaatccaa gattttcga    3420 aaccaatttt tatgttacgt tataatatat gtgctctata acagcacttc gctataacat    3480
ccaaaaatat ttggaacaaa cgaggctgtt atatagaggt ttgactgtat caataagctg    3540
atctcttacc acgactacaa tatatccaca cagtttttt ttgttttcat atcaaccaat    3600
taattgaatc catggcatct tcttcttctt tcgcgagtaa ttcacaatac tatcctcgat    3660
ggaagtacga tgtttttccag aggtgaagat actcgcaaaa cgtttacagg gcacttatat    3720
gaaggcttga gaaatagagg aatatttacc tttcaagatg acaaaaggat agagaatggc    3780
```

```
gaatccatct cagaaaaact ttgtaaagct atagaagagt ctcaagttgc cgtcatcatt    3840
ttctcaaaga attatgctac atcgaggtgg tgcttggatg aactagtgaa gatcatggaa    3900
tgcaagactc aatttgaaca aactgtcata ccggtcttct atgatgtgga tccatcaaca    3960
attcgatacc aaaagcaaag ctttgctgaa gccttttaca acatgaatc aaagtttaag     4020 gatgatgttg agggaatgca gaaggtacaa agatggagga gtgctttaac tgaagcggca    4080
aatctcaaag gctgtgatat tcgtgacagg tgagttaaaa acacattagc tggaacagag    4140
agaatacttt gcattcaaat ttggatgctt ctatgaagac tagctacaca tattctatac    4200
ctcaaaaatg agttacacag aatccttaaa taaatttttc atattttcta aaagaagatt    4260
gatggttgat tatatatgat tctataagta agaagacata acttatcagt ttaattactc    4320
aattatattg ttatgtagat actattttga ttggttcttc aagagtttga tttctgtgtc    4380 cttttttatca taattatgca ctatatggtt gactttctta cctgtatata tcaacaatgt   4440 aattttgta ggattgaatc agactgtgtt cagcagatcg ttgaccaaat ttccaagtta     4500
tgcaagtttt ctttatcata tttgcaagat attgtgggaa taaatccata tttagagaaa    4560
gtaaaatcct actacagata gaaatcaatg atgttcatat tgtggggatt tggggcatgg    4620
gaggagttgg taaaacgaca atagcaagag ccattttga tacactctcg tatcaatttg      4680
aagttacttg cttccttgcg gatgttaaag aaaacaaatg tggaatgcat tctttgcaaa    4740
atatccttct ctcagaactg ttaagggaaa acgctaatta cgtgaataat aaggatgacg    4800
gaaagcatct gatggcttgt agacttcgtt ctaagaaggt tttagttgtg cttgatgaca    4860
tagatcactg agaacatttg gagtacctag caggggatct tggttggttc ggcaatggca    4920
gtagaattat tgcaacaaca agagacaagc atttgattgg gaagaaggat acattatatg    4980
aagtgactac actagctgac catgaagcta ttcgattgtt caatcgatac acttttaagg    5040
aagatgttcc agatgagttt tttgagaagc taacgctgga ggtagtaagt catgctaaag    5100
gccttccttt agcgctgaaa gtgtggggtt ctttcttca taagaggaat ataactgagt    5160
ggagaagtgc tatactgcaa atgaaaaaac actctaattc agaaattgtt gacaagctca    5220
aaattagcat gcttcttacg agggagagaa aaggatgaga tcatacagat tcttgagagc    5280
tgtgattttg gggttaatat cggattgcgt gtcctaattg acaaatctct tgtgtttatc    5340
tccgaaaaag atacgattga aatgcatgac ttaataaaag atatgggtaa atatgtagta    5400
aacatacaaa agaatccggg agaacgtagc agactatggc tcgccgaaga tttcgaagaa    5460
gtgatgatca acaatacagt aagtaggctt tactgcagta atattcaatt tctattttc     5520 atattccaaa gacatagagg ctcagttaat caattatatg ttcttcttgc ttcttattct    5580
cgcacgtaag tcatttaat tgtttgtttt aataagagaa aaaaagtaa cattaattgc      5640 cgtcaagtag gcacttaca tagtgttgcc taatccgttg tacttattaa gccatgaatt     5700
agtctagtag ccacttaatc tttttaatcc atcattcttc tgattaactt gaatttgtt     5760 accattgaat atttttcaag ttaaaaaact gctacaattt attggtattt tttcaattaa    5820
ttgttctatc attgcatgaa aaactttact cgactctaaa gaagttctca gaaaatatat    5880
tattactgac atttgaagct atactttgta agctaatgat cttttaccca ggggactaag    5940
gcaatggaag caatttggtt tctttattta aaaggactat gttttagcag agagggcatg    6000
aaaaatatga aaagacttag aatattatat atacgtgatg ggtcacaaag gatccaggct    6060
ggctccattt gccataatgg ctccattgag tatttgccca acagcttgtg ttggtttgtc    6120
```

```
tggttttgct atccttggga gtcattacca tctacatttg aacccaaaaa gctcgttcat   6180
cttaaactcc aatccagttc actgcgtcat ttatggacgg aaataacagt ataatacctg   6240
aattctactt tattttatt tttctctcta actatcttta tcctttatta atgagcgaat   6300
aatattgctt tcacctgttt tatgtttgtc ctagaattat gatgcacgtc tttacataaa   6360
aatggttatt aatttcataa gctggagcaa tggtaaagtt atcttaggtt caaaccgtgg   6420
aatcagtcat tgatgcttgc atcagggtag actatataca tcacatcctt aggggtgcgg   6480
gccttccccg ccacctgtgt gaatgcagga tgcttcgtga tcctggttgc cccttaattc   6540
cataaactca aatttatgta ttttatttta ttttgggttg ttctcagagt attactctgg   6600
catctttatg tccttgtttt ctaaatcttc tcatcatcat tttaactaaa aagctcaata   6660
aactcattca aacattttct gaacagcatt tgccgtctct aaaaaagcta attctcagtt   6720
gctgtgtaag cctgatgcga acaccagatt tcacgggat gccaaatttg gagtatttgg    6780
atttgagtct ttgcagtaat tttgaagagc ttcactactc cctgggatgt tgcagaaaac   6840
tcgtcgagtt aaatttgact tggtgtgaac gccttaagag ggttccatgt gttaacgtgg   6900
aatctcttga acatttggaa ctacatggtt gctctagttt acagaaattt ccagaaatga   6960
aaacctttt atctattcag taccaaactc atattaccaa tctagacttg agcttttag     7020
aaaaccttgt aactcttgta aaacggcact gtgttaaaac aaaaaatctg aaaacgaaaa   7080
gaaatattcc gagtccacaa tttccttgtg tgtccttaag aattttaacc ccctcacaag   7140
ttgccaaggt aatggattaa atcctcccag gatgaaacgg aataaaccct cctgcaacag   7200
tggcaataca agctgcagga taccgacgaa ctcaaagaac ggagaaaaat cacacttacg   7260
aatttgagag agagggagag actgcgaaga agaatgcagt attcagaagt tgattttcag   7320
tgaatgaaat ggaaggcatg cctcagaatc tataggcaat tattggaaga ggtgtgtctg   7380
ttcaggaaga tgtgtctgtt cagaagggaa aggtctgttc agaagggaaa ggtctgttca   7440
gaagggaaag gtgtgtctgt tcaggaagat gtgtctcttc agaagggaaa gcaaacgttc   7500
agctggattc caggattcca gttaatttcg ttaatgaact gactgacatt taattaatta   7560
ttaaataatt aactaaataa attttgtcca aaaaataatc ttatcgatcg atcatttgac   7620
aaatccaaat ccgaattcat tctcttcaac tccttttaag agctctaaga agtgatctta   7680
tatttataca cataagtgta gtttgtcttt caccaatatg gtacaaagtt catgacaaaa   7740
gcttacttga ttcaaatttt catttctctc tattttattt cccaccattt cccaattcac   7800
actcttagtc tttaaagccc aatgctctta aaatccaaca acttttccaa gcagcatctg   7860
taggttgaaa aatttggtta gtctagatgt gtcgttttgc tacagactta aaagcttacc   7920
taaagagata ggagatttag aaaacttgga gaaacttgat gccagcaata ccctaatatc   7980
acggcctcca acttccatcg tccgcttgaa caaacttaac tccttgactt ttgcaaaata   8040
agaatcagat aatggtcaag ttgcagctta ctttgtgttc cctcccgtgg ctgaagggtt   8100
acagtcattg gaatttctga aactcagtta ctgcaatcta ataggtggag gacttccaga   8160
agacattggc tgcttatatt ctttgaaaga gttgtatctc aggggaaatt attttgagca   8220
tttgcctcaa agcatggctc aactcggtgc tcttcgatcc ttggacttat cgtattgtta   8280
taggcttaaa gagttgccag atttcatggg gatgccaaac ttggaaactt tgaatctatt   8340
atattgtatg aatcttgaag agattcctca ttccacggga gttttttaaaa agctcaccga   8400
attaaatttg actgattgtg aacgccttaa gagggttcca actctgtgga tcgattccct   8460
taaatgtctg cagctacaga aatgctctag tttagaatat tttcctgata tcctcggaag   8520
```

-continued

```
catgaaattg gagttagaga ttctcatgct agacagtgta ataagggatc ttaattcgtc    8580
ctataattcg tttcaactta ccttgtatca gaatgacatc tctatttcag attccttgtc    8640
acaaagagtg tttaccattt tgcataaagg gaagaggatt ccaagttggt tccacattca    8700
gggaatggat agtagtgtat cagtcaattt gcttgaaaat tggtacggta acttcttggg    8760
atttgctgta tgttactctg gctgcttaat cgacaccaca gcccacttgg ttccattttg    8820
taacgatgga atgtcgtgga ttaccctgga actatatttt ttcgaccatt cagaatgtga    8880
tgaagaatct actgttcatt ttttctttgt accttttgct agtttatggg atccatctaa    8940
ggcaaatgga aaaacaccaa atgactatgg tcttattacg ttatctttt ctggagcaat     9000 gattgagttt ggacttcgtt tgttgtataa agatgaacct gagattgagg ccttgttaca    9060
aatgagggaa aataatgacg agtcaacaga aaattgcact aggataagga ggagcagaca    9120
tgacaacgcg accaatgaag ccagttgctc ctctggtaag aaacaaaggt cacattctat    9180
tattcagggc agctctgtct tgagaatct gcagcagcaa gtagagtcgc cagtctcttc     9240
agaaattttg aggcttaatc gttcattccc ataattttc ctagttggcg gtgaaattgt     9300
gttctctctt tttatgtaat tctctccttc tatatattag ctactgtctt cttccaaatc    9360
aataaacatt ttatttctca ttctttctta tttttccctt tttgttgttt ttctttcccc    9420
tattgacagg agctcatcaa tgggtgatgt acatatcaac aaggagtttt gtctattgtt    9480
tctccacctt gtctccgttt gtgctgaccc atgctttacc atggtgagtt aaaggatgtg    9540
aacaagtatt aattttccat gctcaaatca gattcttgaa tgttagctta aagtcactag    9600
taaactctaa aatgaaaaca taattctaca aactaaaggt gataatgctc gattgtgctg    9660
cattagttat ggacttcgtt ttcctccatg aagtaaaatt ttggtgagtt tttcaggaga    9720
atgcatctgc tgaggagttt atgcgacagt tggctaacca aaggcaagag actgaagctg    9780
ttgacgaagt gagatataga ataaacttaa acgttacaga tacatactat tgtgatggcc    9840
atcttatccg aaagaaccta ctctcgtata ctctccgttt gaaactgatg ttcaccttca    9900
cttgcaaaat aatttgcatt ttggaagaac cagaagtttc ttacacatta cataacttta    9960
agacgactca atttaacgct tcttttgag atggaagaga gaagcgttaa attgagtcgt    10020
cttaaagtcg tcaatttaac gcttctgcat ccaaatactt tcttgtcaaa aggtaatgat   10080
catgttctaa ccgtagcaat acacttttgt agagaccatt ttcatattta taccaagtta   10140
aaggaggttc aattcaggat agagggagta caagaacatt ttataaaata aacaactgta   10200
gtaaagaaaa ccataaaata tatgtatttt tctcattagc agttcctgca tagggaaatt   10260
gctctttatt ttagaatttt aatagcagaa gtaccagata agtcatagta tgtagtgccg   10320
tgcttcatca ttgactactg atttgatcca atctttgagg gagaaagtga gatgagaggg   10380
aaagaagtca caagaattat ctttgtgtga ttcaatctag ttcagttgca gccattgcat   10440
gacaaaatat tttcttgtca caaggttgag taggtcataa gcatgtatta gatgttttgt   10500
tttcttgtat ttgtgctatt ttaccttcct ttaccatttg gcggttgaaa acaaaagtga   10560
ttccagtaca cgactgttag gctcatccaa ggcgtatcta cgaaagtaat agggaacttg   10620
accgttaagt ttggaaaaag ttggccaagc ctgtgtcact ttcttacgtc aggagaaacg   10680
gcgatcaaag gagtatggga ccgatacgcg aaggatcaaa tcatagggat accggatctt   10740
aagagacgga agaaacctc ggcgacccaa agattgcgga gccgcgcccg tgccgaaagt    10800
gaagaacctt tcctcctttc agtcgagcat acccgcgctt tagcacttcc cttcccgaag   10860
```

-continued

```
taggagtagg agaaaggaaa gcgcactcga tcatttacca tgccgtatcg taagacaaaa    10920
agtcacttgc aggagcttaa aaccaatatc ttggtgaaag gcctctactc tacgaaccac    10980
agctttcttt tttgatccct cggtagcatt tcctttcact gaggaatggg cggatgaata    11040
gattcaggtg ctcctaattg atgtatatga aggtcttgag atacgttgga gtcgtggatg    11100
ttgtcaatag aaaaggagcc gtcgagctgt ggagatacag tagaaacaca gttttgcaca    11160
actctcacga taggataaca taattgcatt cacaattgaa agatatgcga agcaacctct    11220
attagtgtgt ggtttcgtgt cctggggctg aagtgacagc ccgtggagta ttctgtgact    11280
tgttgctact tgagtcatgt gttgatgctt catcataatt catttactga aagctagttt    11340
tctgcttttc tgagtaccaa gtttcagatt ttgtctttgt tgtactgatt ttcatgtgga    11400
aagacatatt tggtgttaag gttgtagttc aattattaac tgtatctgtt tccctgatcg    11460
tttcgtgtct ttctgcagac gtatactcta cggataaaaa tttcactgtg gtactagatg    11520
aagatgcctt tgaggttctt ctcacaagtc cacacagaaa attggcaaag ggttgttatt    11580
cccaaaggta gctactgatc catgagttta aacttttta atttatcgtt ttgatgctct    11640
ctttgaggag tatattggag gaaactctgc tttaaattca gatatctctc ttgttgtggc    11700
aggaaggttg ggaaaatgat gaaaaagtcg acgatgcagc acaacatgag acagtggagg    11760
aagctggagc gcaaggtgaa gttgaattc                                      11789
```

<210> SEQ ID NO 58
<211> LENGTH: 932
<212> TYPE: DNA
<213> ORGANISM: Nicotiana tabacum

<400> SEQUENCE: 58

```
ggccattatg gccggggatc ataactcgaa ctagctaact ttagttattg agagacaaac      60
aaattacaga agcttaatta attattagag aaagagagat ggaaggtgct tatatcggtt     120
gccatattct caccgttttt cttattatag ctgtcttcac atcttcttca ttcacggagt     180
cagtttcagc ggcaaggcca gcagccggag atacaaatac ggagtttata agaacatcat     240
gcaaatcaac tacatatcca aacctctgtt tcagttcatt atcaggccgt gcaactgcta     300
ttggggtttc ccctcaactt ctagcccatg aatccctcac cgtcagcctc gaaacagcgc     360
agtctacatc tgtcacgatg gtggagttgg cacacggcca aggcatgacg ccgagagaga     420
tcggtgccat gcatgactgt gtggaggaac taagcgacct gtcgttgaat tgagaaagtc     480
tttgggcgaa atgaagcagc taaggggcaa agatttgacc ttaaaatgag tgatattcaa     540
acgtgggtaa gtgctgcttt gactgacgag gacacctgca ccgagggggtt tgccggaaaa     600 gttatgaacg ggaaagttaa gacagtagta aggggaagga ttctggacgt tgcacatttg     660
acaagtaatg ccttggcttt gatcaacagc cttgccgctt ttcacggcta gagcaagaag     720
tcaattacac gtacactcct atatagtgtt atttctcgtt tttctcaaag tgtacttagt     780
tcttcctttg ctgatccctg aagtagcagg gtcgtcagct ttgggtaatt ttcttatata     840
agtctgttcc atatgcattt atagaaaagg taattttgt gcaaaaaaaa aaaaaaaaa     900 aaaaaaaaaa acatgtcggc cgcctcggcc ca                                   932
```

<210> SEQ ID NO 59
<211> LENGTH: 124
<212> TYPE: PRT
<213> ORGANISM: Nicotiana tabacum

<400> SEQUENCE: 59

```
Met Glu Gly Ala Tyr Ile Gly Cys His Ile Leu Thr Val Phe Leu Ile
 1               5                  10                  15

Ile Ala Val Phe Thr Ser Ser Phe Thr Glu Ser Val Ser Ala Ala
             20                  25                  30

Arg Pro Ala Gly Asp Thr Asn Thr Glu Phe Ile Arg Thr Ser Cys
         35                  40                  45

Lys Ser Thr Thr Tyr Pro Asn Leu Cys Phe Ser Ser Leu Ser Gly Arg
     50                  55                  60

Ala Thr Ala Ile Gly Val Ser Pro Gln Leu Leu Ala His Glu Ser Leu
 65                  70                  75                  80

Thr Val Ser Leu Glu Thr Ala Gln Ser Thr Ser Val Thr Met Val Glu
                 85                  90                  95

Leu Ala His Gly Gln Gly Met Thr Pro Arg Glu Ile Gly Ala Met His
            100                 105                 110

Asp Cys Val Glu Glu Leu Ser Asp Leu Ser Leu Asn
        115                 120
```

<210> SEQ ID NO 60
<211> LENGTH: 3612
<212> TYPE: DNA
<213> ORGANISM: Nicotiana tabacum

<400> SEQUENCE: 60

```
tgtgaagttt ccaattcagt gctgttcttg gagttgtgac aagttcttgt tagtgttgga      60
ttggattgct gttgtggtta acttgaaatt tccaatttct tataaatttt gcggtaatga     120
gtgatggaat gatggaaata gagaagcccg taaatgttga ttcaaagtgt gacaaacaat     180
ggtttgtaga tgccagtact gaacaggagg agccatgtgt cgagaggctt aattttaaaa     240
ctttagatgg tgtagaatta gattgttgtg ccacgaatca tgccactaat tgtgcaaccg     300
aagctgtaga tggtgtagga gtagaatgtt gtgccacgaa tcgtgcaccc gaaactgtag     360
atggtatagg agtagaaggt tgtgccacga atcgtgcacc tgaaactgaa gatgatgtag     420
aattagaagg ttgtgccgcg tttcgtgcac ctggaacttt aaacacggag gaatcagagt     480
taggtgagaa gcaggcaaac aaattgaata attgtgatgt ccagccctat gtaaggattg     540
atgtgaagga agcttcgaat gatgagatgc tttctgaagt tcaaatcca aatttgtctc      600
caagagagaa cacgtcaagt ttccagacta tcagtaatca agggatggat ttattgagta     660
ataatcaagg ttgttctgga gagattacat cttttcatc agggaattca agtgcggatg      720
agagtgtcgg tgaagaagag cataatcaaa ttgatgtatc cgaggcagtt gcgaaatcct     780
ctgtggtact tgaaattcca aaggaattta gcacaactgg tgtcaggaag attacattta     840
agtttagcaa agaaaggag gattatggta atgcatatgc ttcagctgct ctgcctgtga      900
ctgatcgggt tgatgatgga tttggtgaag cacatgcatg gtatccttct gatgatatga     960
ctcaccgtat ttcaagcaca aatggagcat tttatcaaca tggagatcct tttttatgtc    1020
ctccaaacat ggaattaaaa atgtctaaga aggtcatttc tgatgcttac ccgacaaatg    1080
tcaagaagct tctatcgacg ggtatttggg aaggagcaag ggtgaactac atttcaactt    1140
ctgggaagat ggagcttcct ggaatcataa aggattacgg atacttgtgt ggttgttcat    1200
tctgcaattt ctctaaagtt tcagtgctt acgaatttga agtgcatgct gggggcaaga     1260
ctagacaccc aaacaatcat atttatttgg agaatggaaa acctatttac aggataattc    1320
aagagttgaa gactgcacca cttagcagac tagaagaagt tgtaagagac gtggctggtt    1380
```

```
                                    -continued
cttctattaa tgagcaatat tttgaggctt ggaaagcaaa actcctgcag tgctatgagg   1440
tggctagtgc tgaccaatat tcttatggaa aggcttcagg aatttatcac tctaagctaa   1500
gttcggtgat ggaagatggc cttatttctg cttcctactc ctatattgac aacttccctc   1560
caaatccatt tagctatatg gagacagcag aggcatggaa gcatgtggct aaaaagccaa   1620
ggtgcaattt ttccagctca acagtagagc caaaaagacc tgctgaaggt tgcacaagaa   1680
aaagggataa tgacttgcac cgatcattat tcatgccaaa tggacttcca gatggaactg   1740
atttggcata ttattctaag gggaagaaag ttctgggggg ctacaagctg gaaatggca    1800 tagtctgcag ctgctgtgat actgagataa gtccgtccca gtttgaggct catgctggat   1860
gtgcagctaa acgtcagcct taccgtcaca tctacacttc caatggactt accctacacg   1920
atatagcatt aatgctggca atggtcaaa gtattgccac caataacagt gatgatatgt    1980
gtacaatatg cggcgatggg ggagaactga tttgctgtga agggtgtcct cgggctttcc   2040
atgcagcttg tttaggtgta cagtgtaccc caaccagtgg ttggctctgt tcatattgta   2100
gagacaattt tgtacctggt aggaaaactg caggagatgc aggaccaatt atgatacggt   2160
tgacaagagt ggttaaagct ccggagtctg aaggtggtgg gtgcgttgtt tgcaggaccc   2220
cggactttag cgttgccaaa tttgacgatc ggacagttat gctctgtgac cagtgtgaga   2280
aagaatacca tgttgggtgt ctgcgggaaa gtgggctgtg tgatctgaaa gaactcccaa   2340
aagataaatg gttttgttgc aatgactgca ataaagttta tgcggtactt cagaattgtg   2400
ttctgaaggg agctgaggtc attccagcac ctgcagcaac tgcagtaact aagaagcatg   2460
tccagaaatg tttaatggat acagctacaa atgacattca gtggcgaatc ttaagtggga   2520
agagtcgcta cccggagcat ctacctcttc tttccagagc agcaacaatc tttagggagt   2580
gctttgatcc tattgttgcc aaatctggac gagatcttat acctgttatg gtttatgggc   2640
gaaacatctc gggtcaggaa tttgggggaa tgtattgcat cgttttgact gtaaagtctg   2700
tagtcgtatc agctggtctt ctcaggattt tcgggcaaga ggttgctgaa ctacctttgg   2760
tggctacaag tagagaaaac caagggaaag gttatttcca ggcgttatttt gcatgtattg   2820 agatgctatt atcttccatg catgttaaaa acctggttct gcctgctgct gaggaggcgg   2880
aatccatctg gacaaataaa ctggggttca aaaagatgac tgatgaacga tatctgaagt   2940
attcaaggga cttccagttg acggtattca agggacatc aatgttggag aaggaggtgc    3000
agcagacagc ttatgaattg taattcatct ttgtggagaa tgtgcaacaa ggagctagaa   3060
ttgctacata tcttgcacgc actctcattc aggagggaga cctctgttct actcaatgat   3120
ctgaaatgga agtgaaaata gagaaagagg tgcttctcat tgcagatcga tcttttctt    3180 aatatctaga acatgcaaaa tgcacctatg ctgatgagtt ttgagtttca aggcgattaa   3240
atagtagaca atgcaaggtg tttggaggca catcaagttg ctggcggacc ttgtagcgat   3300
cactcttaga tgcaaggaca agtgcatttc ttattcgtta tttaccacta tgttttcata   3360
aagtagtcat tgctttttata gattagtttt cagctgatgt ataaagagca gctgaggaac   3420
tgctcgttga aagtcctcga ggcatgctga ccttttatca tgcgtgcgtg gggcaaacgt   3480 tgttttttacc ccttctttt tgcagtggta gtttcctttt gtacatttcc agtgcataaa   3540
aaaaaaagaa aaaaaaaaa agtcgacatc gagacgcgtg tcgggctag agcggccgcc     3600 accgcggtgg ag                                                      3612

<210> SEQ ID NO 61
<211> LENGTH: 20
```

```
<212> TYPE: DNA
<213> ORGANISM: Artificial Sequence
<220> FEATURE:
<223> OTHER INFORMATION: Description of Artificial Sequence:synthetic
      primer

<400> SEQUENCE: 61
taagcctctc gacacatggc                                                   20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence:synthetic
      primer

<400> SEQUENCE: 62
tcggttgcac aattagtggc                                                   20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence:synthetic
      primer

<400> SEQUENCE: 63
cgattcgtgg cacaacattc                                                   20

<210> SEQ ID NO 64
<211> LENGTH: 19
<212> TYPE: DNA
<213> ORGANISM: Artificial Sequence
<220> FEATURE:
<223> OTHER INFORMATION: Description of Artificial Sequence:synthetic
      primer

<400> SEQUENCE: 64
tggtcaaagt attgccacc                                                    19

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence:synthetic
      primer

<400> SEQUENCE: 65
gggggagaac tgatttgctg                                                   20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence:synthetic
      primer

<400> SEQUENCE: 66
ttaggtgtac agtgtacccc                                                   20
```

METHOD OF IDENTIFYING NON-HOST PLANT DISEASE RESISTANCE GENES

CROSS REFERENCE TO RELATED APPLICATIONS

This application is a divisional of U.S. application Ser. No. 09/387,286, filed Aug. 31, 1999 now U.S. Pat. No. 6,544,733 which is a continuation-in-part application of U.S. provisional patent application No. 60/098,402, filed on Aug. 31, 1998, which is herein incorporated by reference in its entirety.

FIELD OF THE INVENTION

The present invention relates to a new method to rapidly identify genes that function in non-host resistance. It also relates to genes identified by this method that enhance levels of disease resistance if expressed in susceptible plants.

BACKGROUND OF THE INVENTION

Genetic diversity is an important factor in the balanced evolution between plants and their pathogens. In natural systems, outbreeding plant populations interact with mixed pathogen populations. This interaction is often dependent on the presence of resistance (R-) genes in the plant and avirulence (avr) genes in the pathogen. The outbreeding plants share pools of R-genes, and the plant pathogens produce a variety of elicitors, directly or indirectly produced by the avr genes. Individual plants that contain R-genes that somehow recognize one of the elicitors produced by an infecting pathogen are resistant against this pathogen.

R-gene mediated resistance usually results in a hypersensitive response (HR), observed as rapid necrosis at the infection site. Apparently, the activated R-gene triggers a signal transduction event leading to apoptotic cell death, which may prevent the invading pathogen from spreading beyond the infection site and trigger resistance in non-infected adjacent cells.

Over the last five years, a number of R-genes have been cloned. The most ubiquitous class of R-genes encode proteins with a C-terminal leucine rich repeat, an N-terminal nucleotide binding site, and a conserved stretch of amino acids with the consensus sequence GLPLAL. Examples of this class of R-genes are Rps2 (Bent et al., 1994), N (Whitham et al., 1994), L6 (Lawrence et al., 1995), M (Anderson et al., 1997), and Rpm1 (Grant et al., 1995). Progress has also been made in the identification of proteins involved in R-gene mediated signal transduction. Recent papers report the involvement of protein kinases, putative transcription factors, and lipase-like proteins in R-gene signalling (reviewed by Innes, 1998). Recently, it has been shown that the engineering of these signaling components may also lead to enhanced levels of disease control in plants (Cao et al., 1998).

It is believed that R-genes do not provide protection against all genotypes of a pathogen, i.e., pathogens within a species do not all produce the same elicitor. It is therefore likely that infections of outbreeding populations will result in the survival of part of the population only. Modern agriculture may likely disturb the balance between plants and pathogens. Outbreaks of a disease that several decades ago would impact a relatively limited number of plants can now cause devastating epidemics.

To prevent major losses to diseases, plant breeders attempt to introgress resistance against the most important pathogen races into elite cultivars. In most cases, this is a never-ending battle because resistance against one or several genotypes of a pathogen will select for occurrence of other genotypes. For example, the subsequent introgression of eleven R-genes from the resistant wild potato species *Solanum demissum* into cultivated susceptible potato cultivars resulted in all cases in the emergence of virulent genotypes of the pathogen *Phytophthora infestans*. Classical breeding is by definition based on crossing programs and, therefore, can only transfer resistance traits between different accessions or cultivars of the same plant species or between plant species that are sexually compatible. This resistance is often referred to as "host" resistance. Temporal control of many pathogens including the following have been obtained by introgression of R-genes: *Phytophthora infestans, Phytoplitliora megasperma, Puccinia graminis, Puccinia recondita, Puccinia sorghi, Puccinia coronata, Puccinia helianthi, Puccinia striiformis, Erysiphe graminis, Ustilago hordei, Ustilago avenae, Uromyces phaseoli, Peronospora farinosa, Pseudomonas syringae, Xanthoinonas oryzae, Cladosporium fulvum*, brown plant hopper, aphids, hessian fly, and tobacco mosaic virus.

A few R-genes have been identified that provide resistance against most races of a particular pathogen. Of particular interest are the rice Xa21 gene that controls most races of *Xanthomoas oryzae* (Mazzola et al., 1994; Song et al., 1995), the wheat Lr34 gene involved in resistance to most leaf rusts, and the barley Rpg1 gene that protects plants against almost all stem rusts. However, these R-genes are rare and may be broken by new aggressive races.

A superior source of resistance that provides broad-spectrum and durable disease control but is unaccessible to classical breeding is the so-called "non-host" resistance. A plant species displays non-host resistance if all sexually compatible accessions and cultivars of that particular species or very related species are resistant to all genotypes of a particular pathogen. Due to the lack of susceptible material within those plant species, it is impossible to determine the genetic basis of non-host resistance.

To date, no genes have been cloned that are known to be involved in active non-host resistance. However, it is possible that such genes resemble the R-genes isolated from sources displaying host resistance. Support for this hypothesis comes from studies on the interaction between *P. infestans* and the non-host plant species *Nicotiana tabacum* (tobacco). The resistance of tobacco correlates with its ability to respond with an HR to infection, suggesting that the resistance of tobacco against *P. infestans* is based on an active defense mechanism controlled by R-genes (Kamoun et al., 1997). Thus, the non-host resistance of tobacco appears to be "active", and is different from "passive" resistance that is based on factors such as the presence of preformed pathogen inhibitors or the absence of factors that are essential for pathogen growth (Ride, 1985).

It can be envisioned that expression of certain cloned non-host resistance genes in susceptible crops would provide the broad-spectrum and durable disease resistance levels that are needed in modern agriculture. However, it is impossible to isolate non-host resistance genes through genetics-based methods. Here, the inventors have developed a new technique based on the isolation and screening of large numbers of genes that are associated with active non-host resistance. The screening is performed in plants that are both susceptible to certain target pathogens and highly accessible to transformation. By implementing this technique, a number of genes have been identified that enhance, or are expected to enhance, levels of disease resistance if expressed in susceptible plants.

SUMMARY OF THE INVENTION

The present invention relates to a method to screen genes associated with non-host resistance for those genes that enhance levels of resistance if expressed in susceptible plants, by transforming tissue of a pathogen-susceptible plant with these genes, challenging the transformed tissue with a pathogen or its elicitor, and observing enhanced defense and/or HR responses. In a particular embodiment of the invention, homologs of R-genes from tobacco are identified by gene amplification, cotransformed with the INF1 elicitor of *Phytophthora infestans* into leaves of *Nicotiana benthamiana*, and screened for the presence of a hypersensitive response, which indicates functionality. In another embodiment, genes associated with non-host resistance are identified by first selecting genes that are induced by target pathogens in the non-host but not (or not as much) in susceptible hosts, and second screening them for their ability to enhance resistance against a model pathogen such as the bacterial pathogen *Pseudomonas tabaci* if transiently overexpressed in leaves of *N. benthamiana* plants.

In one aspect, the present invention provides novel nucleic acid sequences (SEQ ID NO:57 and SEQ ID NO: 1–10 and SEQ ID NO:58, 60, 62) that can confer disease resistance to *Phytophthora infestans* to plants. A further embodiment of the invention provides novel protein sequences (SEQ ID NO: 11–20 and SEQ ID NO:59) involved in disease resistance to *Phytophthora infestans* in plants.

In a further embodiment of the invention, plant cells or transgenic plants comprising a nucleic acid sequence conferring enhanced resistance to *Phytophthora infestans* are provided as well as seed or progeny from such plants. A transgenic plant, seed, or progeny thereof that comprises a nucleic acid sequence of SEQ ID NO:57 displays resistance to disease from or a hypersensitive response in response to *Phytophthora infestans* or other fungal pathogens as compared to an otherwise similar plant lacking the nucleic acid sequence. A transgenic plant, seed, or progeny thereof that comprises a nucleic acid sequence of SEQ ID NO:60 displays resistance to disease from or a hypersensitive response in response to *Phytophthora infestans* or other fungal pathogens as compared to an otherwise similar plant lacking the nucleic acid sequence. Also provided are related methods of producing a transgenic plant exhibiting enhanced resistance to fungal pathogens comprising introducing into a plant cell a nucleic acid sequence encoding an R-protein thereby producing a transformed cell, and regenerating a transgenic plant therefrom that displays resistance to a selected fungal pathogen or pathogens as compared to an otherwise similar plant lacking the nucleic acid sequence.

The present invention also encompasses the use of any of the DNA sequences or biologically functional equivalents thereof disclosed herein to produce recombinant plasmids, transformed microorganisms, probes, molecular markers, and primers useful to identify related nucleic acid sequences that confer resistance to fungal pathogens on plant cells and to produce transgenic plants resistant to such fungal pathogens.

The foregoing and other aspects of the invention will become more apparent from the following detailed description and accompanying drawings.

LB=left border; RB=right border; P-35S=35S promoter of cauliflower mosaic virus; NPT=neomycin phosphotransferase gene, ocs3'=termination sequences of the octopine synthase gene; P-FMV=35S promoter of figwort mosaic virus; sp=sequence encoding the signal peptide of PR1a; nos3'=termination sequences of the nopaline synthase gene. Figure is not to scale. The orientation of the HindIII-XhoI DNA fragment containing INF1 may be reversed.

FIG. 2 provides a representation of the plasmid map for pMON 11770.

FIG. 3 shows the alignment of deduced partial amino acid sequences of 10 R-gene homologs involved in enhancement of INF1-induced HR (SEQ ID NO: 11–20).

FIG. 4 provides a representation of the plasmid map for pMON17227.

Figure 1:
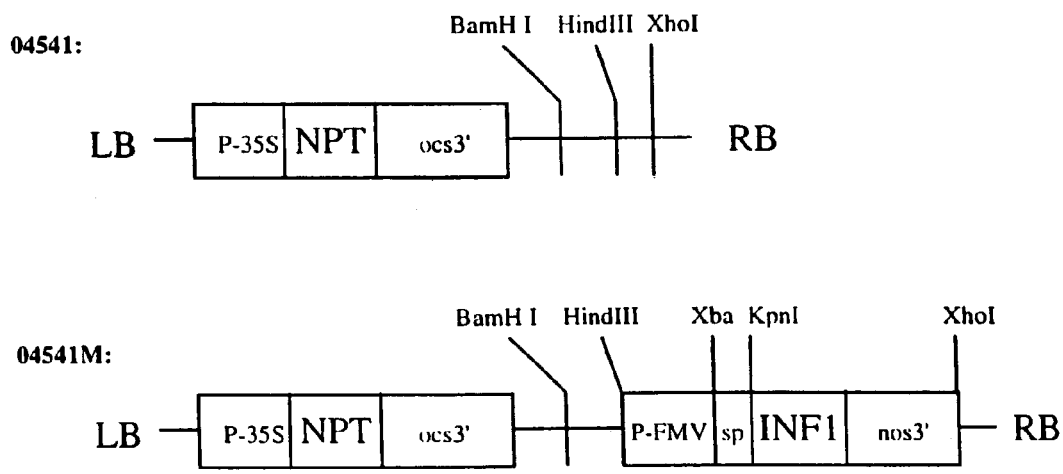
FIG. 1 represents the T-DNA structures of binary cosmid vectors 04541 and 04541 M.
Figure 5:
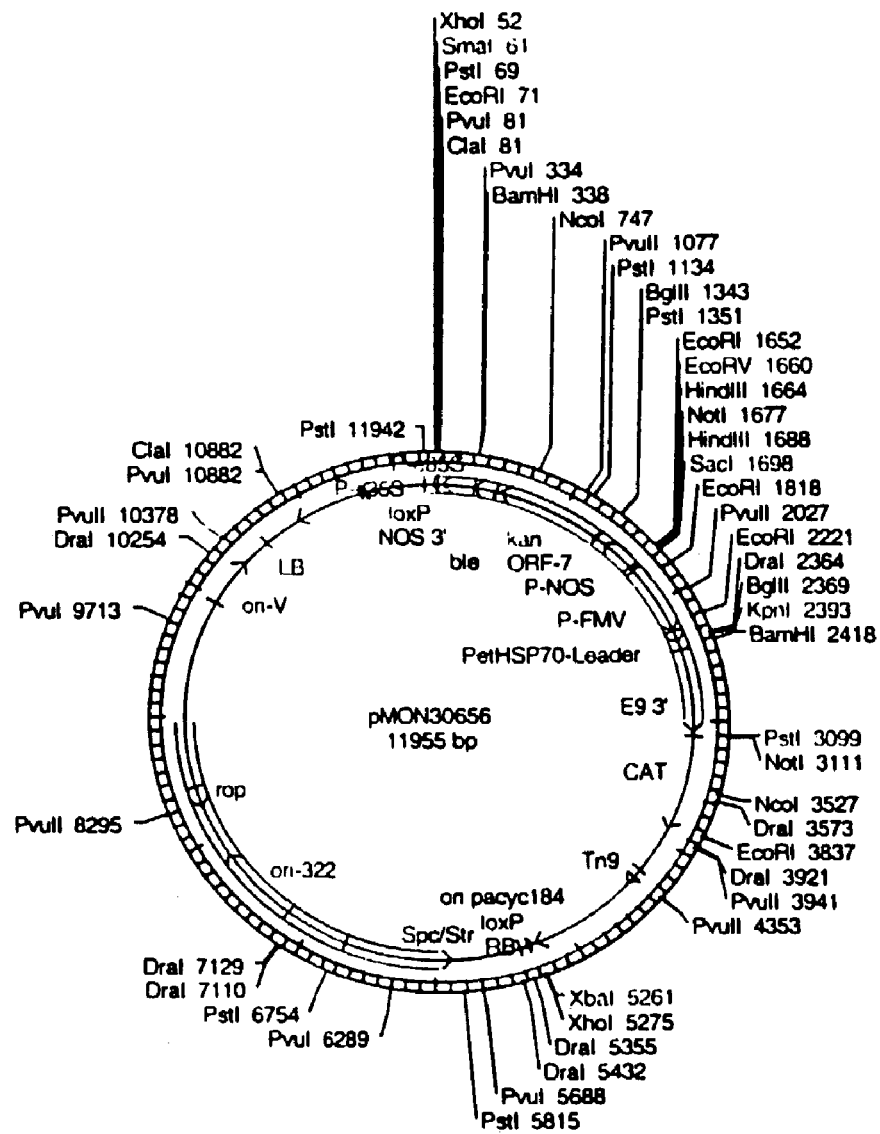

FIG. 5 provides a representation of the plasmid map for pMON30656.

Figure 6:
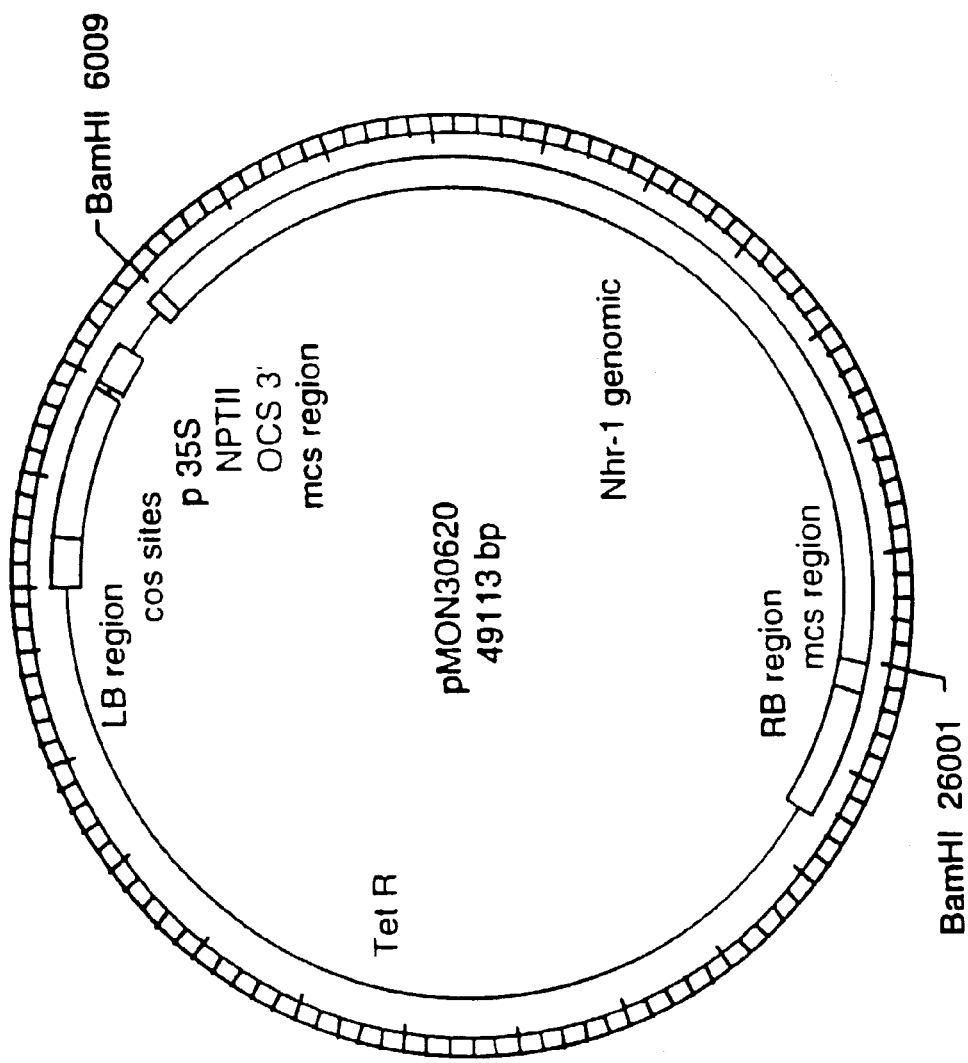

FIG. 6 provides a representation of the plasmid map for pMON30620.

Figure 7:
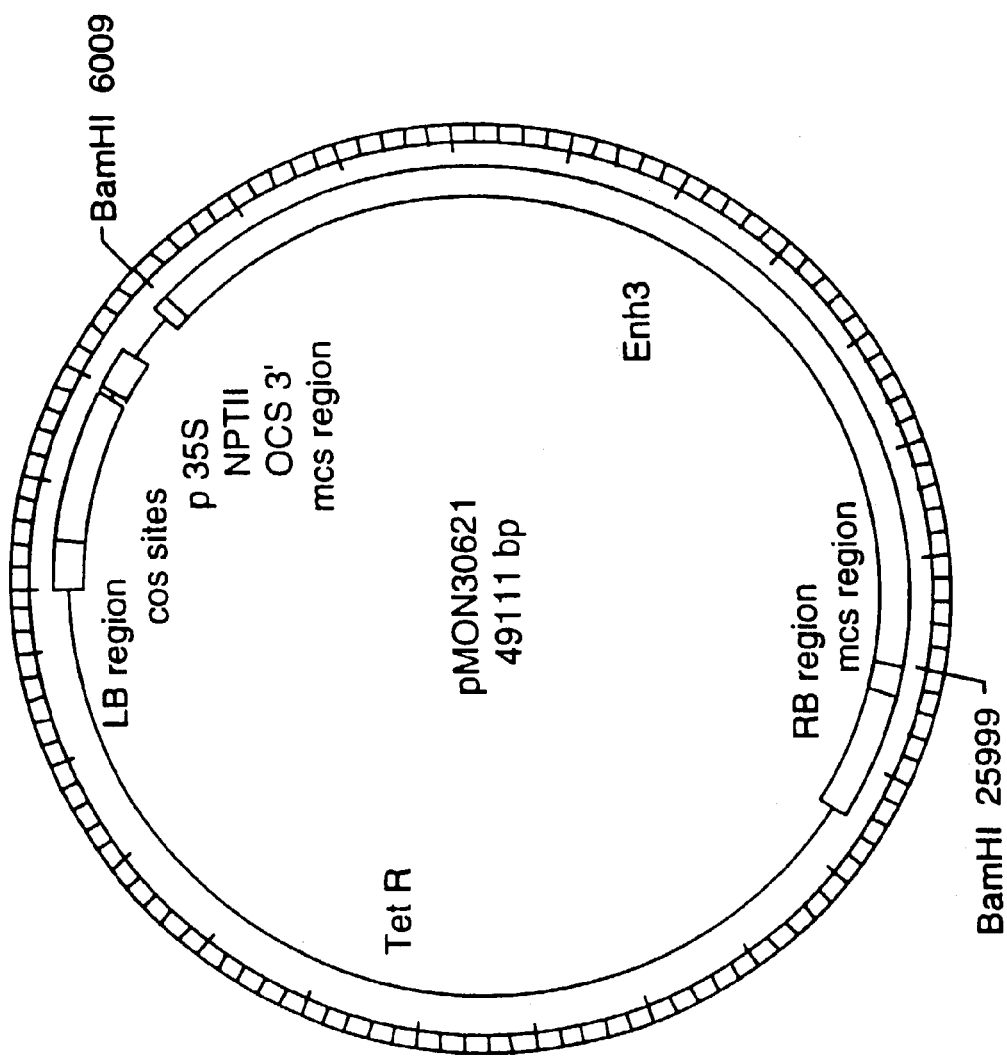

FIG. 7 provides a representation of the plasmid map for pMON30621.

BRIEF DESCRIPTION OF THE SEQUENCES IN THE SEQUENCE LISTING

SEQ ID NO: 1–10 show partial sequences of tobacco R-gene homologs that enhance the INF1-dependent HR in *N. benthamiana*.

SEQ ID NO: 11–20 are the deduced partial amino acid sequences of R-gene homologs (SEQ ID NO: 1–10) involved in enhancement of INF1-induced HR.

SEQ ID NO:21–30 are sequences that represent 10 different subclasses of class I R-gene homologs.

SEQ ID NO:31–36 are sequences that represent 6 different subclasses of class II R-gene homologs.

SEQ ID NO:37–39 are primers used to isolate antimicrobial peptide homologs.

SEQ ID NO:40–45 are primers used to isolate class I R-gene homologs.

SEQ ID NO:46–48 are primers used to isolate class II R-gene homologs.

SEQ ID NO:49–50 are primers used to isolate the signal peptide of the PR1a gene.

SEQ ID NO:51–52 are primers used to clone the INF1 gene into a binary cosmid vector.

SEQ ID NO:53–54 are primers used to clone the INF1 gene in a pGEX vector.

SEQ ID NO:55–56 are primers used to isolate the elicitor of *P. sojae*.

SEQ ID NO:57 is a genomic sequence representing the Enh3 gene.

SEQ ID NO:58 is the DNA sequence of TOB-F12.

SEQ ID NO:59 is the protein sequence of TOB-F12.

SEQ ID NO:60 is the DNA sequence of the Nhr1 gene.

SEQ ID NO:61–66 are primers used to isolate the Nhr1 gene.

DETAILED DESCRIPTION OF THE INVENTION

Definitions

In order to provide a clear and consistent understanding of the specification and the claims, including the scope given to such terms, the following definitions are provided.

A plant disease resistance (R-) gene is a nucleic acid isolate encoding a protein that is directly or indirectly involved in the induction of a signal transduction pathway eventually leading to a plant defense response against any pathogen or insect, upon contact of the plant with that particular pathogen or insect. Resistance gene products are activated in response to pathogen signal molecules termed elicitors.

Non-host inducible genes (NHIs) are genes rapidly induced by a pathogen in a non-host plant.

An R-protein is the product encoded by an R-gene.

A plant disease resistance (R-) locus is a genetically defined locus involved in insect or disease resistance that is known or believed to contain at least one functional R-gene.

An R-gene homolog is a DNA sequence with predicted amino acid sequence that has significant homology with one or more previously isolated R-genes. It should contain both a nucleotide binding site and a GLPLAL region.

Significant homology is defined as a DNA sequence that hybridizes under conventional hybridization conditions with a reference sequence. Preferably the hybridization conditions refer to hybridization in 6×SSC, 5× Denhardt's solution, 100 mg/mL fish sperm DNA, 0.1% SDS, at 55° C. for sufficient time to permit hybridization (e.g., several hours to overnight), followed by washing two times for 15 min each in 2×SSC, 0.1% SDS, at room temperature, and two times for 15 min each in 0.5–1×SSC, 0.1% SDS, at 55° C., followed by autoradiography. Typically, the nucleic acid molecule is capable of hybridizing when the hybridization mixture is washed at least one time in 0.1×SSC at 55° C., preferably at 60° C., and more preferably at 65° C.

An R-gene subclass consists of a group of R-gene homologs that share over 70% identity at the amino acid level or cross-hybridize on plant genomic Southern blots.

A functional R-gene is a gene encoding a protein involved in a plant resistance response against a pathogen or insect.

An R-gene source is a plant that displays disease resistance to one or several pathogens of interest and is likely to contain R-genes mediating this resistance. Indications for the presence of active R-genes are (1) resistance is associated with a hypersensitive response and (2) resistance is dependent on the presence of a single locus.

R-gene signal transduction pathways are pathways that can be activated by specific pathogen elicitors through direct or indirect interaction with R-gene products and that, upon activation, often trigger a hypersensitive response, induction of pathogenesis-related gene expression, and disease resistance.

The hypersensitive response (HR) is one plant defense against pathogens. It encompasses a rapid cellular necrosis near the site of the infections that correlates with the generation of activated oxygen species, production of antimicrobial compounds, and reinforcement of host cell walls. Pathogens that elicit an HR on a given host are avirulent on that host, the host is resistant, and the plant-pathogen interaction is incompatible.

Host resistance refers to any disease or insect resistance of a cultivar, ecotype or accession that is a member of a plant species that contains at least one other cultivar, ecotype, or accession that does not display this resistance.

Non-host resistance refers to any disease or insect resistance that is shared among all cultivars, ecotypes, or accessions of a particular plant species and sexually compatible related plant species.

Active non-host resistance is non-host resistance known or believed to be based on the activation of defense responses upon infection. Active non-host resistance is not based on (1) the absence of factors essential for pathogen differentiation or growth, (2) the presence of preformed inhibitors of pathogen growth, (3) any other "passive" reasons.

A non-host resistance gene is an R-gene, NHI or gene that encodes an elicitor-binding protein that was isolated from a non-host and enhances plant HR and/or defense responses in a susceptible host.

An elicitor is a molecule or peptide produced by a pathogen that triggers a response in a plant. Production of elicitors is controlled by pathogen avirulence genes.

A plant system refers to a plant species that can be used to screen members of multigene families via transient transformation.

Expression means the combination of intracellular processes, including transcription and translation, undergone by a coding DNA molecule such as a structural gene to produce a polypeptide.

A promoter is a recognition site on a DNA sequence or group of DNA sequences that provides an expression control element for a structural gene and to which RNA polymerase specifically binds and initiates RNA synthesis (transcription) of that gene.

Regeneration is the process of growing a plant from a plant cell (e.g., plant protoplast or explant).

A structural coding sequence refers to a DNA sequence that encodes a peptide, polypeptide, or protein that is made by a cell following transcription of the structural coding sequence to messenger RNA (mRNA), followed by translation of the mRNA to the desired peptide, polypeptide, or protein product.

Stable transformation is a process of introducing an exogenous DNA sequence (e.g., a vector, a recombinant DNA molecule) into a cell or protoplast in which that exogenous DNA is incorporated into a chromosome or is capable of autonomous replication.

Transient transformation is a process of introducing an exogenous DNA sequence carrying one or several genes driven by promoters and followed by termination signals into a cell or protoplast with the purpose of expressing the introduced genes for a limited amount of time.

A transformed cell is a cell whose DNA has been altered by the introduction of an exogenous DNA molecule into that cell.

A transgenic cell refers to any cell derived or regenerated from a transformed cell or derived from a transgenic organism. Exemplary transgenic cells include plant calli derived from a transformed plant cell and particular cells, such as somatic cells (e.g., leaf, root, stem) or reproductive (germ) cells, obtained from a transgenic plant.

A transgenic plant is a plant or progeny thereof derived from a transformed plant cell or protoplast, wherein the plant DNA contains an introduced exogenous DNA molecule not originally present in a native, non-transgenic plant of the same strain. The terms "transgenic plant" and "transformed plant" have sometimes been used in the art as synonymous terms to define a plant whose DNA contains an exogenous DNA molecule. However, it is thought more scientifically correct to refer to a regenerated plant or callus obtained from a transformed plant cell or protoplast as being a transgenic plant and that usage will be followed herein.

A vector is a DNA molecule capable of replication in a host cell to which another DNA segment can be operatively linked so as to bring about replication of the attached segment. A plasmid is an exemplary vector.

Plant is used herein in a broad sense and refers to differentiated plants as well as undifferentiated plant material, such as protoplasts, plant cells, seeds, plantlets, etc., that under appropriate conditions can develop into mature plants, the progeny thereof, and parts thereof such as cuttings and fruits of such plants.

Biologically functional equivalents refers to equivalents with respect to the nucleic acids and proteins of the present invention that contain a sequence or moiety exhibiting sequence similarity to the novel sequences of the present invention and that exhibit the same or similar functional properties as that of the sequences disclosed herein.

The present invention enables the isolation of non-host resistance genes for control of viral, bacterial, fungal, or nematodal pathogens including, but not limited to, *Phytophthora, Erisvphe, Puccinia, Septoria, Ustilago, Melampsora, Bremia, Venturia, Uromyces, Tilletia, Rhynchosporium, Pyrenophora, Fulvia, Fisarium orysporum, Peronospora, Pseudomonas syringae, Xanthomonas, Cladosporium, Coletotrichum*, tobacco mosaic virus, potato virus Y, potato virus X, *Phialophora, Heterodera, Colletotrichum, Magnaporthe*, brown plant hopper, green rice leafhopper, aphids, *Pseudocercosporella*, and hessian fly. It also provides DNA sequences of functional R-genes, NHIs, and a gene encoding an elicitor-binding protein, and genetic constructs and methods for inserting such DNA sequences into host cells for the production of polypeptides encoded thereby for control of *Phytophthora infestans* and possibly other species of *Phytophthora*.

The present invention teaches to express R-genes, NHIs and genes encoding elicitor-binding proteins in susceptible plants to identify genes that enhance the HR and/or defense responses. The ability to rapidly isolate such "functional" genes, and the subsequent transfer of these non-host resistance genes to susceptible crops, will greatly facilitate the development of disease resistant cultivars. Here, the inventors describe a completely new method of isolating non-host resistance genes using procedures not based on classical genetics. Instead, it relies on the screening of R-genes, NHIs and elicitor-binding proteins in plant test systems for functional activity. One of the most important consequences of this new approach is that the source of resistance is an active non-host, expected to allow the isolation of genes involved in broad-spectrum and durable disease control.

Screening for Genes Associated with Active Non-host Resistance

One skilled in the art could analyze for the presence of functional R-genes in non-hosts and thus allow a selection of useful resistance sources (R-gene donors), through a variety of methods, including, but not limited to, infecting non-hosts and examining for the presence of hypersensitive response (HR) lesions. It will sometimes be possible to observe this HR macroscopically as localized lesions. Often though, a microscopic analysis of infected leaf tissue is required. One method of visualizing HR cells is to stain with lactophenol blue. Other methods well known in the art may also be utilized for detection of plant lesions, including, but not limited to, examining for the presence of HR cells by autofluorescence. Other factors that increase a non-host's usefulness as an R-gene donor, although lack thereof is not a disqualification, include a known elicitor from the pathogen of interest.

In an embodiment of the invention, tobacco displays a durable and broad-spectrum non-host resistance against *P. infestans*, causal agent of late blight in potato. This resistance is associated with the induction of a hypersensitive response upon infection (Kamoun et al., 1997), suggesting that the resistance of tobacco against *P. infestans* is based on an active defense mechanism controlled by R-genes. The cloning of tobacco R-genes with functional activity against *P. infestans* is facilitated by the fact that the elicitor, INF1, of *P. infestans* responsible for induction of tobacco's HR has already been cloned. Injection of small amounts of the INF1 peptide into the intercellular spaces of tobacco leaves results in the induction of an HR (Kamoun et al., 1997).

In one embodiment, DNA fragments are identified and used to visualize many or all subclasses of potential R-genes that provide disease resistance associated, or believed to be associated, with HR. One skilled in the art may utilize methods well known in the art to isolate these fragments that can be used as "subclass specific probes," and include, but are not limited to, for example, (1) designing degenerate or non-degenerate R-gene primers specific for domains that are conserved among R-genes to amplify fragments of a large variety of homologs of R-genes (examples of conserved domains are the nucleotide binding site and the GLPLAL motif); (2) sequencing R-gene fragments from the genome of a resistance source and grouping them into subclasses, the preferred deduced amino acid sequence identity among members of the same subclass is greater than about 70%, and (3) hybridizing DNA fragments representative of each subclass with total genomic plant DNA digests to estimate the total number of members per subclass. Subsequently, subclass-specific probes are used to screen binary cosmid libraries of the resistance source. These libraries are constructed by partially digesting total genomic DNA and subcloning preferably the fragments from about 15 to about 20 kb and most preferably the fragments from about 21 to about 25 kb between the T-DNA borders of a binary cosmid vector that is able to replicate in both *E. coli* and *A. tumefaciens* (Jones et al., 1992).

Construction and screening of binary cosmid libraries rather than cDNA libraries is preferred because (1) the binary cosmids allow screening of R-genes without further cloning steps and (2) expression of cDNA clones of R-genes in certain cases (e.g., Rps2 and N) has been shown not to provide disease resistance against pathogens with the corresponding avirulence gene.

It is contemplated that the DNA sequence information provided by the invention allows for the preparation of DNA (or RNA) sequences that have the ability to specifically hybridize to gene sequences of selected polynucleotides. Nucleic acid probes of an appropriate length may be prepared based on a consideration of a selected sequence of an R-gene homolog such as, most preferably, sequences identical to SEQ ID NOS:1–10 or, preferably, any of the subclass-specific probes mentioned. The ability of such DNAs and nucleic acid probes to specifically visualize subclasses of R-genes in *Nicotiana, Solanaceous*, and other plant species lends them particular utility in a variety of embodiments. Most importantly, the probes may be used in a variety of assays for the isolation of functional R-genes. Homologs of R-genes can also be used to study segregation of resistance in a segregating population of plants. In this way, it may be possible to identify on Southern blots bands that cosegregate with resistance. These bands may function as tight molecular markers for resistance and may be used as such in breeding programs. Additionally, these bands may visualize the segregating R-genes themselves. Thus, the homologous sequences to R-genes presented in the examples may be useful for both the mapping and isolation of R-genes. For example, we have tested DNA fragments homologous to R-genes (SEQ ID NOS:21–36) as probes on Southern blots containing DNA of potato plants that segregate for resistance against the US-8 genotype of *P. infestans*. The radioactively labeled DNA fragment with SEQ ID NO:29 could be used to identify one band in many resistant plants that is always absent in susceptible plants.

In certain embodiments, it is advantageous to use oligonucleotide primers. The sequence of such primers is designed using a polynucleotide for use in detecting, amplifying, or mutating a defined segment of an R-gene using PCR technology. A size of at least 14 nucleotides in length helps to ensure that the fragment will be of sufficient length to form a duplex molecule that is both stable and selective. Molecules having complementary sequences over stretches greater than 14 bases in length are generally preferred, though, to increase stability and selectivity of the hybrid, and thereby improve the quality and degree of specific hybrid molecules obtained. One will generally prefer to design nucleic acid molecules having gene-complementary stretches of about 14 to about 20 nucleotides, or even longer where desired. Such fragments may be readily prepared by, for example, directly synthesizing the fragment by chemical means; by application of nucleic acid reproduction technology, such as the PCR technology of U.S. Pat. Nos. 4,683,195, and 4,683,202, herein incorporated by reference; or by excising selected DNA fragments from recombinant plasmids containing appropriate inserts and suitable restriction sites.

The screening of binary cosmid libraries yields cosmids carrying at least parts of R-genes. The presence of homologous sequences to R-genes may be confirmed by methods well known in the art, including, but not limited to, PCR amplification with degenerate R-gene primers. Those skilled in the art could use a simple method to obtain an indication for the presence of full-length R-gene homologs driven by their own promoters and followed by their own termination signals between the borders of the T-DNA. This method is based on our finding that injection of high concentrations of *Agrobacterium* strains (about 109 colony forming units/mL) carrying R-gene homologs into the intercellular spaces of plants such as *Nicotiana benthamiana* often results in the induction of an HR that is independent of either pathogen challenge or elicitor treatment, 3 to 6 days postinjection. Thus, the structural and functional sequences of R-gene homologs that induce a "spontaneous" HR in plants are most likely full length.

In another embodiment, genes can be identified that are not R-genes but function in either R-gene activated pathways or any other induced pathways that lead to pathogen resistance. These "non-host inducible genes" (NHIs) can be isolated by using techniques such as PCR select subtraction, that allows the identification of genes that are expressed upon pathogen challenge in the non-host plants but not, to a lesser extent, in the susceptible host plants. To quickly select the most interesting leads, these candidate genes can be transiently expressed in a plant such as *N. benthamiana* and tested for their ability to limit disease symptoms caused by a model pathogen such as *Pseudomonas tabaci*. Alternative pathogens that can be used for this purpose are all other pathogens that infect *N. benthamiana*, including tobacco mosaic virus, potato virus X, and *P. infestans*.

In another embodiment, elicitor-binding proteins that function in resistance signaling can be identified using the yeast two-hybrid method. Yeast two-hybrid system has been widely used to study protein-protein interactions (Fields and Sternglanz, 1994). Pathogen elicitors can be subcloned into the "bait" vector and used to isolate plant proteins that interact with elicitors. Positive candidates can then be transiently expressed in plants and test for their ability to induce HR and/or defense responses. In principle, all the pathogen elicitors and/or avirulence factors that can induce defense responses in plants can be used through this approach to isolate their plant binding/interacting factors.

To identify non-host resistance genes in a model system, this model must display (1) accessibility to transient transformation, (2) susceptibility to target and/or model pathogens, and (3) insensitivity to certain elicitors of this pathogen. One candidate plant system of high interest is *N. benthamiana*, because this plant system is highly accessible to stable *Agrobacterium*-mediated transformation (Rubino et al., 1993), accessible to transient *Agrobacterium*-mediated transformation, and susceptible to many pathogens that are fully controlled in tobacco including soybean mosaic virus, sweet potato feathery mottle virus, prunus necrotic mosaic ilarvirus, bean common mosaic poyvirus, and bacterial *Pseudomonas syringae* pathogens that carry the avirulence gene avrPto (Rommens et al., 1995). It is expected that *N. benthamiana* will also display susceptibility against other agronomically important viral, fungal, bacterial, and nematodal pathogens, including, but not limited to, *Phytophthora infestans, Phytophhtora soja, Phialophora gregata, Pseudomonas solanacearum*, and *Fusarium oxysporum*. Nematodes infecting potato, tomato, or soybean may also be included in this list, as well as certain insects. The susceptibility of *N. benthamiana* against many pathogens makes *N. benthamiana* a good plant system to screen homologs of R-genes for functional activity. Other plant systems include *N. clevelandii, N. tabacum, Lotus japonicus, Glycine max*, and *Oryza sativa*.

One skilled in the art may screen the isolated non-host genes for functional activity through a variety of methods, including, but not limited to, transforming plants with *Agrobacterium* strains carrying these genes. The plants are both highly accessible to transient, preferably *Agrobacterium*-mediated, transformation and susceptible to the target pathogens.

One way to efficiently stably transform plants with a large number of genes is by pooling *Agrobacterium* strains, each carrying a unique gene, in groups of 10. In this way, only about 50 transformations are needed. Seed can then be pooled from 40 plants per transformation. To screen for disease resistance, about 160 plants per seedlot, i.e., a total of 8,000 plants, can be infected with a pathogen.

If a target pathogen produces a known elicitor, screening efforts can be facilitated by subjecting the transgenic plants to the elicitor. Transgenic plants that express a functional non-host resistance gene will respond to this elicitor with the establishment of a clearly observable HR. Examples of known elicitors are the β-glucan elicitor released from cell walls of *Phytophthora megasperma* (Sharp et al., 1984), arachidonic acid produced by *P. infestans* (Bostock et al., 1981), the extracellular 42 kDa glycoprotein of *P. sojae* (Parker et al., 1991), and 10 kDa elicitins produced by *Phytophthora* spp. (Yu, 1995).

Transgenic plants that either display disease resistance to pathogen infection or respond with an HR upon subjection to the elicitor can be used to identify the functional non-host resistance genes in a variety of ways. For instance, T-DNA specific primers can be used to amplify part of the introduced DNA. This amplified fragment can subsequently be used as a probe to screen the original library of genes in *E. coli*. Many of the positive clones will contain the functional gene, which can then be further analyzed and subcloned according to standard protocols.

*Agrobacterium*-mediated transient gene expression, as described by Kapila et al. (1997), is an alternative to stable transformation to screen non-host genes (R-genes, NHIs or putative elicitor-binding proteins) for functional activity against target pathogens. This system is preferred if the gene encoding the elicitor of the target pathogen has been cloned. This assay has been proposed as a quick and reliable procedure to test the function of the R-genes Cf4 and Cf9 in other plant species (PCT application WO 96/35790) and to test the effect of specific mutations without the need to generate stable transgenic plants, but it has never been proposed as a method to screen a large number of genes (most preferably R-genes) for functional activity.

The methods described here are not limited to the screening of homologs for functional R-genes. In the broadest sense, members of any large family of genes can be screened for functional activity. One example of genes other than R-genes that can be screened for functional activity against microbes is the large class of genes encoding pathogenesis-related (PR) proteins. Only a small fraction of these genes have been tested for their ability to control microbes, and the method presented here would allow many more PR genes and PR gene homologs to be tested rapidly. Another example is screening for the genes encoding small antimicrobial peptides, which are present in large gene families in most or all plant species. Most of the antimicrobial peptides (AMP) contain even numbers of cysteines, which are all pairwise connected by disulfide bridges. Based on homologies at the primary structure level, plant AMPs can be classified into distinct families including thionins, plant defensins, lipid transfer proteins, and hevein- and knottin-type AMPs (Broekaert et al., 1997). The homology among AMPs may allow the isolation of AMP homologs by either gene amplification or Southern blot analysis. For example, the primers shown in SEQ ID NO:37–39 may be used to amplify large numbers of AMP homologs from genomic DNA isolated from one or several plants. Gene amplification reactions could be performed by using about 100 ng of template DNA and adding the recommended amounts of nucleotides, buffer, and Taq polymerase, together with 1 µM of primer SEQ ID NO:37 and either 0.5 µM of primer SEQ ID NO:38 or 0.5 µM of primer SEQ ID NO:39. The amplified homologs can be cloned into a binary vector that allows expression of the AMPs in planta and that can be conjugated into *Agrobacterium*. The *Agrobacterium* strains can subsequently be injected into the intercellular spaces of plant systems such as *N. benthamiana*, independently or in combinations of 2 or 3 different strains, and multiple injected leaf tissues can be tested for disease resistance simultaneously.

The gene expression systems mentioned can be used to test any other genes for functional activity against nematodes or pathogens. This includes genes involved in resistance signaling and/or defense responses and encoding protein kinases such as Pto and Pti1; transcription factors involved in defense; lipid transfer proteins; proteins involved in cell wall strengthening or lignin biosynthesis; proteins involved in early signaling; omega-6-fatty acid desaturases; GTP binding proteins involved in resistance; SAR/HR converging proteins such as Cpr5, Acd2, and Lsd1; proteins in R-gene cascade convergence pathways downstream from the HR/SAR branchpoint such as Cpr1, Cpr6, Cim2, Cim3; proteins involved in salicylic acid and jasmonic acid biosynthesis; proteins involved in phytoalexin production; proteins involved in protection against apoptosis; membrane-associated proteins involved in broad-spectrum resistance such as ml-O; proteins involved in plant stress such as chaperones; proteins involved in detoxification of microbial toxins; antifungal protein genes; putative lipases such as Pad4; and proteins induced by elicitors not mentioned above, such as cytochrome P450s, ACC synthase, and GDP dissociation inhibitor.

Cloning of Functional Non-host Genes to Confer Disease Resistance to Susceptible Hosts One skilled in the art may introduce the identified functional gene into desired but susceptible plant cultivars, through a variety of methods, including, but not limited to, *Agrobacterium*-mediated transformation. Functional genes can be used to confer disease resistance to a wide variety of plant cells, including gymnosperms, monocots, and dicots. Although these genes can be inserted into any plant cell falling within these broad classes, they are particularly useful in crops of interest, including, but not limited to, Acacia, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassaya, cauliflower, celery, cherry, cilantro, citrus, clementines, coffee, corn, cotton, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, mango, melon, mushroom, nut, oat, oil palm, oil seed rape, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, a vine, watermelon, wheat, yams, and zucchini.

Means for preparing expression vectors are well known in the art. Expression (transformation) vectors used to transform plants and methods of making those vectors are described in U.S. Pat. Nos. 4,971,908, 4,940,835, 4,769,061 and 4,757,011, the disclosures of which are incorporated herein by reference. Those vectors can be modified to include a coding sequence in accordance with the present invention.

A variety of methods have been developed to operatively link DNA to vectors via complementary cohesive termini or blunt ends. For instance, complementary homopolymer tracts can be added to the DNA segment to be inserted and to the vector DNA. The vector and the DNA segment are then joined by hydrogen bonding between the complementary homopolymeric tails to form recombinant DNA molecules.

Coding regions that encode polypeptides having the ability to confer disease resistance to a cell preferably contain sequences identical to those presented in SEQ ID NOS: 1–10 or SEQ ID NO:57 or SEQ ID NOS:58, 60, 62, 64, 66, 68, 70, or sequences that are biologically functional equivalents.

Typical vectors useful for expression of genes in higher plants are well known in the art and include vectors derived from the tumor-inducing (Ti) plasmid of *Agrobacterium tumefaciens* (Rogers et. al., 1987). However, several other plant integrating vector systems are known to function in plants including pCaMVCN transfer control vector (Fromm et al., 1985). Plasmid pCaMVCN (available from Pharmacia, Piscataway, N.J.) includes the cauliflower mosaic virus (CAMV) 35S promoter.

In some embodiments, the vector used to express the polypeptide includes a selection marker that is effective in a plant cell. The nucleic acid sequence serving as the selectable marker functions to produce a phenotype in cells that facilitates their identification relative to cells not containing the marker. Useful selectable markers include GUS, green fluorescent protein (GFP), neomycin phosphotransferase II (nptII), luciferase (LUX), chloramphenicol acetyl transferase (CAT), antibiotic resistance sequences, and herbicide (e.g., glyphosate) tolerance sequences. The selectable marker is preferably a kanamycin, hygromycin, or herbicide resistance marker. One drug resistance marker is the gene whose expression results in kanamycin resistance, i.e., the chimeric gene containing the nopaline synthase promoter, Tn5 neomycin phosphotransferase II (nptII), and nopaline synthase 3' nontranslated region (Rogers et al., 1987).

The 3' non-translated regions of the constructs of the present invention should contain a transcriptional terminator, or an element having equivalent function, and a polyadenylation signal that functions in plants to cause the addition of adenylate nucleotides to the 3' end of the mRNA. Examples of such 3' regions include the 3' transcribed, nontranslated regions containing the polyadenylation signal of *Agrobacterium* tumor-inducing (Ti) plasmid genes, such as the nopaline synthase (nos) gene, and plant genes such as the soybean 7s storage protein gene and pea ssRUBISCO E9 gene (European Patent Application 0 385 962). These elements may be combined, as an example, to provide a recombinant, double-stranded DNA molecule, comprising operatively linked in the 5' to 3' direction, a promoter that functions in a plant cell to cause the production of an RNA sequence; a DNA coding sequence that encodes an R-gene; and a 3' non-translated region that functions in the plant cell to cause transcriptional termination and the addition of polyadenylate nucleotides to the 3' end of said RNA sequence.

Gene sequences associated with resistance may comprise the entire nucleotide sequence or any portion thereof that may have functional equivalence, such as truncated versions. Alternatively, it may be desirable to express epitopic regions of the plant disease resistant polypeptides in order to use these peptides to raise antibodies against the polypeptides.

Translational enhancers may also be incorporated as part of the vector DNA. Thus the DNA constructs of the present invention should also contain one or more 5' nontranslated leader sequences that may serve to enhance expression of the gene products from the resulting mRNA transcripts. Such sequences may be derived from the promoter selected to express the gene or can be specifically modified to increase translation of the mRNA. Such regions may also be obtained from viral RNAs, from suitable eukaryotic genes, or from a synthetic gene sequence.

Such enhancer sequences may be desirable to increase or alter the translational efficiency of the resultant mRNA. The present invention is not limited to constructs where the enhancer is derived from the native 5' nontranslated promoter sequence, but it may also include nontranslated leader sequences derived from other non-related promoters such as other enhancer transcriptional activators or genes. For example, the petunia heat shock protein 70 (Hsp70) contains such a leader (Winter et al., 1988).

The present invention contemplates creating an expression vector comprising a nucleic acid sequence as described herein. Thus, in one embodiment an expression vector comprises an isolated and purified DNA molecule comprising a promoter operatively linked to a coding region that encodes a polypeptide of the present invention, whereby the promoter drives the transcription of the coding region. The coding region is operatively linked to a transcription-terminating region. As used herein, the term "operatively linked" means that a promoter is connected to a coding region in such a way that the transcription of that coding region is controlled and regulated by that promoter. Means for operatively linking a promoter to a coding region are well known in the art. Because the expression vector of the present invention is to be used to transform a plant, a promoter is selected that has the ability to drive expression in plants. Promoters that function in plants are also well known in the art. Useful in expressing the polypeptide in plants are promoters that are inducible, viral, synthetic, or constitutive (Poszkowski et al., 1989; Odell et al., 1985), and temporally regulated, spatially regulated, or spatio-temporally regulated (Chau et al., 1989). A promoter is selected for its ability to direct the transformed plant cell's or transgenic plant's transcriptional activity to the coding region. Structural genes can be driven by a variety of promoters in plant tissues. Promoters can be near-constitutive, such as the CaMV 35S promoter, or tissue-specific or developmentally specific, affecting dicots or monocots.

As discussed, the non-host genes associated with resistance can be placed under the control of either the naturally occurring homologous promoter or a variety of heterologous promoters. A number of promoters active in plant cells have been described in the literature. These include, for example, the nopaline synthase (nos), mannopine synthase (mas), and octopine synthase (ocs) promoters, which are carried on tumor-inducing plasmids of *Agrobacterium tumefaciens*; the cauliflower mosaic virus (CaMV) 19S and 35S promoters; the enhanced CaMV 35S promoter; the figwort mosaic virus (FMV) 35S promoter; the light-inducible promoter from the small subunit of ribulose-1,5-bisphosphate carboxylase (ssRUBISCO); the EIF-4A promoter from tobacco (Mandel et al., 1995); the chitinase promoter from *Arabidopsis* (Samac et al., 1991); the LTP (lipid transfer protein) promoters from broccoli (Pyee et al., 1995); the ubiquitin promoter from maize (Christensen et al., 1992); the sugarcane badnavirus promoter; and the actin promoter from rice (McElroy et al., 1990). All of these promoters have been used to create various types of DNA constructs that have been expressed in plants. See, for example, PCT International Publication WO 84/02913 in this regard. Many of these promoters may increase gene expression levels if compared to expression levels with genes driven by their natural promoters. The increased expression of genes may, in some cases, lead to an enhanced level of resistance.

Promoters useful in DNA constructs applicable to the methods of the present invention may be selected based upon their ability to confer specific expression of a coding sequence in response to pathogen infection. The infection of plants by pathogens triggers the induction of a wide array of proteins, termed defense-related or pathogenesis-related (PR) proteins (Bowles, 1990; Bol et al., 1990; Linthorst, 1991). Such defense-related or PR genes may encode enzymes involved in phenylpropanoid metabolism (e.g., phenylalanine ammonia lyase, chalcone synthase), proteins that modify plant cell walls (e.g., hydroxyproline-rich glycoproteins, glycine-rich proteins, peroxidases), enzymes that degrade fungal cell walls (e.g., chitinases, glucanases), thaumatin-like proteins, or proteins of as yet unknown function. Defense-related or PR genes have been isolated and characterized from a number of plant species. The promoters of these genes may be used to drive expression of non-host resistance genes and biologically functional equivalents thereof in transgenic plants challenged with the corresponding pathogen. For example, such promoters have been derived from defense-related or PR genes isolated from potato plants (Fritzemeier et al., 1987; Cuypers et al., 1988; Logemann et al., 1989; Matton et al., 1989; Schroder et al., 1992) or from asparagus (Warner et al., 1993). Alternatively, pathogen-inducible promoters, such as the PRP1 promoter obtainable from tobacco (Martini et al., 1993), may be employed.

Promoters may also be selected based upon their ability to confer specific expression in tissues where the plant disease resistance protein is most effective, such as in root tissues for root-specific pathogens (like soybean cyst nematodes), in leaf tissues for leaf-specific pathogens (such as rusts and mildews), or in floral tissues for pathogens that cause disease predominantly in heads (such as *Fusarium graminearum*).

In any event, the particular promoter selected to drive the expression of an R-gene in transgenic plants should be capable of promoting expression of a biologically effective amount of the protein in plant tissues. Examples of constitutive promoters capable of driving such expression are the e35S, FMV35S, rice actin, maize ubiquitin, sugarcane badnavirus, and eIF-4A promoters.

Promoters used in the DNA constructs may be modified, if desired, to affect their control characteristics. For example, the CaMV35S promoter can be ligated to the portion of the ssRUBISCO gene that represses the expression of ssRUBISCO in the absence of light, thereby creating a promoter active in leaves but not in roots. For purposes of the present invention, the phrase "CaMV35S" promoter includes variations of the CaMV35S promoter, e.g., promoters derived by means of ligation with operator regions, random or controlled mutagenesis, etc. Furthermore, promoters useful in the present invention may be altered to contain multiple enhancer sequences to assist in elevating the level of gene expression. Examples of such enhancer sequences have been reported by Kay et al. (1987).

Where the promoter is a near-constitutive promoter such as CaMV35S, increases in polypeptide expression are found in a variety of transformed plant tissues (e.g., callus, leaf, seed, and root). Alternatively, the effects of transformation can be directed to specific plant tissues by using plant integrating vectors containing a tissue-specific promoter.

An exemplary tissue-specific promoter is the lectin promoter, which is specific for seed tissue. The lectin protein in soybean seeds is encoded by a single gene (Le1) that is only expressed during seed maturation and accounts for about 2% to about 5% of total seed mRNA. The lectin gene and seed-specific promoter have been fully characterized and used to direct seed-specific expression in transgenic tobacco plants (Vodkin et al., 1983; Lindstrom et al., 1990).

The present invention contemplates not only the full-length R-gene sequences but also biologically functional equivalent nucleotide sequences. The phrase "biologically functional equivalent nucleotide sequences" denotes DNAs and RNAs, including genomic DNA, plasmid DNA, cDNA, synthetic DNA, and mRNA nucleotide sequences, that encode peptides, polypeptides, and proteins exhibiting the same or similar biological activity as that of sequences partially presented in SEQ ID NOS:11–20 or SEQ ID NO:59 when introduced into host cells in a functionally operable manner so that they are expressed, and they produce peptides, polypeptides, or proteins that are involved in the induction of an effective resistance response in plants.

Biologically functional equivalent nucleotide sequences include nucleotide sequences encoding conservative amino acid changes within the fundamental amino acid sequence, producing silent changes therein. Such nucleotide sequences contain corresponding base substitutions compared to nucleotide sequences encoding the wild-type gene.

In addition to nucleotide sequences encoding conservative amino acid changes within the fundamental polypeptide sequence, biologically functional equivalent nucleotide sequences include nucleotide sequences containing other base substitutions, additions, or deletions. These include nucleic acids containing the same inherent genetic information as that contained in the cDNA. Such nucleotide sequences can be referred to as "genetically equivalent modified forms" of the cDNA and can be identified by the methods described herein.

Mutations made in the cDNA, plasmid DNA, genomic DNA, synthetic DNA, or other nucleic acid encoding the non-host resistance gene preferably preserve the reading frame of the coding sequence. Furthermore, these mutations preferably do not create complementary regions that could hybridize to produce secondary mRNA structures, such as loops or hairpins, that would adversely affect mRNA translation.

Although mutation sites can be predetermined, it is not necessary that the nature of the mutations per se be predetermined. For example, in order to select for optimum characteristics of mutants at a given site, random mutagenesis can be conducted at the target codon.

Alternatively, mutations can be introduced at particular loci by synthesizing oligonucleotides containing a mutant sequence, flanked by restriction sites enabling ligation to fragments of the native cDNA sequence. Following ligation, the resulting reconstructed nucleotide sequence encodes a derivative form having the desired amino acid insertion, substitution, or deletion.

In either case, the expressed mutants can be screened for desired pathogen activity by, for example, the methods described in Examples 5 and 6.

Specific examples of useful genetically equivalent modified forms of the DNA include DNAs having a nucleotide sequence that exhibits a high level of homology, i.e., sequence identity, to the DNA. This can range from about 70% or greater sequence identity, more preferably from about 80% or greater sequence identity, and most preferably from about 90% or greater sequence identity, to the DNA or corresponding moiety thereof.

Such genetically equivalent modified forms can be readily isolated using conventional DNA-DNA or DNA-RNA hybridization techniques (Sambrook et al., 1989) or by amplification using PCR methods. These forms should possess the ability to confer resistance to fungal pathogens when introduced by conventional transformation techniques into plant cells normally sensitive to such pathogens.

The fragments and variants of the non-host resistance gene may be encoded by cDNA, plasmid DNA, genomic DNA, synthetic DNA, or mRNA. These nucleic acids should possess about 70% or greater sequence similarity, preferably about 80% or greater sequence similarity, and most preferably about 90% or greater sequence similarity, to corresponding regions or moieties of the DNA having the nucleotide sequence encoding the plant R-gene, or the mRNA corresponding thereto.

In the present invention, nucleic acids biologically functional equivalent to the non-host resistance gene or fragments thereof include (1) DNAs having a length that has been altered either by natural or artificial mutations such as partial nucleotide deletion, insertion, addition, or the like, so that when the entire length of the sequence is taken as 100%, the biologically functional equivalent sequence has a length of about 60% to about 120% of that sequence, preferably about 80% to about 110% thereof; or (2) nucleotide sequences containing partial (usually about 20% or less, preferably about 10% or less, more preferably about 5% or less of the entire length), natural or artificial mutations so that such sequences code for different amino acids, but wherein the resulting polypeptide retains the plant disease resistance activity of the gene. The mutated DNAs created in this manner usually encode a polypeptide having about 70% or greater, preferably about 80% or greater, and more preferably about 90% or greater sequence identity to the amino acid sequence of the plant resistance protein encoded by the nucleotide sequence.

In the present invention, the methods employed to create artificial mutations are not specifically limited, and such mutations can be produced by any of the means conventional in the art.

For example, the cDNA may be treated with appropriate restriction enzymes so as to insert or delete appropriate DNA fragments so that the proper amino acid reading frame is preserved. Subsequent to restriction endonuclease treatment, the digested DNA can be treated to fill in any overhangs, and the DNA religated.

Mutations can also be introduced at particular loci by synthesizing oligonucleotides containing a mutant sequence flanked by restriction sites enabling ligation to fragments of the native cDNA or genomic sequence. Following ligation, the resulting reconstructed sequence encodes a derivative having the desired amino acid insertion, substitution, or deletion.

Alternatively, oligonucleotide-directed site-specific or segment-specific mutagenesis procedures can be employed to produce an altered cDNA or genomic DNA sequence having particular codons altered according to the substitution, deletion, or insertion desired.

Exemplary methods of making the alterations described above are disclosed by Ausubel et al. (1995); Bauer et al. (1985); Craik (1985); Frits Eckstein et al. (1982); Osuna et al. (1994); Sambrook et al. (1989); Smith et al. (1981); and Walder et al. (1986). Biologically functional equivalents to the DNA sequences disclosed herein produced by any of these methods can be selected for by assaying the peptide, polypeptide, or protein encoded thereby using the techniques well known to the art.

Biologically functional equivalent forms of the DNA encoding an R-gene include nucleotide sequences that encode peptides, polypeptides, and proteins that react with, i.e., specifically bind to, antibodies raised against a non-host resistance gene and that exhibit the same or similar biological activity as the polypeptide. Such antibodies can be polyclonal or monoclonal antibodies.

Due to the degeneracy of the genetic code, i.e., the existence of more than one codon for most of the amino acids naturally occurring in proteins, other DNA (and RNA) sequences that contain essentially the same genetic information as the DNA of the present invention and that encode substantially the same amino acid sequence as that encoded by the nucleotide sequence of the non-host resistance gene can be used in practicing the present invention. This principle applies as well to any of the other nucleotide sequences discussed herein.

Biologically functional equivalent forms of the DNA contemplated by this invention also include synthetic DNAs designed for enhanced expression in particular host cells. Host cells often display a preferred pattern of codon usage (Campbell et al., 1990). Synthetic DNAs designed to enhance expression in a particular host should therefore reflect the pattern of codon usage in the host cell.

In the present invention, sequence similarity or identity can be determined using the "BestFit" or "Gap" programs using the default values of the Sequence Analysis Software Package, Genetics Computer Group, Inc., University of Wisconsin Biotechnology Center. Madison, Wis. 53711. The preferred scoring matrix is PAM250.

It should be understood that the present invention also contemplates nucleotide sequences that hybridize to the sequence of isolated non-host resistance genes and their complementary sequences and that code on expression for peptides, polypeptides, or proteins having the same or similar biological activity as that of native. Such nucleotide sequences preferably hybridize to the non-host resistance gene or its complementary sequence under conditions of moderate to high stringency (see Sambrook et al., 1989). Exemplary conditions include initial hybridization in 6×SSC, 5× Denhardt's solution, 100 mg/mL fish sperm DNA, 0.1% SDS, at 55° C. for sufficient time to permit hybridization (e.g., several hours to overnight), followed by washing two times for 15 min each in 2×SSC, 0.1% SDS, at room temperature, and two times for 15 min each in 0.5–1× SSC, 0.1% SDS, at 55° C., followed by autoradiography. Typically, the nucleic acid molecule is capable of hybridizing when the hybridization mixture is washed at least one time in 0.1×SSC at 55° C., preferably at 60° C., and more preferably at 65° C.

The nucleotide sequences described above are considered to possess a biological function substantially equivalent to that of the resistance encoding gene if they encode peptides, polypeptides, or proteins having an anti-pathogen effect similar to that of the nucleotide sequences identified herein.

Methods and compositions for transforming a bacterium, a yeast cell, a plant cell, or an entire plant with one or more expression vectors comprising a non-host resistance gene are further aspects of this disclosure. A transgenic bacterium, yeast cell, plant cell, or plant derived from such a transformation process or the progeny and seeds from such a transgenic plant are also further embodiments of the invention.

Means for transforming bacteria and yeast cells are well known in the art. Methods for DNA transformation of plant cells include *Agrobacterium*-mediated plant transformation, protoplast transformation, gene transfer into pollen, injection into reproductive organs, injection into immature embryos, and particle bombardment. Each of these methods has distinct advantages and disadvantages. Thus, one particular method of introducing genes into a particular plant strain may not necessarily be the most effective for another plant strain, but it is well known which methods are useful for a particular plant strain.

Methods for transforming dicots, primarily by use of *Agrobacterium tumefaciens*, and obtaining transgenic plants are well known in the art and have been published for cotton (U.S. Pat. No. 5,004,863; U.S. Pat. No. 5,159,135; U.S. Pat. No. 5,518,908), soybean (U.S. Pat. No. 5,569,834; U.S. Pat. No. 5,416,011; McCabe et al., 1988; Christou et al., 1988), Brassica (U.S. Pat. No. 5,463,174), peanut (Chenget al., 1996; McKently et al., 1995), papaya (Yang et al., 1996), and pea (Grant et al., 1995; Schroeder et al., 1993; De Kathen and Jacobsen, 1990). The field is reviewed by Gasser and Fraley (1989).

Transformation of monocots using electroporation, particle bombardment, and *Agrobacterium* has also been reported. Transformation and plant regeneration have been achieved in asparagus (Bytebier et al., 1987), barley (Wan and Lemaux, 1994), maize (Rhodes et al., 1988; Gordon-Kamm et al., 1990; Fromm et al., 1990; Koziel et al., 1993; Armstrong et al., 1995), oat (Somers et al., 1992), orchardgrass (Horn et al., 1988), rice (Toriyama et al., 1988; Zhang and Wu, 1988; Zhang et al., 1988; Battraw and Hall, 1990; Christou et al., 1991; Park et al., 1996), rye (De la Pena et al., 1987), sugar cane (Bower and Birch, 1992), tall fescue (Wang et al., 1992), and wheat (Vasil et al., 1992; Weeks et al., 1993). Techniques for monocot transformation and plant regeneration are also reviewed in Davey et al. (1986) and Davey et al. (1989).

The work described herein can be used to isolate functional R-genes, NHIs and/or elicitor-binding proteins, and to transfer these genes to crops of interest to develop insect or disease resistance.

EXAMPLES

The following examples further illustrate the present invention. They are in no way to be construed as a limitation in scope and meaning of the claims.

Example 1

Identification of Tobacco R-Genes for Potato Late Blight Control

The isolation of R-genes from the tobacco genome and the subsequent transfer of these genes to potato may allow the generation of transgenic potato plants resistant to *P. infestans*. The cloning of tobacco R-genes with functional activity against *P. infestans* is facilitated by the fact that the elicitor, INF1, of *P. infestans* responsible for induction of tobacco's HR has already been cloned (Kamoun et al., 1997). To assist in visualizing the HR cells, a preferred method is to boil the infected leaf tissue in a solution containing 1 part of lactophenol blue (0.5 mg/mL trypan blue, 0.25 g/mL phenol, 25% glycerol, 25% lactic acid) and 2 parts of 96% ethanol, followed by overnight destaining in 2.5 g/L chloral hydrate (Shipton and Brown, 1962).

To isolate parts of R-gene homologs, primers were designed that anneal to regions conserved among R-genes. Class I R-genes encode proteins with a nucleotide binding site and a conserved stretch of amino acids with the consensus sequence "GLPLAL". Primer set 1 for class I genes consisted of the primers shown in SEQ ID NOS:40–41. Primer set 2 for class I genes consisted of the primers shown in SEQ ID NOS:42–43. SEQ ID NO:42 could be replaced with either of the primers shown in SEQ ID NO:44 or SEQ ID NO:45.

Class II R-genes encode proteins with a conserved putative membrane anchor. The primers shown in SEQ ID NOS:46–47 were successfully used to isolate R-gene homologs of this class. The primer in SEQ ID NO:47 could be replaced with the primer shown in SEQ ID NO:48.

The R-gene homologous fragments were obtained by performing PCR reactions (denaturing at 94° C. for 1 min, annealing at 48–52° C. for 1 min, extending at 72° C. for 2 min, for a total of 35 cycles) using primers similar or identical to the ones described above and the Gibco BRL reagent system (catalog no. 10198-018; Life Technologies, Gaithersburg, Md.) under standard conditions as recommended by the manufacturer. The PCR products were electrophoresed on agarose gels and often appeared as one dominant 0.5 kb band. However, subcloning of the gel-purified band in the vector PCRscript (Stratagene, La Jolla, Calif.) and sequence analysis of the individual amplified products as performed according to the manufacturer's procedures (ABI PRISM™ Dye Terminator Cycle Sequencing, Perkin Elmer. Foster City, Calif.) demonstrated that each band appeared to contain dozens of different fragments of R-gene homologs. To guarantee the identification of as many subclasses as possible, the primers mentioned above were used under the same conditions to isolate R-gene homologs not only from tobacco but also from the related plant species *Solanum microdontum*. Over 200 R-gene homologous fragments isolated from these plant species were aligned and grouped into different subclasses based on the level of homology at the amino acid level. Each subclass was defined by at least about 70% identity among members or the ability of members to cross-hybridize on Southern blots.

Having identified many different subclasses, the next step was to use representative members of these subclasses as probes on Southern blots to determine the total number of R-gene homologs. Ten different subclass-representatives of class I (SEQ ID NOS:21–30) and six different subclass-representatives of class II (SEQ ID NOS:31–36) were amplified from corresponding plasmids using the standard primers T3 and T7 (Life Technologies, Gaithersburg, Md.). The amplified fragments were subsequently labeled using Prime-It II (Stratagene, La Jolla, Calif.), and an equivalent of $5\times10^7$ cpm was added to 15 mL Rapid-hyb buffer (Amersham, Arlington Heights, Ill.) to perform Southern blot experiments with Hybond-N+ filters (Amersham, Arlington Heights, Ill.) containing plant DNA digests. The 16 different hybridization experiments visualized a total of about 350 R-gene homologs in tobacco, 200 of class I and 150 of class II. Probes isolated from *S. microdontum* appeared as useful as tobacco probes in visualizing R-gene homologs on filters containing tobacco DNA, demonstrating that R-gene homologs are conserved among related plant species and indicating the applicability of using both endogenous and heterologous probes. The ability to visualize this large amount of R-gene homologs using a selection of 16 probes implies the significance of these probes, and thus the corresponding DNA sequences, for the isolation of functional tobacco R-genes, many of which are expected to display a high degree of homology with any of these DNA fragments. Biologically functional R-genes should contain a region of approximately 180 amino acids with about 70% or greater sequence similarity, preferably about 80% or greater similarity and most preferably about 90% or greater sequence similarity, to the sequence of any of the selected 16 DNA fragments (SEQ ID NOS:21–36). Filters were also hybridized with the tomato Pto gene and with two tomato Xa21 homologs provided by Pam Ronald (University of California, Davis), revealing approximately 40 more bands.

Construction of Full-length Libraries:

A modified binary cosmid vector 04541 derived from SLJ44024 (Jones et al., 1992), designated 04541M, was generated that contained, apart from the neomycin phosphotransferase (ntptII) gene, the INF1 gene driven by the 35S promoter of figwort mosaic virus between the borders of the T-DNA (FIG. 1). The 04541M vector was constructed by first amplifying both the DNA sequence encoding the signal peptide of the PR1a gene (Hammond-Kosack et al., 1994), using the primers shown in SEQ ID NOS:49–50, and the INF1 gene (294 bp; isolated from genomic DNA of the US-8 genotype of *P. infestans*), using the primers shown in SEQ ID NOS:51–52. The amplified signal peptide sequences were digested with XbaI-KpnI and KpnI-BglII, respectively, and subcloned into the plasmid vector pMON11770 (FIG. 2), digested with XbaI and BamHI. The resulting plasmid contained a cassette comprising, in order, the 35S promoter of figwort mosaic virus, the PR1a signal peptide sequence, the INF1 gene, and the transcription terminator sequence of the nopaline synthase (nos) gene. A HindIII-SmaI DNA fragment containing this cassette was subcloned into pBluescript (Strategene, La Jolla, Calif.), and linearized with HindIII and HincII. Finally, the cassette was liberated from this vector with HindIII and XhoI and cloned into the binary cosmid vector 04541, digested with the same enzymes.

Both the original 04541 vector and the new 04541M vector were transduced to *E. coli* MR cells using the Gigapack III Gold system (Stratagene, La Jolla, Calif.) and conjugated to *Agrobacterium* ABI by triparental mating (Ditta et al., 1980). ABI is the A208 *Agrobacterium tumefaciens* strain carrying the disarmed pTiC58 plasmid pMP90RK (Koncz et al., 1986). Agrobacteria were grown for 30 hours at 30° C. in LB medium (10 g tryptone, 5 g yeast and 5 g NaCl per liter) containing 25 μg/mL chloramphenicol and 50 μg/mL kanamycin. *E. coli* containing the helper plasmid pRK2013 were grown overnight in LB medium containing 50 μg/mL kanamycin. *E. coli* harboring the binary cosmid vectors were grown in LB medium containing 10 μg/mL tetracycline. After all the cultures were grown, 4 mL of LB was added to a tube containing 100 mL each of ABI, *E. coli* (pRK2013), and *E. coli*(binary cosmid vector). This mixture was centrifuged in a microfuge for 1 minute, and the supernatant fraction was decanted. The pellet fraction was resuspended in the remaining liquid, and an aliquot was pipetted onto the center of an LB-agar plate. After growth overnight at 30° C., an aliquot of cells from this plate was streaked onto an LB plate supplemented with 2 μg/mL tetracycline, 50 μg/mL kanamycin, and 25 μg/mL chloramphenicol. After 24–48 hours at 30° C., colonies were present on the selection plates resulting from "triparental" mating. Four individual colonies were selected from this plate, and each was separately inoculated into a liquid culture of LB supplemented with 2 μg/mL tetracycline, 50 μg/mL kanamycin, and 25 μg/mL chloramphenicol, and grown at 30° C. The presence of the intact T-DNAs was confirmed by restriction analysis of plasmid DNA isolated from the *Agrobacterium* strains.

Injection of the *Agrobacterium* strain carrying 04541 into the intercellular spaces of tobacco and *N. benthamiana* did, as expected, not result in any phenotype, and injected tissues appeared identical to tissues injected with the *Agrobacterium* strain lacking a cosmid vector. A severe necrotic response, however, resulted from injection of 04541M into tobacco leaves, indicating that transient expression of INF1 does trigger an HR in tobacco. In *N. benthamiana*, a limited amount of necrosis could only be observed after trypan blue staining of injected tissues for dead cells. The amount of INF1-induced necrosis in *N. benthamiana* is less than 5% of the amount of induced necrosis in tobacco. These results indicate that (1) tobacco contains the appropriate genes to recognize the Phytophthora elicitor INF1 and that this recognition triggers a rapid and strong HR, and (2) *N. benthamiana* does not contain the appropriate genes to recognize INF1 as strongly as tobacco or is not able to trigger a rapid and strong HR upon recognition of INF1. Thus, there seems to be a clear correlation between ability to recognize INF1 and disease resistance against *P. infestans*.

Assuming a role for R-genes in recognition of INF1, it was our intention to screen tobacco R-gene homologs for their ability to trigger an INF1-dependent HR in *N. benthamiana*. For this purpose, genomic DNA was isolated from young tobacco leaves, partially digested with SauIIIA, treated with calf alkaline phosphatase (Boehringer Mannheim, Indianapolis, Ind.) to remove 3'-OH groups, ligated to 04541 M digested with BamHI, and transduced to *E. coli* MR cells using the Gigapack III Gold system (Stratagene, La Jolla, Calif.), to create a binary cosmid library of $2\times10^6$ clones with an average insert size of 20 kilobase pairs.

The tobacco binary cosmid library was screened with all subclass-specific probes that were previously used for the initial Southern blot analyses. Routinely, we use five different probes simultaneously to screen the library. All binary cosmid vectors that hybridize to the subclass-specific probes (SEQ ID NOS:21–36) were subjected to PCR analysis with R-gene primers (SEQ ID NOS:40–41) to confirm the presence of at least part of an R-gene homolog. These "positive" cosmids were subsequently conjugated into *Agrobacterium tumefaciens* to generate strains for transient or stable transformation of plants.

Example 2

Isolation of Non-host Inducible Genes

Overexpression of genes that function in non-host defense signaling may enhance disease resistance in susceptible plants. To identify such non-host inducible genes (NHIs), the following experiments were carried out.

RNA Extraction

RNA was extracted using TRIzOl™ Reagent according to the manufacturer's protocol (Life Technologies, Gaithersburg, Md.) from leaves of the following plants 1. Tobacco leaves, 4 hours after a challenge infection with *P. infestans*
2. Tobacco leaves, 4 hours after a mock treatment by spraying with water
3. Tobacco leaves, 18 hours after a challenge infection with *P. infestans*
4. Tobacco leaves, 18 hours after a mock treatment by spraying with water Subtractions The following PCR-select cDNA subtractions were performed according to manufacturer's protocol (Clonetech, Palo Alto, Calif.) to select for genes predominantly induced by *P. infestans* in resistant plants:

All cDNAs in "2" subtracted from the cDNAs in "1", to generate pool I

All cDNAs in "4" subtracted from the cDNAs in "3" to generate pool II

Candidate Gene Selection

Subtracted cDNA pools were cloned into the pGEMT vector (Promega, Madison, Wis.). One thousand clones from tobacco subtractions were randomly picked up for further expression analysis. Subtracted clones were amplified by PCR using standard T7 and M13 reverse primers (Life Technologies, Gaithersburg, Md.) from the vector, and dotted on nylon membranes (Amersham, Arlington Heights, Ill.) in duplicates. The duplicate membranes were hybridized with cDNA probes derived from messenger RNA isolated using TRIzol™ Reagent (Life Technologies, Gaithersburg, Md.) from either resistant or susceptible plants. The dots that displayed stronger hybridization with resistant than with susceptible probe were selected for further Northern blot analysis to confirm their expression.

Filters used for Northern blot analysis contained 10 micrograms of RNA isolated from:
1. Tobacco leaves, 0, 4, 8 and 18 hours after a challenge infection with *P. infestans*
2. Tobacco leaves, 0, 4, 8 and 18 hours after a mock treatment by spraying with water Prioritization of Leads Based on the Northern blot data, candidates were prioritized by using the following criteria:
1. stronger induction in infected than mock-treated tobacco plants
2. stronger induction at 4 hours after infection than 18 hours after infection
3. stronger induction in infected tobacco than in infected susceptible potato and/or benthamiana
4. encoding proteins that are either clearly involved in upstream signaling, such as receptors, kinases, and transcription factors, or have an enzymatic function Isolation of Full Length cDNAs To isolate full-length cDNAs, a tobacco cDNA library was generated using the SMART™ cDNA Library Construction Kit (Clonetech, Palo Alto, Calif.) according to the manufacturer's recommendations. A total of $2 \times 10^6$ independent clones for the library were generated and amplified in 40–50 plates (150×15 mm). Lysate from every plate was collected and stored individually as a subpool for each whole library.

For each candidate gene, specific primers were designed based on the sequence obtained from the subtracted clones. Gene specific primers were used to screen all subpools for those that contained at least one positive cDNA.

Subcloning of Full-length Sequences in a Binary Plasmid Vector

The binary vector pMON30656 (FIG. 5) was constructed to facilitate cloning and subsequent analysis of resistance-associated genes. This vector allows subcloning of full-length genes isolated from SMART libraries in a single step because it contains a unique SfiI site between the 35S promoter of Figwort Mosaic Virus and the untranslated trailer sequence with termination signals of the nopaline synthase gene of *A. tumefaciens* pTiT37. The vector also contains Lox-P sites that allow the gene of interest to be rescued from plant genomes. Alternatively, genes of interest can be rescued by fragmenting DNA with PacI. The fragmented DNA needs to subsequently be self-ligated to generate a plasmid structure that contains, apart from the gene of interest, the kan gene, which confers resistance to kanamycin and neomycin to bacteria, and the origin of replication of the bacterial plasmid pACYC184.

Example 3

Isolation of an Elicitor-binding Protein from Tobacco

To isolate plant factors or receptors other than R-genes that can activate a signal transduction pathway leading to induction of HR based on recognition of *Phytophthora infestans* elicitors, the yeast MATCHMAKER two-hybrid was used (Clonetech, Palo Alto, Calif.). A tobacco MATCH-MAKER cDNA library was constructed according to the manufacturer's protocol and used to screen for the ability to interact with the *Phytophthora infestans* elicitor INF1. A total of $3 \times 10^6$ clones were screened, and six positive clones have been identified. One of the positive clones, designated Nhr1 (SEQ ID NO:60), contains two zinc finger-like domains and a bromo domain, which suggests that Nhr1 might be a transcription regulator or a signalling protein.

To isolate the full length gene for Nhr1, a binary cosmid library containing both the INF1 gene under the control of the FMV promoter and tobacco DNA fragments with an average size of 20 kilobasepairs was constructed and screened with Nhr1. Positive clones were conjugated into *Agrobacterium*, and overnight cultures of the resulting strains, resuspended in 0.1×MS medium (Sigma Chemical Co., St. Louis, Mo.) and diluted to an $OD_{600}=1.0$, were injected into the intercellular spaces of *Nicotiana benthamiana*, as described below.

Example 4

Identification of a Plant System to Screen for Functional Genes

To obtain preliminary evidence for gene activity, a model plant system was needed that would allow the screening of tobacco R-genes, NHIs and putative elicitor-receptors for functional activity. This plant system should be (1) highly accessible to transient transformation, (2) susceptible to the target pathogen *P. infestans* and a model pathogen such as *Pseudomonas syringae*, and (3) insensitive to the INF1 peptide. *Nicotiana benthamiana* meets all of these criteria. To determine the efficiency of transient transformation, *Agrobacterium* strains carrying a gene encoding green fluorescent protein (GFP) between the borders of the T-DNA at an $OD_{600}=0.1$ were injected into the intercellular spaces of leaves of *N. benthamiana*. Three days after injection, protoplasts were isolated using the following protocol: leaves were cut into small pieces and digested in a solution containing 2% cellulase, 0.5% macerozyme R-10, 0.5 M sucrose and 5 mM $CaCl_2$ for two and a half hours. Digested product was flown through a 40 micometer sieve and centrifuged at 80–100×g for 4 min. Floating protoplasts were then transferred to a new tube and counted by light microscopy. Subsequently, the number of fluorescing protoplasts was determined by UV radiation. The percentage of transformed cells was determined by multiplying the ratio of total protoplasts to fluorescing protoplasts with 100. As shown in Table 1, this experiment and a similar experiment using the GUS gene instead of the GFP gene as a reporter demonstrate a transformation frequency of about 90%.

TABLE 1

| Gene expression in protoplasts isolated from Agrobacterium-infected leaves. | |
| --- | --- |
| Reporter gene | Percentage of protoplasts expressing reporter gene |
| FMV:GFP | 87.9 + 1.9 |
| CaMV:GUS | 91.1 + 0.4 |

Leaves were injected with *Agrobacterium* strains carrying reporter genes encoding green fluorescent protein (GFP) and β-glucuronidase (GUS), respectively, between the borders of the T-DNA. The GUS gene was interrupted by an intron to prevent bacterial gene expression. The GFP gene was driven by the 35S promoter of figwort mosaic virus; the GUS gene was driven by the 35S promoter of cauliflower mosaic virus. *Agrobacterium* strains used were AB1 and GV2260, respectively. Two days after infiltration, protoplasts were monitored for autofluorescence to determine the frequency of GFP expressing cells. The frequency of GUS expressing cells was determined by staining protoplasts with X-glucuronide. Data are averages of seven independent experiments for GFP, and three independent experiments for GUS.

Little is known about the response of *N. benthamiana* against fungal pathogens that are avirulent on other related plants such as tobacco. To determine *N. benthamiana* susceptibility to *P. infestans*, 6-week-old plants were infected with 8000 spores/mL of the genotypes US-1 and US-8. Tobacco and potato plants were infected simultaneously as controls for resistance and susceptibility, respectively. Infected plants were placed in a humid growth chamber at 17° C. in the dark for approximately 40 h to ensure infection and then transferred to a growth chamber at 18° C. with 16 h light/8 h dark for development of late blight symptoms. Five days after infection, large regions of *N. benthamiana* plants had collapsed. Microscopic analysis of infected leaves stained with trypan blue and destained with chloral hydrate (Keogh et al., 1980) demonstrated extensive fungal growth in lesions. As expected, no disease symptoms were observed on tobacco, whereas potato plants displayed severe disease symptoms in all above-ground tissues.

The low sensitivity of *N. benthamiana* to the INF1 peptide was demonstrated with a purified fusion protein comprising glutathione-S-transferase and INF1. This fusion protein was generated by (1) amplifying the INF1 gene using primers shown in SEQ ID NO:53–54, (2) subcloning the amplified DNA fragment into pCRscript (Stratagene, La Jolla, Calif.), (3) releasing the INF1 gene from this vector using BamHI and NotI. (4) subcloning the BamHI-NotI DNA fragment containing INF1 into pGEX-5x-3 (Pharmacia, Piscataway, N.Y.), (5) expressing the GST-INF1 fusion in *E. coli*, and (6) purifying the fusion protein as described previously (Zhang et al., 1995). Plants at the 8-leaf stage were used to inject the third leaf with the purified protein. Two days after injection, less than 10% of the inoculated region developed a hypersensitive necrotic response. Because a similar experiment in tobacco resulted in necrosis of the entire inoculated region, it can be concluded that *N. benthamiana* is at least 10-fold less susceptible to INF1 than tobacco.

The concept of using *N. benthamiana* to screen for functional disease R-genes was demonstrated in two sets of experiments. First, it was shown that stable transformation of *N. benthamiana* with the tomato R-gene Pto resulted in functional disease resistance (Rommens et al., 1995). Second, the leaves of *N. benthamiana* were transiently transformed with the tobacco disease R-gene N (plasmid SPDK167 with the neomycin phosphotransferase as plant selectable marker and spectinomycin resistance as bacterial marker, provided by Dr. Barbara Baker, USDA, Albany) and challenged after three days with the viral pathogen tobacco mosaic virus (TMV). Five days after the challenge infection, transformed tissues developed a hypersensitive response (HR), indicative of functional activity of the N gene in *N. benthamiana*. No HR response was observed in control plants transiently transformed with the GFP gene and infected with TMV.

Example 5

Identification of Functional Genes by Screening R-gene Homologs and NHIs

Screening R-gene Homologs:

*Agrobacterium* strains were grown for about 2 days in liquid broth containing the appropriate antibiotics to select for the presence of both *Agrobacterium* and the cosmid vector. *Agrobacterium* cells were precipitated and resuspended to an $OD_{600}$=0.05 in TT medium (0.1×Murashige and Skoog basal medium with Gamborg's vitamins [Sigma MS B5 salts], 3.9 g/L MES pH 5.4, 20 g/L sucrose, and 10 g/L glucose). The cell suspensions were injected with a 1 mL syringe into the intercellular spaces of leaves of *N. benthamiana*. It was expected that R-genes that recognize the *Phytophthora* elicitor INF1 would induce an HR in the presence of the INF1 protein in the *N. benthamiana* transient expression system. A total of 181 strains carrying class I R-genes were injected. In 7 cases, injections resulted in the development of a rapid HR within 3 days after injection. The corresponding R-genes were designated R1–R7. Sequence analysis of the 0.5 kb fragments between P-loop and GLPLAL region of the first six R-genes showed that these genes were most similar to the tobacco R-gene N. The seventh R-gene homolog induced a weak HR only. This homolog appeared most homologous to the tomato R-gene Prf. To confirm that the HR induced by R1–R7 was INF1 dependent, a second library was constructed with tobacco genomic DNA fragments inserted into the binary cosmid vector 04541 without the INF1 gene. The probe used to hybridize this second library was generated by (1) amplifying the P-loop-GLPLAL region of R1–R7 using primers SEQ ID NOS:40–41 and (2) pooling and radioactively labeling these amplified products. Hybridization positive clones were conjugated into *Agrobacterium*, and cell suspensions of the resulting strains ($OD_{600}$=0.05) were mixed with an equal amount of cells of *Agrobacterium* strains containing either a binary cosmid carrying the GFP gene or a binary cosmid carrying the INF1 gene. The mixed strains were then injected into the intercellular spaces of *N. benthamiana*. As shown in Table 2, 10 homologs of the R1-R7 genes were able to strongly enhance the HR response induced by INF1. The 10 tobacco homologs of the R1-R7 genes that trigger an INF1-dependent HR were designated Enh1-Enh10 (enhancer of INF1-induced HR). Partial sequences of Enh1-Enh10 are presented in SEQ ID NOS: 1–10, respectively. FIG. 3 shows the alignment of the amino acid sequences SEQ ID NOS:11–20 and demonstrates that these R-genes share a high level of homology.

Table 2. Response of *N. benthamiana* to transient co-expression of a subset of R-genes with either INF1 or GFP.

To screen homologs of R-genes for their ability to trigger an HR in the presence of INF1, plants were co-injected with *Agrobacterium* strains: one containing an R-gene homolog and another one containing the INF1 gene. As a control, *Agrobacterium* strains carrying an R-gene homolog were co-injected with *Agrobacterium* strains carrying the GFP gene. Four and seven days after injection (DAI), the extent of HR was measured. "–": <10% of injected tissue responds with HR; "+": 10–20% HR; "++": 20–50% HR; "+++": 50–100% HR.

|  |  | 4 DAI | | 7 DAI | | |
|---|---|---|---|---|---|---|
| R-gene # | | +GFP | +INF1 | +GFP | +INF1 | homolog |
| Enh1 | SEQ ID NO: 18 | − | + | − | +++ | N gene |
| Enh2 | SEQ ID NO: 13 | − | − | − | + | Prf gene |
| Enh3 | SEQ ID NO: 17 | − | ++ | − | +++ | N gene |
| Enh4 | SEQ ID NO: 11 | − | − | − | ++ | Prf gene |
| Enh5 | SEQ ID NO: 16 | − | − | − | ++ | N gene |
| Enh6 | SEQ ID NO: 15 | − | + | − | ++ | N gene |
| Enh7 | SEQ ID NO: 20 | − | ++ | − | +++ | N gene |
| Enh8 | SEQ ID NO: 12 | − | − | − | + | Prf gene |
| Enh9 | SEQ ID NO: 14 | − | ++ | − | +++ | N gene |
| Enh10 | SEQ ID NO: 19 | − | + | − | ++ | N gene |

Binary cosmid vectors carrying tobacco R-gene homologs with unknown function can be stably introduced into *N. benthamiana* via *Agrobacterium*-mediated transformation. In this way, a library of transgenic *N. benthamiana* plants can be created, with each different plant expressing at least one tobacco R-gene. To limit the number of independent transformations that need to be performed, we grouped about 180 *Agrobacterium* strains containing binary vectors with class I R-gene homologs in 18 pools of 10 strains each. Twenty-five transgenic *N. benthamiana* lines were generated for each pool. Seed isolated from the different pools can be used to screen for disease resistance against any pathogen that is avirulent in tobacco and virulent in *N. benthamiana*. Transgenic *N. benthamiana* plants expressing resistance against such a pathogen are likely to contain a functional tobacco R-gene. The sequence of this R-gene can be determined by performing PCR reactions (e.g., long range PCR or inverse PCR) using primers specific for T-DNA sequences flanking the tobacco DNA insert. This R-gene can then be introduced into any crop of interest via cloning in the appropriate vectors and transformation to develop disease resistance in that crop against the target pathogen.

Many sequences with homology to R-genes have been described in this application. Any of these genes can be used as probes to study segregation of resistance in a segregating population of plants. In this way, it may be possible to identify bands on Southern blots that cosegregate with resistance. These bands are good markers for resistance and may be used as such in breeding programs. Additionally, these bands may visualize the segregating R-genes themselves. Thus, the R-gene homologous sequences presented here may be useful for both the mapping and isolation of R-genes. For example, we have tested all subclass-representative DNA fragments mentioned previously as probes on Southern blots containing DNA of potato plants that segregate for resistance against the US-8 genotype of *P. infestans*. By using a DNA fragment (SEQ ID NO:29) amplified from tobacco DNA using primers SEQ ID NO:40–41 under standard conditions, we identified one band in many resistant plants that is always absent in susceptible plants.

Stable Transformation of Active R-gene Homologs into *N. benthamiana*:

To examine whether the ability of Enh genes to enhance the INF1-induced HR would lead to increased disease resistance against *P. infestans* in transgenic *N. benthamiana* plants, the 10 different Enh genes (SEQ ID NO:

genes, will be involved in resistance against other species of *Phytophthora*, including *P. megasperma*, *P. drechsleri*, *P. capsici*, *P. cactorum*, *P. cryptogea*, and *P. cinnamomi*, because they all encode elicitors that are very similar in structure to INF1 and that induce an HR in tobacco (Yu, 1995). It is even possible that these genes will provide resistance against other pathogens that produce INF1-like elicitors, such as *Pythium vexans*. The durable character of tobacco's non-host resistance against *P. infestans* may, in part, be due to the fact that tobacco contains at least four functional R-genes involved in recognition of the elicitor INF1.

To demonstrate the applicability of R-genes recognizing INF1 for control of *Phytophthora* species other than *P. infestans*, we isolated the elicitor encoding gene of *P. sojae*, causal agent of Phytophthora rot in soybean. This gene can be isolated by performing a PCR reaction on total *P. sojae* DNA with the two primers shown in SEQ ID NOS:55–56. The PCR product can be subcloned into the PCRscript vector (Stratagene, La Jolla, Calif.) and sequenced to confirm integrity of the amplified DNA. A 300 bp fragment digested with KpnI and BglII that contains the INF1 homologous gene can be ligated with a 100 bp signal peptide sequence of the PR1 gene digested with XbaI and KpnI (Hammond-Kosack et al., 1994) and subcloned into the pMONI 1770 vector (FIG. 2). A NotI digested fragment that contains FMV promoter, signal peptide, *P. sojae* elicitin, and nos terminator can then be purified and subcloned into the pMON 17227 (FIG. 4) T-DNA binary vector. The successful clone can be selected and conjugated into *Agrobacterium* for further testing.

The HR-enhancing activity of Enh genes may not be limited to elicitors of *Phytophthora* species. It is possible that expression or overexpression of Enh genes results in a broad-spectrum control of viral, bacterial, or fungal pathogens. This may be due to a spontaneous induction of signaling pathways involved in disease resistance.

Screening NHIs:

An indication for the activity of resistance-associated genes can be obtained by subjection of *N. benthamiana* leaves that transiently express these genes with the virulent bacterial pathogen *Pseudomonas tabaci*, causal agent of the "wild fire" disease. For this purpose, right halves of leaves were injected with *Agrobacterium* strains carrying pMON30656 (FIG. 5) derivatives that contain genes of interest. As a control, left halves of leaves were injected with an *Agrobacterium* strain containing the binary vector pMON30656. Two days after injection, left and right halves of leaves were injected with a bacterial suspension. This suspension was obtained by washing an overnight culture of *P. tabaci* with 10 mM $MgCl_2$, and diluting this suspension to an $OD_{600}$ of 0.001 (the equivalent of $10^6$ colony forming units) (Rommens et al., 1995). Four days after pathogen challenge, disease progression in the right halves of leaves was compared with that in the control left halves.

Of the two genes analyzed in this way until now, expression of one gene was shown to partially control the wild fire disease. TOB-F12 (SEQ ID NO:58) encodes a homolog of the 21 kDa protein of *Daucus carota* and shares some conserved amino acids in the N-terminal region with Xa21, a receptor kinase involved in resistance to the rice bacterial pathogen *Xanthomonas* (Song et al., 1995).

Testing NhrI:

To demonstrate that the induction of HR was INF1-dependent, a second cosmid library was generated that did not contain INF1. Clones hybridizing to Nhr1 were conjugated into *Agrobacterium* and mixed with *Agrobacterium* strains carrying either the INF1 gene or the gene encoding green fluorescent protein (GFP) between the borders of the T-DNA. The mixed strains were injected into leaves of *N. benthamiana* at an $OD_{600}$=0.3. Three out of five strains tested induced an HR in the presence of INF1 within three days of injection. All five strains induced an HR after five days, and one of the five strains could induce an HR even at $OD_{600}$=0.1. This cosmid NhrI clone was used to further analyze its inducibility of HR in the presence of INF1 (Table 3). No HR was induced in the presence of GFP, demonstrating that the ability to induce an HR was INF1-dependent.

TABLE 3

Cosmid Nhr1 enhanced HR significantly in the presence of INF1

| | necrosis percentage (average of 31 leaves) | | | | |
|---|---|---|---|---|---|
| | 78 hai | 94 hai | 102 hai | 120 hai | 140 hai |
| Nhr1 + INF1 | 10.97% | 19.84% | 25.97% | 28.87% | 30.97% |
| INF1 + GFP | 0.32% | 0.55% | 3.23% | 3.87% | 4.19% |
| Nhr1 + GFP | 0 | 0 | 0 | 0 | 0 |

(hai: hours after inoculation)

The full length cDNA version of NhrI was isolated using a 5'/3' RACE kit from Boehringer Mannheim (Indianapolis, Ind.) according to the manufacturer's protocol. The primers used for 5' RACE are

```
TAA GCC TCT CGA CAC ATG GC:      SEQ ID NO:61

TCG GTT GCA CAA TTA GTG GC:      SEQ ID NO:62

CGA TTC GTG GCA CAA CAT TC:      SEQ ID NO:63
```

The primers used for 3' RACE are

```
TGG TCA AAG TAT TGC CAC C:       SEQ ID NO:64

GGG GGA GAA CTG ATT TGC TG:      SEQ ID NO:65

TTA GGT GTA CAG TGT ACC CC:      SEQ ID NO:66
```

The full length sequence is given in SEQ ID NO:60.

Example 6

Cloning of Active Genes into Potato to Confer Late Blight Disease Resistance

All non-host genes identified that enhance HR and/or defense responses in model systems are good candidates to enhance disease control in crops. The research described in the previous section identified binary cosmid vectors that contain Enh and Nhr1 genes able to enhance the INF1-inducible HR upon transient and stable expression in *N. benthamiana*. The same binary vectors were used to stably transform potato.

*Agrobacterium* strains carrying the binary cosmid vector with the Enh3 gene (pMON30621; FIG. 7) (SEQ ID NO:3) were grown overnight in 2 mL of LB medium containing 2 μg/mL tetracycline, 50 μg/mL kanamycin, and 25 μg/mL chloramphenicol. The following day, the bacteria were diluted 1:10 with MSO medium containing 4.4 g MS salts (Sigma Chemical Co., St. Louis, Mo.), 30 g sucrose, and 2 mL vitamin B5 in a 1 liter volume, pH 5.7, or until an optical density reading of 0.1 at 600 nm was obtained.

Leaves were removed from the stems of potato plants (*Solcanum tuberosum*) that had been grown from stem cuttings containing nodes under sterile conditions, at a temperature of 19° C., a 16-hr light/8-hr dark cycle, and a light intensity of 100 µE/sec/m$^2$, for three weeks on PM medium containing 4.4 g MS salts, 30 g sucrose, 0.17 g NaH$_2$PO$_4$.H$_2$O, 0.4 mg thiamine-HCl, 25 g ascorbic acid, and 0.1 g inositol per liter, pH 6.0, and 0.2% Gelrite agar. The stems were cut into 3–5 mm segments.

Before inoculation, 30 stem segments were placed onto a co-culture plate to serve as noninoculated controls. Co-culture plates contained 0.9% agar-solidified callus induction medium containing 1×MS salts, 5.0 mg/L zeatin riboside, 10 mg/L AgNO$_3$, 3% sucrose, 500 mg/L carbenicillin, 0.3 mg/L GA$_3$, and 0.025 mM glyphosate. Shoots began to appear after 8 weeks. Explants were transferred to fresh shoot induction medium every 4 weeks over a 12-week period. Shoots were excised from the callus and placed on PM medium solidified with 0.2% Gelrite agar for about 2 weeks. The resulting plants were used to generate transgenic lines comprising at least four cuttings per transformation event. As soon as cuttings were large enough and had developed roots, three cuttings per line were placed into soil.

Transgenic plantlets and plantlets derived from untransformed controls were grown in 4" pots in growth chambers at 18° C. After approximately 3 weeks, plants were inoculated with approximately 10$^4$ sporangia/mL of the US-8 genotype of *P. infestans*. Inoculated plants were placed in a humid growth chamber at 17° C. in the dark for about 40 h to insure infection and subsequently transferred to a growth chamber at 18° C. for development of late blight symptoms. Disease severity was assessed at 3, 4, and 5 days postinoculation by estimating the percentage of leaf tissue covered by disease symptoms. Control plants were heavily infected by *P. infestans* with 25% of tissues damaged by the pathogen at the third day. Five days after infection, rapid disease progress had resulted in a collapse of 83% of leaf tissues. The average "area under the disease progress curve" (AUDPC), a reliable indicator of the level of susceptibility, of all control plants was 107. Some transgenic lines appeared equally susceptible to *P. infestans* as control plants, indicating either absence or inadequate expression of the transgene in these lines. Interestingly, four transgenic lines consistently displayed significantly enhanced resistance, with only 50% to 60% disease symptoms at the fifth day. The AUDPC value of these lines was between 60 and 70. This result indicates that expression of Enh3 in potato can result in enhanced disease resistance against *P. infestans*.

The cosmid clone Nhr1 (pMON30620; FIG. 6) was stably transformed into potato cultivar Russet Burbank as described above. A total of 50 putative transgenic lines have been generated. Disease tests revealed that six transgenic lines displayed enhanced resistance against *Phytophthora infestans* race US8. One of the six lines, 56433, which contains the full length Nhr1 gene, was chosen to confirm its enhanced resistance. Six cuttings of each of 56433 and three vector control lines were challenged with *Phytophthora infestans* and disease progress data was summarized in Table 4. Line 56433 significantly enhanced resistance with disease control rate about 37% five days after *Phytophthora infestans* inoculation (dai). Northern blot analysis of line 56433 revealed that expression of the Nhr1 gene was very low in this plant, less than one tenth of the level expressed in tobacco. We propose that enhanced expression of the Nhr1 gene in potato may increase resistance significantly.

TABLE 4

Disease test on line 56433 and vector control lines

| Lines | Disease 5 dai (%) |
|---|---|
| 56433 (C45-2) | 17.5% |
| 38585 (VC) | 30.3% |
| 38588 (VC) | 24.4% |
| 38599 (VC) | 28.8% |

Example 7

Full-length Sequence of Enh3

Preliminary data suggest that Enh3 gene expression levels in transgenic potato plants are very low. It is possible that higher levels of Enh3 gene expression in transgenic potato plants would lead to a further increase of Enh3-mediated disease resistance against *P. infestans*. It may be possible to further increase disease resistance in transgenic potato plants by overexpressing the Enh3 gene. In order to fuse the Enh3 gene with promoters such as the promoter of the nopaline synthase gene, the full length genomic sequence of Enh3 (SEQ ID NO:57) was determined by ABI PRISM Dye Terminator Cycle Sequencing (Perkin Elmer, Foster City, Calif.). Because no cDNA clone is yet available, it is not yet possible to predict the level of homology of Enh3 with its closest homolog, the tobacco disease resistance gene N, which has functional activity against tobacco mosaic virus. However, current estimates indicate an overall homology of about 65% at the DNA level.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the invention has been described in detail for the purpose of illustration, it is understood that such detail is solely for that purpose, and variations can be made therein by those skilled in the art without departing form the spirit and scope of the invention which is defined by the following claims.

REFERENCES

Anderson et al., Plant Cell 9: 641–51, 1997.
Armstrong et al., Crop Science, 35:550–557, 1995.
Ausubel et al., *Current Protocols in Molecular Biology*, John Wiley and Sons, Inc., 1995.
Battraw and Hall, Plant Mol. Biol., 15(4):527–538, 1990.
Bauer et al., Gene, 37: 73, 1985.
Bent et al., Science 265: 1856–60, 1994.
Bol et al., Ann. Rev. Phytopathol, 28:13–138, 1990
Bostock et al., Science 212:67–69, 1981.
Bower and Birch, Plant J., 2:409, 1992.
Bowles, Ann. Rev. Biochem, 59: 873–907, 1990.
Broekaert et al., Critical Rev Plant Sci 16: 297–323, 1997.
Bytebier et al., Proc. Natl. Acad. Sci. USA, 84:5345, 1987.
Campbell et al., Plant Physiol., 92: 1–11, 1990.
Cao et al., Proc. Natl. Acad. Sci. USA, 95:6531–6, 1998.
Chau et al., Science, 244:174–181. 1989.
Cheng et al., Plant Cell Rep. 15(9): 653–7, 1996.
Christensen et al., Plant Mol. Biol., 18: 675,689, 1992.

Christou et al., Plant Physiol., 87: 671–674, 1988.
Christou et al., Bio/Technology, 9:957, 1991.
Craik, BioTechniques, 3: 12–19, 1985.
Cuypers et al., Mol. Plant-Microbe Interact, 1: 157–160, 1988.
Davey et al., Symp. Soc. Exp. Biol., 40: 85–120, 1986.
Davey et al., Plant Mol. Biol., 13(3): 273–285, 1989.
De Kathen and Jacobsen, Plant Cell Rep., 9(5): 276–9, 1990.
De la Pena et al., Nature, 325:274, 1987.
Ditta et al., Proc Natl Acad Sci USA 77: 7347, 1980.
Fields and Sternglanz, Trends Genet., 10:286–292, 1994.
Frits Eckstein et al., Nucleic Acids Research, 10: 6487–6497, 1982.
Fritzemeier et al., Plant Physiol., 85: 3441, 1987.
Fromm et al., Proc. Natl. Acad. Sci. USA, 82(17): 5824–5828. 1985.
Fromm et al., Bio/Technology 8: 833, 1990.
Gasser and Fraley, Science, 244: 1293, 1989.
Gordon-Kamm et al., Plant Cell, 2:603, 1990.
Grant et al., Science 269: 843–46, 1995.
Hammond-Kosack et al., Proc Natl Acad Sci USA, 91:10445. 1994.
Horn et al., Plant Cell Rep., 7:469, 1988.
Innes, Curr. Opin. Plant Biol. 1:299–304, 1998.
Jones et al., Transgen. Res., 1: 285–297, 1992.
Kamoun et al., Mol Plant Microbe Interact, 10: 13–20, 1997.
Kapila et al., Plant Science, 122:101–108, 1997.
Kay et al., Science, 236:1299, 1987.
Keogh et al., Trans Br Mycol Soc, 74:329–333, 1980.
Koncz et al., Mol Gen Genet, 204:383–396, 1986.
Koziel et al., Bio/Technology, 11: 194, 1993.
Lawrence et al., Plant Cell, 7:1195–206, 1995.
Lindstrom et al., Developmental Genetics, 11: 160, 1990.
Linthorst, Crit. Rev. Plant Sci., 10: 123–150, 1991.
Logemann et al., Plant Cell, 1: 151–158, 1989.
Mandel et al., Plant Mol. Biol. 29: 995–1004, 1995.
Martini et al., Mol. Gen. Genet., 263:179, 1993.
Matton et al., Mol. Plant-Microbe Interact., 2:325–331, 1989.
Mazolla et al., Phytopathol. 84:392–397, 1994.
McCabe et al., Biotechnology, 6: 923, 1988.
McElroy et al., Plant Cell, 2:163–171, 1990.
McKently et al., Plant Cell Rep., 14(11): 699–703, 1995.
Odell et al., Nature, 313: 810, 1985.
Osuna et al., Critical Reviews In Microbiology, 20: 107–116, 1994.
Park et al. Plant Mol. Biol. 32(6): 1135–1148, 1996.
Parker et al., Mol Plant-Microbe Interact. 4:19, 1991.
Poszkowski et al., EMBO J. 3: 2719, 1989.
Pyee et al., Plant J., 7: 49–59, 1995.
Rhodes et al., Science, 240:204, 1988. Ride. in: Mechanisms of Resistance to Plant Diseases (ed. R. Fraser: Kluwer Academic Publishers, Boston) pp. 29–61, 1985.
Rogers et al., Meth. in Enzymol, 153: 253–277, 1987.
Rommens et al., Plant Cell, 7:1537–1544, 1995.
Rubino et al., Mol Plant-Microbe Interact, 6:729–734, 1993.
Samac et al., Plant Cell, 3:1063–1072, 1991.
Sambrook et al., *Molecular Cloning: A Laboratory Manual*, Second Edition, Cold Spring Harbor Laboratory Press, Cold Spring Harbor, N.Y., 1989.
Schroder et al., Plant J., 2: 161–172, 1992.
Schroeder et al., Plant Physiol., 101(3): 751–757, 1993.
Sharp et al., J Biol Chem, 259:11312–11320, 1984.
Shipton and Brown, Phytopathological Notes, pp. 1313, 1962.
Smith et al., In: *Genetic Engineering: Principles and Methods*, Setlow et al., Eds., Plenum Press, N.Y., 1–32, 1981.
Somers et al., Bio/Technology, 10: 1589, 1992.
Song et al., Science, 270:1804–1806, 1995.
Toriyama et al., Bio/Technology, 6:10, 1988.
Vasil et al., Bio/Technology, 10: 667, 1992.
Vodkin et al., Cell, 34: 1023, 1983.
Walder et al., Gene, 42: 133, 1986.
Wan and Lemaux, Plant Physiol., 104:37, 1994.
Wang et al., Bio/Technology, 10:691, 1992.
Warner et al., Plant J, 31:191–201, 1993.
Weeks et al., Plant Physiol. 102(4): 1077–1084, 1993.
Winter et al. Mol. Biol. Genet. 211(2): 315–319, 1988.
Whitham et al., Cell, 78:1011–15, 1994.
Yang et al., Plant Cell Rep., 15(7):459–464, 1996.
Yu, Proc. Natl. Acad. Sci. USA. 92:4088–4094 1995.
Zhang and Wu, Theor. Appi. Genet., 76:835, 1988.
Zhang et al., Plant Cell Rep., 7:379, 1988.
Zhang et al., Plant Cell, 7:2241–2252, 1995.

What is claimed is:

1. A nucleic acid segment that, when transformed into a disease-susceptible plant, confers non-host disease resistance to said plant, wherein said nucleic acid segment comprises the sequence as set forth in SEQ ID NO:3.

2. The nucleic acid segment as in claim 1 wherein said segment confers non-host disease resistance to plants by responding to the elicitor INF1.

3. A recombinant DNA expression system comprising an expression vector into which is inserted the nucleic acid segment as in claim 1.

4. A cell transformed with the nucleic acid segment as in claim 1.

5. The cell according to claim 4 wherein said cell is a plant cell selected from the group consisting of gymnosperm, monocot, and dicot.

6. The cell according to claim 5 wherein said cell is a crop plant cell selected from the group consisting of Acacia, apple, banana, barley, bean, broccoli, cabbage, canola, carrot, citrus, coffee, corn, cotton, cucumber, Douglas fir, Eucalyptus, garlic, grape, Loblolly pine, melon, oat, oil palm, onion, an ornamental plant, pea, peanut, pepper, Poplar tree, potato, Radiata pine, rice, rye, sorghum, Southern pine, soybean, strawberry, sugarbeet, sugarcane, sunflower, Sweetgum, tea, tomato, turf, a vine, and wheat.

7. The cell according to claim 4, wherein the cell is from the genus *Agrobacterium*.

8. The cell according to claim 4, wherein said nucleic acid segment is inserted in a recombinant DNA expression system comprising an expression vector.

9. The cell according to claim 4, wherein said plant pathogen is *Phytophthora infestans*.

10. A transgenic plant transformed with the nucleic acid segment as in claim 1 conferring non-host disease resistance to said plant by responding to an avirulence gene in plant pathogens.

11. The transgenic plant as in claim 10, wherein said plant pathogen is *Phytophthora infestans*.

12. The transgenic plant as in claim 10, wherein said plant is selected from the group consisting of gymnosperm, monocot, and dicot.

13. The transgenic plant as in claim 12, wherein said plant is selected from the group consisting of Acacia, apple, banana, barley, bean, broccoli, cabbage, canola, carrot, citrus, coffee, corn, cotton, cucumber, Douglas fir, Eucalyptus, garlic, grape, Loblolly pine, melon, oat, oil palm, onion, an ornamental plant, pea, peanut, pepper, Poplar tree, potato, Radiata pine, rice, rye, sorghum, Southern pine, soybean, strawberry, sugarbeet, sugarcane, sunflower, Sweetgum, tea, tomato, turf, a vine, and wheat.

14. A plant transformed with an R gene as set forth at SEQ ID NO:3, which renders said plant resistant to a pathogen of interest.

* * * * *